(12) United States Patent
Yang et al.

US009024110B2

(10) Patent No.: US 9,024,110 B2
(45) Date of Patent: May 5, 2015

(54) METHODS FOR GLYCO-ENGINEERING PLANT CELLS FOR CONTROLLED HUMAN O-GLYCOSYLATION

(76) Inventors: Zhang Yang, Vanløse (DK); Damian Paul Drew, Gawler East (AU); Emma Adhiambo Arigi, El Paso, TX (US); Peter Ulvskov, Charlottenlund (DK); Steven B. Levery, Holte (DK); Eric Bennett, Lyngby (DK); Henrik Clausen, Holte (DK); Brent Larsen Petersen, Roskilde (DK)

( * ) Notice: Subject to any disclaimer, the term of this patent is extended or adjusted under 35 U.S.C. 154(b) by 379 days.

(21) Appl. No.: 13/070,248

(22) Filed: Mar. 23, 2011

(65) Prior Publication Data
US 2011/0237782 A1 Sep. 29, 2011

Related U.S. Application Data

(60) Provisional application No. 61/316,401, filed on Mar. 23, 2010.

(51) Int. Cl.
| | |
|---|---|
| *C12N 15/82* | (2006.01) |
| *C12N 15/12* | (2006.01) |
| *C12N 15/30* | (2006.01) |
| *C12N 15/31* | (2006.01) |
| *C12N 9/10* | (2006.01) |
| *C12N 9/90* | (2006.01) |
| *C12P 19/00* | (2006.01) |
| *C12P 19/44* | (2006.01) |
| *A61K 38/47* | (2006.01) |
| *C12N 1/13* | (2006.01) |
| *C07K 14/47* | (2006.01) |
| *C12P 21/00* | (2006.01) |

(52) U.S. Cl.
CPC ........ *C12N 15/8257* (2013.01); *C07K 14/4727* (2013.01); *C12N 15/8245* (2013.01); *C12P 21/005* (2013.01)

(58) Field of Classification Search
None
See application file for complete search history.

(56) References Cited

U.S. PATENT DOCUMENTS

| 5,871,990 A | 2/1999 | Clausen et al. |
| 6,465,220 B1 | 10/2002 | Hassan et al. |
| 6,582,910 B1 | 6/2003 | Lam et al. |
| 2009/0068702 A1 | 3/2009 | Chiba et al. |

FOREIGN PATENT DOCUMENTS

WO WO 2007120932 * 8/2007

OTHER PUBLICATIONS

Twyman et al (TRENDS in Biotechnology, 21(12), p. 570-578, 2003).*

Skjot et al (Plant Physiology, 129(1), p. 95-102, 2002); cited on the IDS.*
Kreppel et al (JBC, 274(45), p. 32015-32022, 1999).*
Segawa et al (Eur. J. Biochem. 269, p. 128-138, 2002).*
Creuzenet et al (JBC, 275(25), p. 19060-19067, 2000).*
Leon-Banares et al (Trends in Biotechnology, 22(1), p. 45-42, 2004).*
Rottger et al (Journal of Cell Science, 111, pp. 45-50, 1998).*
Amano et al., "Engineering of mucin-type human glycoproteins in yeast cells," *PNAS* (2008) 105 (9): 3232-3237.
Bélanger et al., "Functional analysis of genes responsible for the synthesis of the B-band O antigen of *Pseudomonas aeruginosa* serotype O6 lipopolysaccharide," *Microbiology* (1999) 145: 3505-3521.
Bennett et al., "cDNA cloning of and expression of a novel human UDP-*N*-acetyl-α-D-galactosamine," *The Journal of Biological Chemistry* (1996) 271 (29): 17006-17012.
Bennett et al., "Cloning of a human UDP-*N*-acetyl-α-D-galactosamine: Polypeptide *N*-acetylgalactosaminyltransferase that complements other GalNAc-transferases in complete O-glycosylation of the MUC1 tandem repeat," *The Journal of Biological Chemistry* (1998) 273 (46): 30472-30481.
Chen et al., "Expression and localization of two low molecular weight GTP-binding proteins, Rab8 and Rab10, by epitope tag," *Proc. Natl. Acad. Sci.* (1993) 90: 6508-6512.

(Continued)

*Primary Examiner* — David T Fox
*Assistant Examiner* — Stephen Uyeno
(74) *Attorney, Agent, or Firm* — Merchant & Gould

(57) ABSTRACT

This invention discloses the development of a novel platform for recombinant production of bioactive glycoproteins and cancer specific vaccines in plants. Plants and plant cell cultures have been humanized with respect to human mucin-type protein O-glycosylation. A panel of plant cell factories for production of recombinant glycoproteins with designed human O-glycosylation, including an improved cancer vaccine candidate, has been developed. The platform provides basis for i) production of an essentially unlimited array of O-glycosylated human glycoprotein therapeutics, such as human interferon α2B and podoplanin, and ii) for further engineering of additional cancer specific O-glycans on glycoproteins of therapeutical value. Currently, mammalian cells are required for human O-glycosylation, but plants offer a unique cell platform for engineering O-glycosylation since they do not perform human type O-glycosylation. Introduction of O-glycosylation into plant cells requires i) that wild-type plant cells do not modify the target peptide substrates and ii) that the appropriate enzymes and substrates are introduced into of plant cells such that O-glycosylation in the secretory pathway proceed and the glycosylated peptide substrates are preferentially exported to the exterior of the cell or accumulated in the cell. In this invention i) the integrity of transiently and stably expressed 'mucin' type target peptides in plants cells has been determined and ii) mucin-type O-glycosylation has been established in plants by transient and stable introduction of a *Pseudomonas aeruginosa* C4-epimerase, the human polypeptide GalNAc-transferases T2 and T4 (GalNAc-T2 and T4) and various human target peptides or proteins. In the present invention GalNAc-T2 and -T4 have been used to produce a Tn cancer glycoform of MUC1.

13 Claims, 23 Drawing Sheets

(56) References Cited

OTHER PUBLICATIONS

Creuzenet et al., "Expression, purification, and biochemical characterization of WbpP, a new UDP-GlcNAc C4 epimerase from *Pseudomonas aeruginosa* serotype O6," *The Journal of Biological Chemistry* (2000) 275 (25): 19060-19067.

Demendi et al., "Towards a better understanding of the substrate specificity of the UDP-N-acetylglucosamine C4 epimerase WbpP," *Biochem J.* (2005) 389: 173-180.

Egelund et al., "Molecular characterization of two *Arabidopsis thaliana* glycosyltransferase mutants, rra1 and rra2, which have a reduced residual arabinose content in a polymer tightly associated with the cellulosic wall residue," *Plant Mol. Biol.* (2007) 64: 439-451.

El Amrani et al., "Coordinate expression and independent subcellular targeting of multiple proteins from single transgene," *Plant Physiology* (2004) 135: 16-24.

Genschik et al., "Structure and promoter activity of a stress and developmentally regulated polyubiquitin-encoding gene of *Nicotiana tabacum*," *Gene* (1994) 148: 195-202.

Gerken et al., "Identification of common and unique peptide substrate preferences for the UDP-GalNAc: Polypeptide α-N-acetylgalactosaminyltransferases T1 and T2 derived from oriented random peptide substrates," *The Journal of Biological Chemistry* (2006) 281 (43): 32403-32416.

Gomord et al., "Posttranslational modification of therapeutic proteins in plants," *Current Opinion in Plant Biology* (2004) 7: 171-181.

Hassan et al., "Control of mucin-type O-glycosylation: O-glycan occupancy is directed by substrate specificities of polypeptide GalNAc-transferases," (2000) Carbohydrates in Chemistry and Biology, Wiley-VCH Verlag GmbH, Weinheim, Germany.

Hattrup et al., "Structure and function of the cell surface (tethered) mucins," *Annu. Rev. Physiol.* (2008) 70: 431-57.

Hieta et al., "Cloning and characterization of a low molecular weight prolyl 4-hydroxylase from *Arabidopsis thaliana*," *The Journal of Biological Chemistry* (2002) 277 (26): 23965-23971.

Horsch et al., "A simple and general method for transferring genes into plants," *Science* (1985) 227 (4691): 1229-1231.

Jamet et al., "Recent advances in plant cell wall proteomics," *Proteomics* (2008) 8: 893-908.

Karnoup et al., "O-linked glycosylation in maize-expressed human IgA1," *Glycobiology* (2005) 15 (10): 965-981.

Kato et al., "Polypeptide GalNAc-transferase T3 and familial tumoral calcinosis," *The Journal of Biological Chemistry* (2006) 281 (27): 18370-18377.

Kauppinen et al., "Molecular cloning and characterization of a rhamnogalacturonan acetylesterase from *Aspergillus aculeatus*," *The Journal of Biological Chemistry* (1995) 270 (45) 10: 27172-27178.

Kobayashi et al., "Engineering a novel multifunctional green fluorescent protein tag for a wide variety of protein research," *PloS ONE* (2008) 3 (12): e3822.

Lee et al., "Increased production of human granulocyte-macrophage colony stimulating factor (hGM-CSF) by the addition of stabilizing polymer in plant suspension cultures," *Journal of Biotechnology* (2002) 96: 205-211.

Mandel et al., "Expression of polypeptide GalNAc-transferases in stratified epithelia and squamous cell carcinomas: immunohistological evaluation using monoclonal antibodies to three members of the GalNAc-transferase family," *Glycobiology* (1999) 9 (1): 43-52.

Mayo et al., Genetic transformation of tobacco NT1 cells with *Agrobacterium tumefaciens*, *Nature Protocols* (2006) 1 (3): 1105-1111.

Nour-Eldin et al., "Advancing uracil-excision based cloning towards an ideal technique for cloning PCR fragments," *Nucleic Acids Research* (2006) 34 (18) e122: 1-8.

Odell et al., "Identification of DNA sequences required for activity of the cauliflower mosaic virus 35S promoter," *Nature* (1985) 313: 810-812.

Petersen et al., "Assay and heterologous expression in *Pichia pastoris* of plant cell wall type-II membrane anchored glycogyltransferases," *Glycoconj J.* (2009) 26: 1235-1246.

Röttger et al., "Localization of three human polypeptide GalNAc-transferases in HeLa cells suggests initiation of O-linked glycosylation throughout the Golgi apparatus," *Journal of Cell Science* (1998) 111: 45-60.

Sainsbury et al., "Extremely high-level and rapid transient protein production in plants without the use of viral replication," *Plant Physiology* (2008) 148: 1212-1218.

Samac et al., "Isolation and characterization of the genes encoding basic and acidic chitinase in *Arabidopsis thaliana*," *Plant Physiol.* (1990) 93: 907-914.

Schaaf et al., "Use of endogenous signal sequences for transient production and efficient secretion by moss," *BMC Biotechnology* (2005) 5 (30): 1-11.

Shimizu et al., "Experimental determination of proline hydroxylation and hydroxyproline arabinogalactosylation motifs in secretory proteins," *The Plant Journal* (2005) 42: 877-889.

Skjøt et al., "Direct interference with Rhamnogalacturonan I biosynthesis in Golgi vesicles," *Plant Physiology* (2002) 129: 95-102.

Sørensen et al., "Cehmoenzymatically synthesized multimeric Tn/STn MUC1 glcopeptides elicit cancer-specific anti-MUC1 antibody responses and override tolerance," *GlycobiologyGlycobiology* (2006) 16 (2): 96-107.

Sørensen et al., "Pectin engineering: Modification of potato pectin by in vivo expression of an endo-1,4-β-D-galactanase," *PNAS* (2000) 97 (13): 7639-7644.

Szymczak et al., "Correction of multi-gene deficiency in vivo using a single 'self-cleaving' 2A peptide-based retroviral vector," *Nature Biotechnology* (2004) 22 (5): 589-594, 760.

Tarp et al., "Idenification of a novel cancer-specific immunodominant glycopeptides epitope in the MUC1 tandem repeat," *Glycobiology* (2007) 17 (2): 197-209.

Tarp et al., "Mucin-type O-glycosylation and its potential use in drug and vaccine development," *Biophysica Acta* (2008) 1780: 546-563.

Ten Hagen et al., "All in the family: the UDP-GalNAc: polypeptide N-acetylgalactosaminyltransferases," *Glycobiology* (2003) 13 (1): 1R-16R.

Tiainen et al., "Characterization of a second *Arabidopsis thaliana* prolyl 4-hydroxylase with distinct substrate specificity," *The Journal of Biological Chemistry* (2005) 280 (2): 1142-1148.

Wandall et al., "Substrate specificities of three members of the human UDP-N-acetyl-α-D-galactosamine: Polypeptide N-acetylgalactosaminyltransferase family, GalNAc-T1, -T2, and -T3," *The Journal of Biological Chemistry* (1997) 272 (38): 23503-23514.

Wandall et al., "The lectin domains of polypeptide GalNAc-transferases exhibit carbohydrate-binding specificity for GalNAc: lectin binding to GalNAc-glycopeptide substrates is required for high density GalNAc-O-glycosylation," *Glycobiology* (2007) 17 (4): 374-387.

White et al., "Purification and cDNA cloning of a human UDP-N-acetyl-α-D-galactosamine: polypeptide N-acetylgalactosaminyltransferase," *The Journal of Biological Chemistry* (1995) 270 (41): 24156-24165.

Xu et al., "High-yields and extended serum half-life of human interferon α2b expressed in tobacco cells as Arabinogalactan-protein fusions," *Biotechnology and Bioengineering* (2007) 97 (5): 997-1008.

Yamamoto et al., "Genetic transformation of duckweed lemna gibba and lemna minor," *In Vitro Cellular & Developmental Biology. Plant* (2001) 37 (3): 349-353.

Qisen Zhang et al., "Gene expression patterns and catalytic properties of UDP-D-glucose 4-epimerases from barley (*Hordeum vulgare* L.)," *Biochem J.* (2006) 394: 115-124.

Daskalova et al., "Engineering of *N. benthamiana* L. plants for production of N-acetylgalactosamine-glycosylated proteins—towards development of a plant-based platform for production of protein therapeutics with mucin type O-glycosylation", BMC Biotechnology, 10:62 (2010).

Dean et al., "The VRG4 Gene is Required for GDP-mannose Transport into the Lumen of the Golgi in the Yeast, *Saccharomyces cerevisiae*", J. Biol. Chem., 272(50):31908-31914 (Dec. 12, 1997; Received for publication Aug. 12, 1997).

* cited by examiner

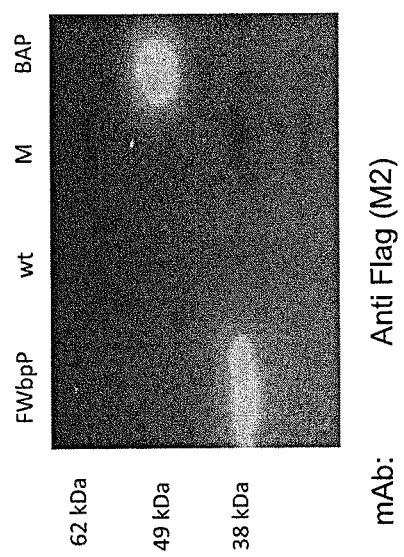
Figure 1. Expression of cytoplasmic WbpP

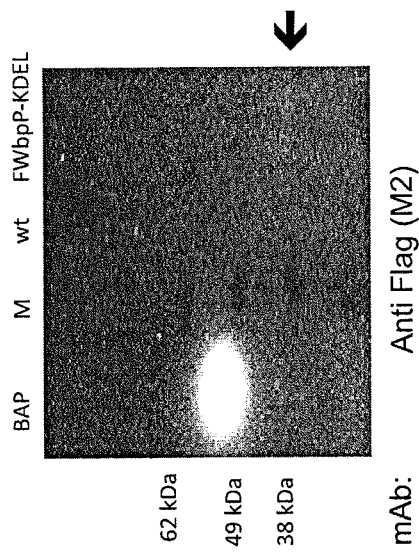
Figure 2. Expression of *ER* targeted WbpP

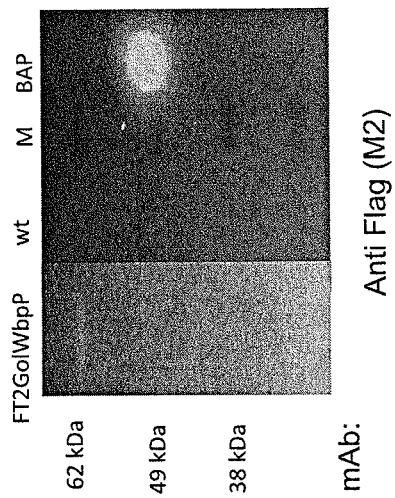
Figure 3. Expression of Golgi targeted WbpP

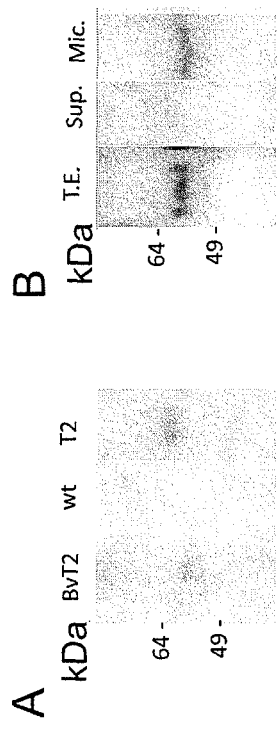
Figure 4. Expression of Golgi targeted GalNAc-T2

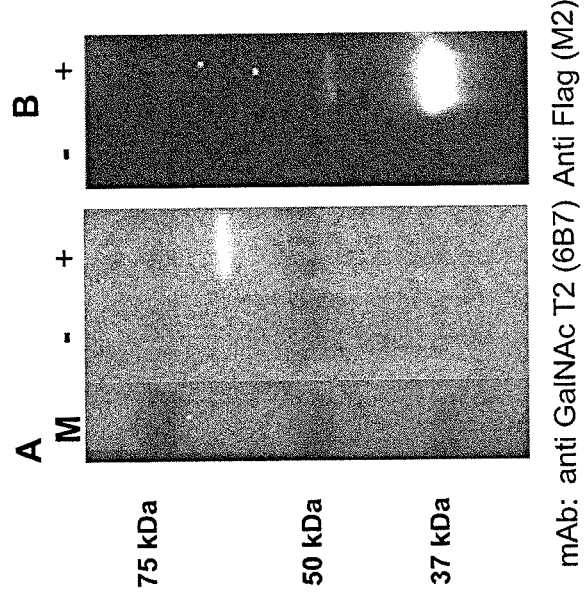
Figure 5. Expression of cytoplasmic FWbpP and HA tagged Golgi GalNAc-T2 from one polycistronic transcript

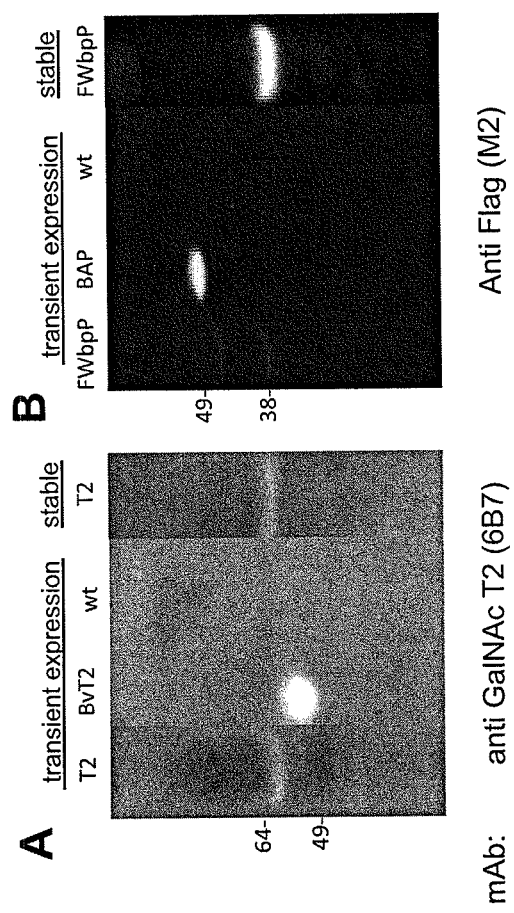
Figure 6. Expression of Golgi GalNAc-T2 and cytoplasmic WbpPF from one polycistronic transcript

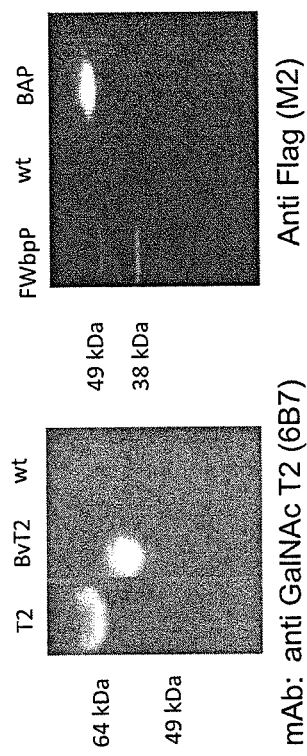
Figure 7. Expression of cytoplasmic FWbpP and Golgi GalNAc-T2 from one polycistronic transcript

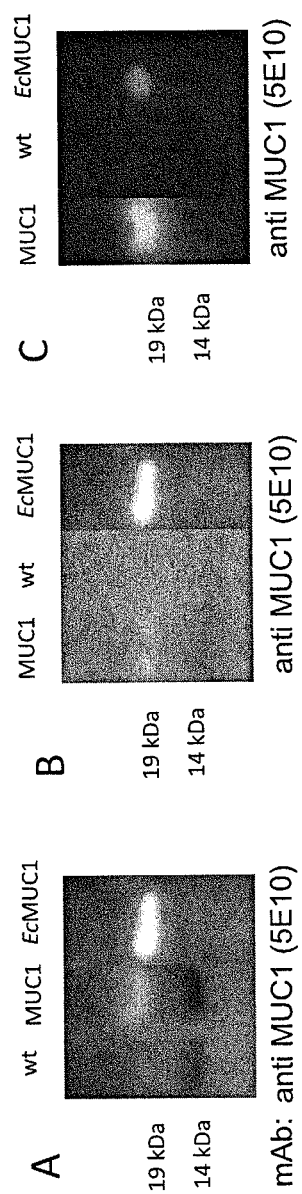
Figure 8. Expression of MUC1-3.5TR

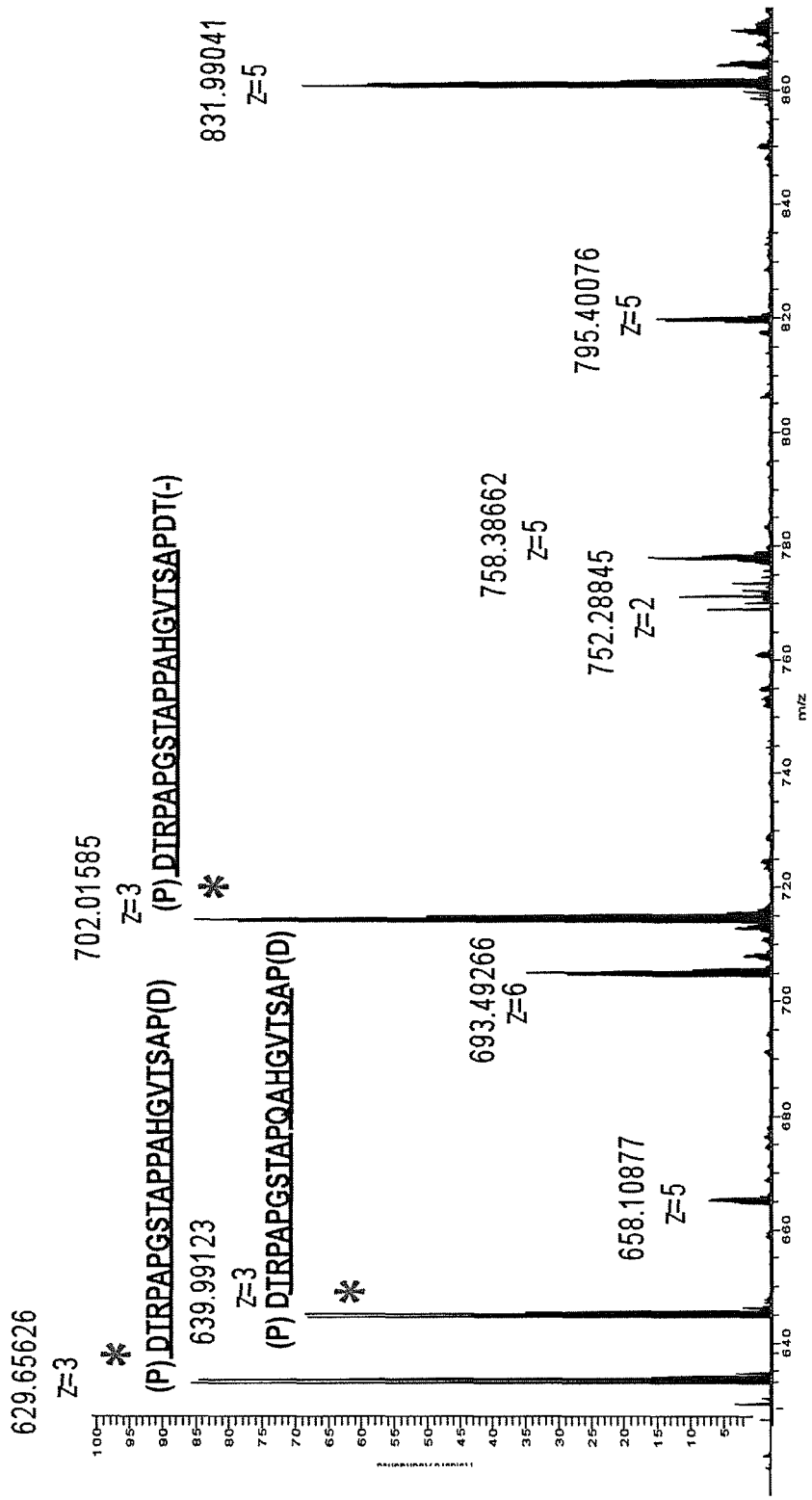
Figure 9. Structure of *E. coli* derived MUC1-3.5TR

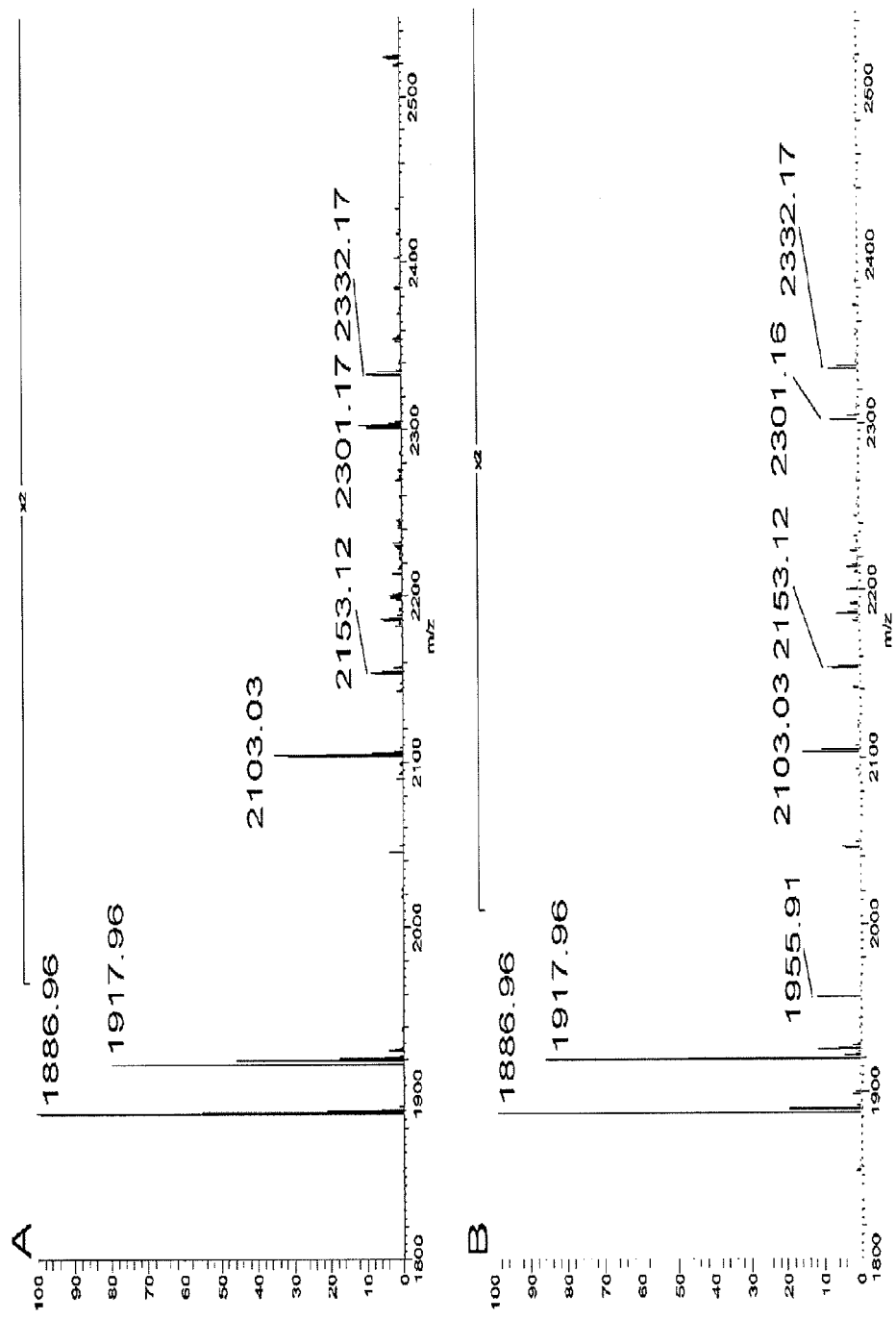
Figure 10. Structure of A. thaliana derived MUC1-3.5TR

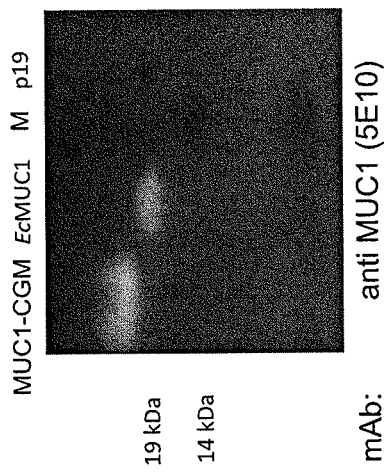
Figure 11. Mucin-type O-glycosylation of MUC1-3.5TR with fused C-terminal Glycomodule

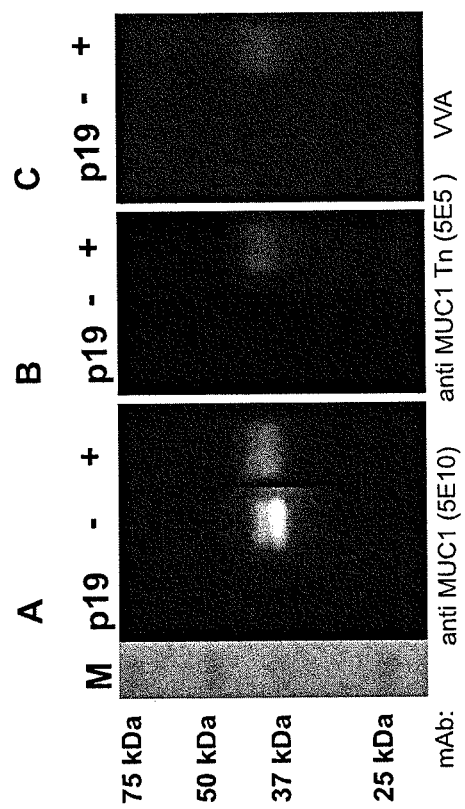
Figure 12. Mucin-type O-glycosylation of MUC1-3.5TR-Yfp target peptide

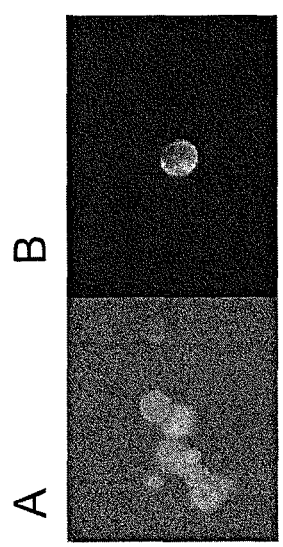
Figure 13. Transient expression of MUC1-3.5TR-Yfp in the moss *Physcomitrella patens*

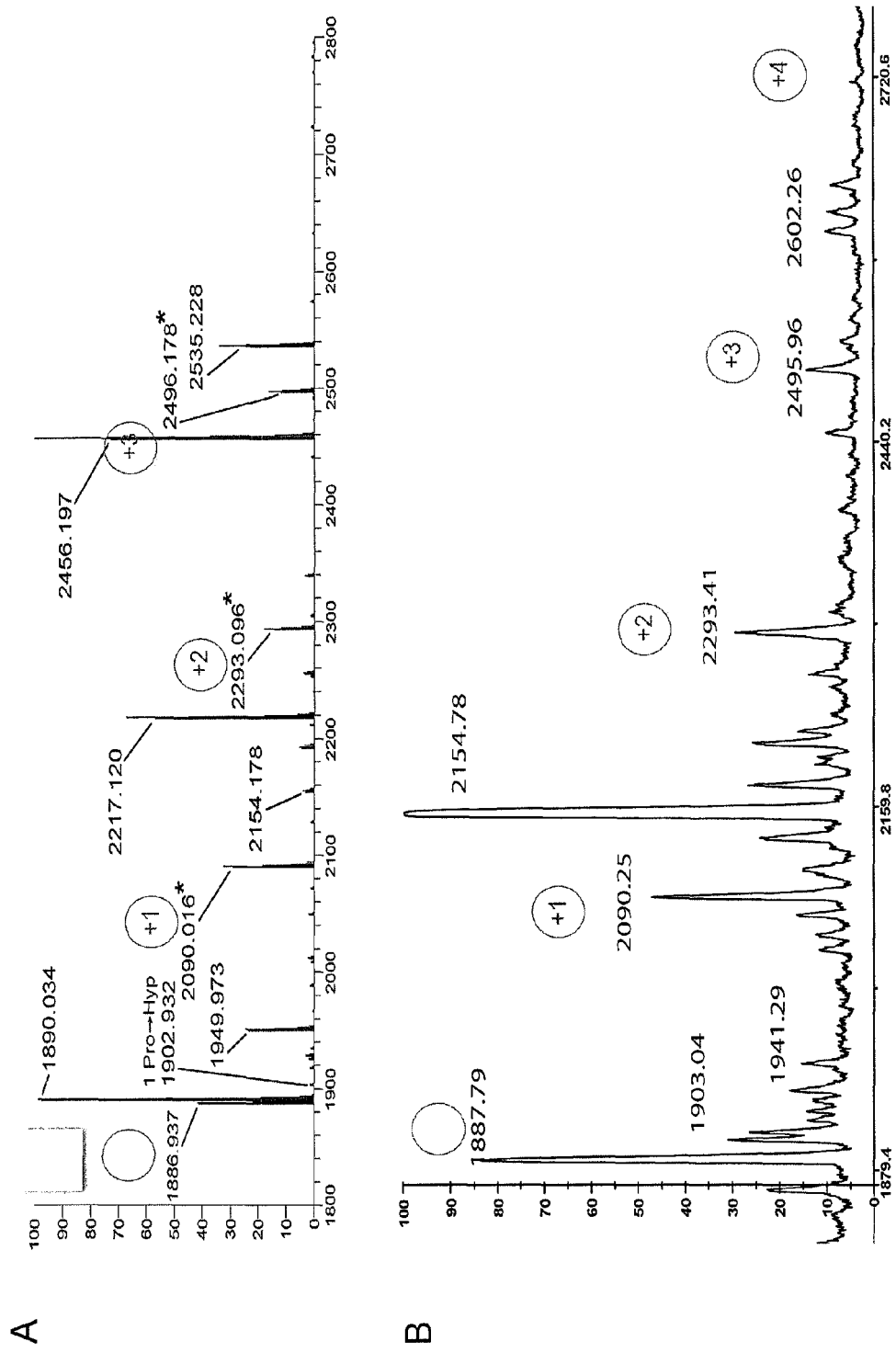
Figure 14. Structure of MUC1-3.5TR-Yfp expressed in WT and O-glycosylation capacity background

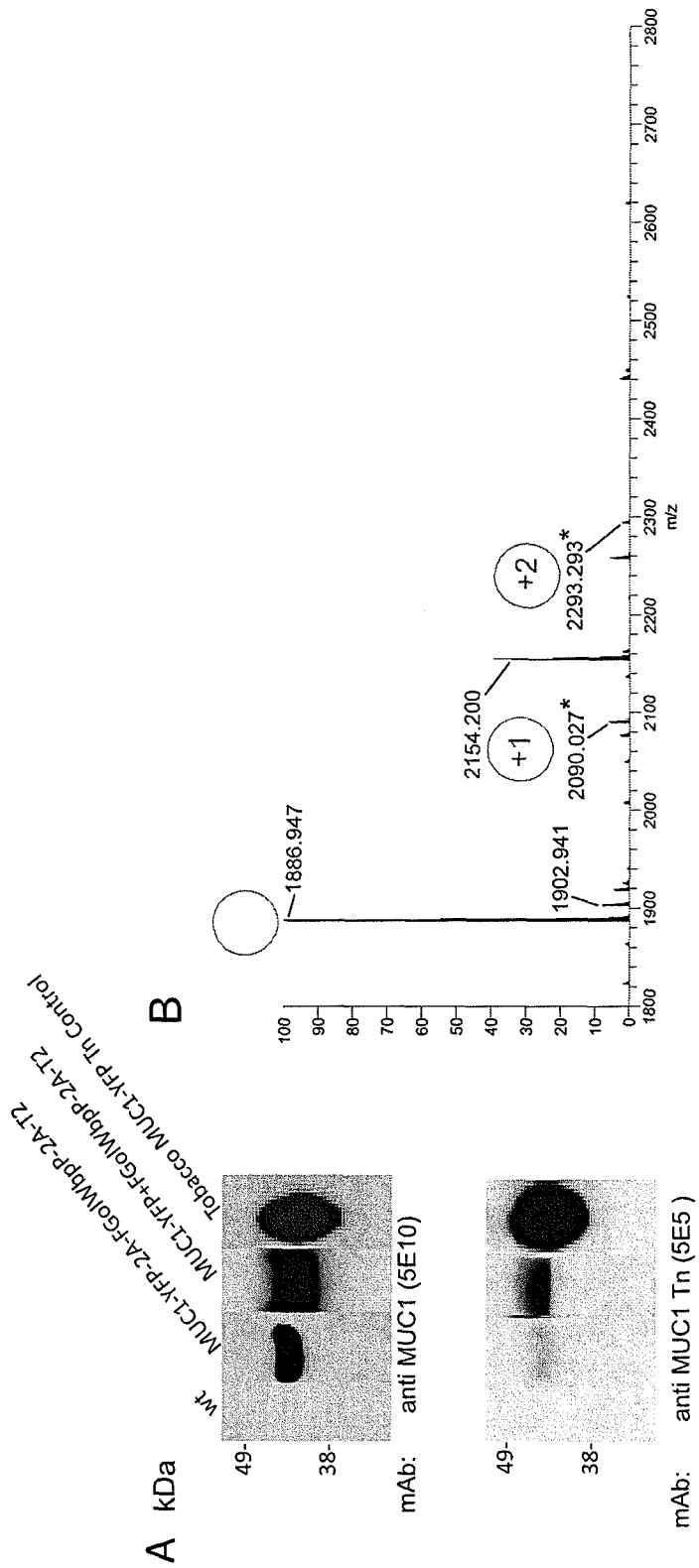
Figure 15. Single and combined constructs encoding Golgi targeted epimerase and GalNAc-T2 conferring Mucin-type O-glycosylation

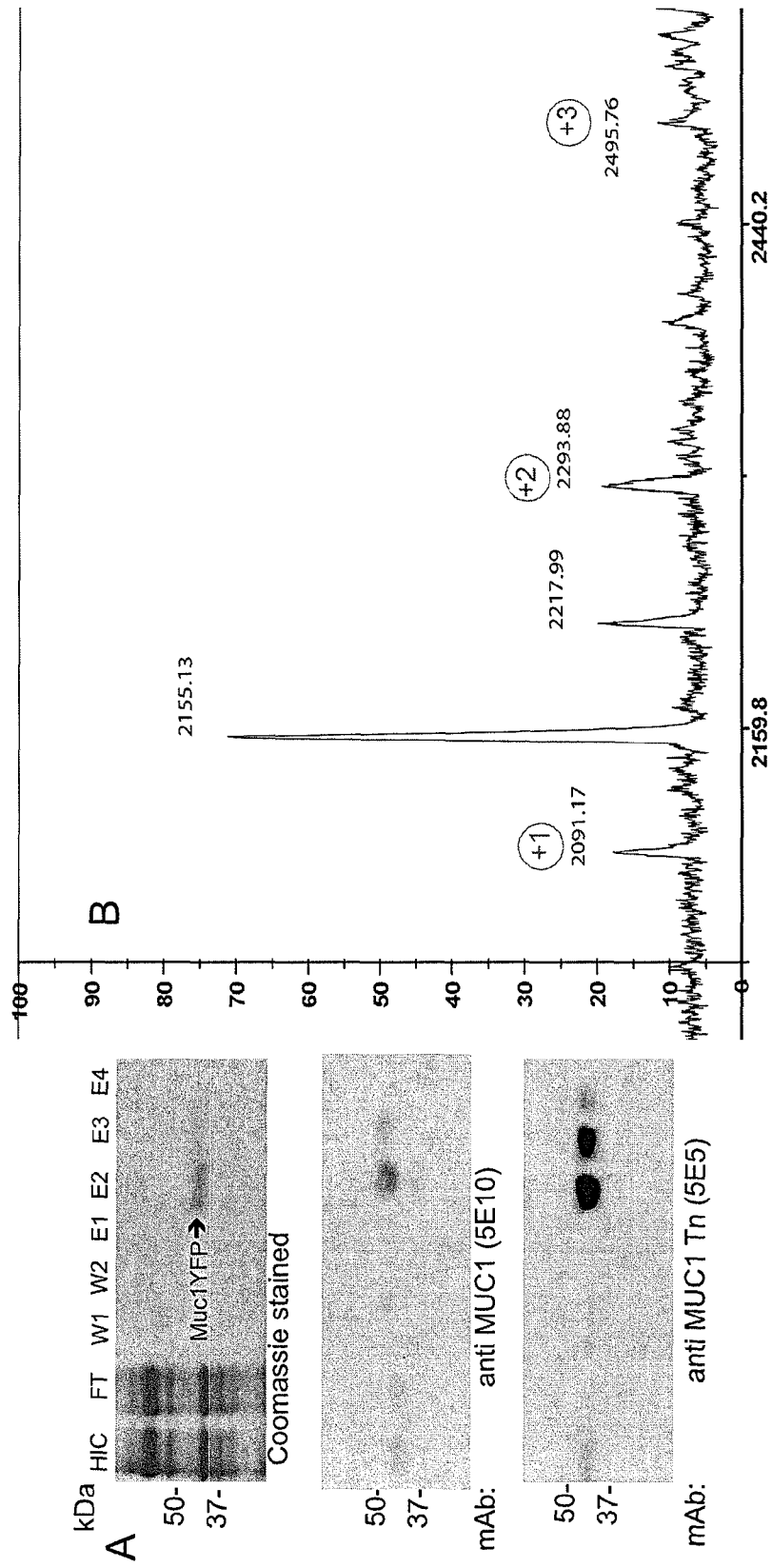
Figure 16. Stable Arabidopsis line expressing a single construct conferring Mucin-type O-glycosylation

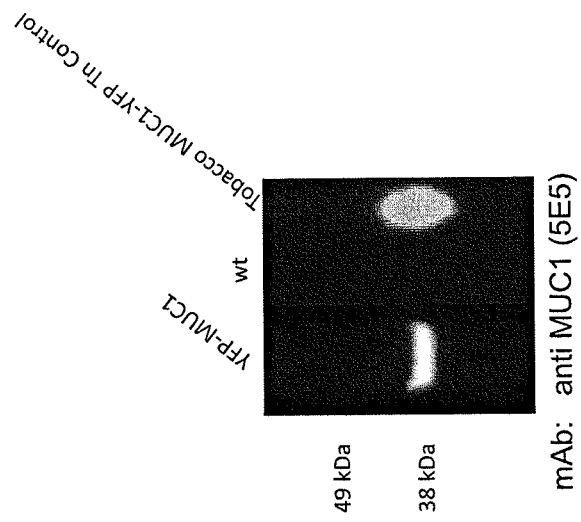
Figure 17. Mucin-type O-glycosylation of Yfp-MUC1-3.5TR target peptide

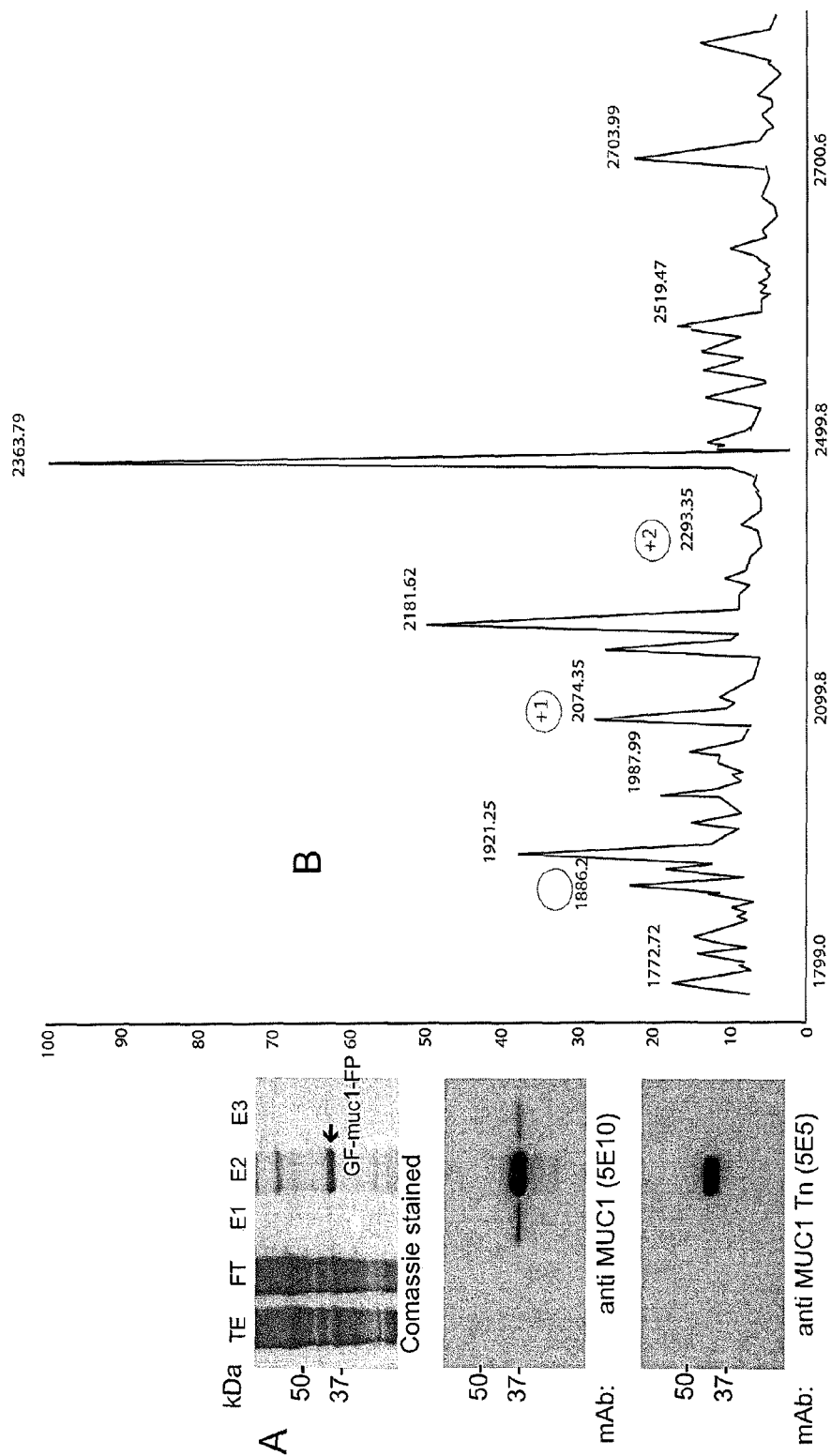
Figure 18. Mucin-type O-glycosylation of embedded G-MUC1-2TR-fp target peptide

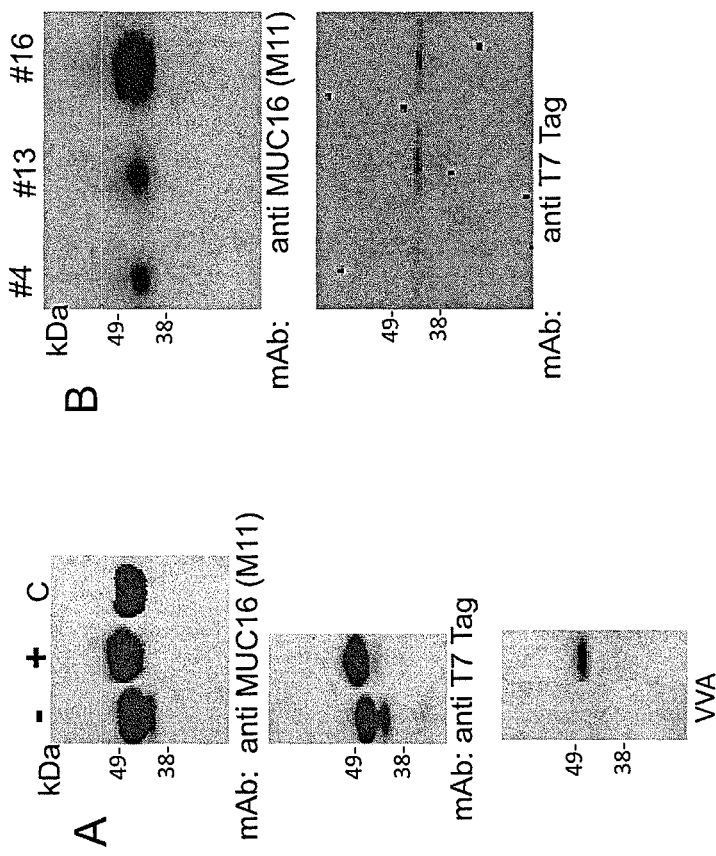
Figure 19. Expression and Mucin-type O-glycosylation of MUC16 target peptide

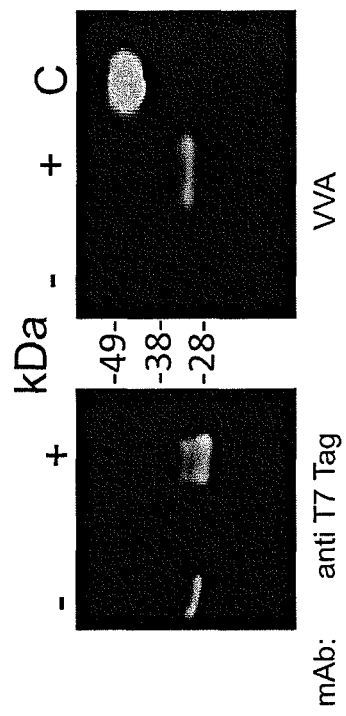
Figure 20. Expression and O-glycosylation of human interferon α2B

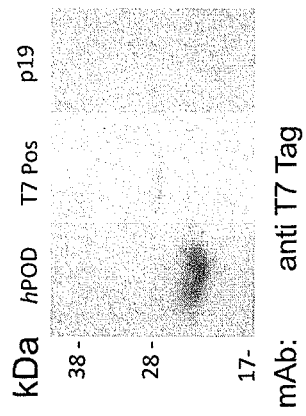
Figure 21. Expression of human podoplanin (hPOD)

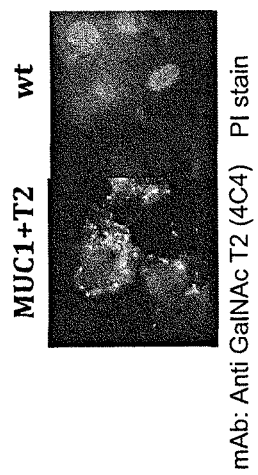
Figure 22. Expression of MUC1-3.5TR & GalNAc-T2 and localization of GalNAc-T2 in stably transformed tobacco BY 2 cells

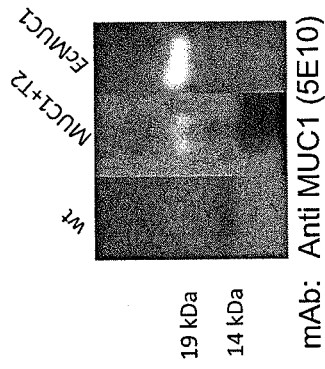
Figure 23. Co-Expression of MUC1-3.5TR and GalNAc-T2 in stably transformed *Arabidopsis thaliana*

US 9,024,110 B2

SEQUENCE LISTING

```
<160> NUMBER OF SEQ ID NOS: 76

<210> SEQ ID NO 1
<211> LENGTH: 357
<212> TYPE: PRT
<213> ORGANISM: Artificial Sequence
<220> FEATURE:
<223> OTHER INFORMATION: Cytosolic WbpP with N-terminal Flag tag

<400> SEQUENCE: 1
```

Met Asp Tyr Lys Asp Asp Asp Lys His Val Glu Phe Ala Met Val
1               5                   10                  15

Met Met Ser Arg Tyr Glu Glu Leu Arg Lys Glu Leu Pro Ala Gln Pro
            20                  25                  30

Lys Val Trp Leu Ile Thr Gly Val Ala Gly Ser Ile Gly Ser Asn Leu
        35                  40                  45

Leu Glu Thr Leu Leu Lys Leu Asp Gln Lys Val Val Gly Leu Asp Asn
    50                  55                  60

Phe Ala Thr Gly His Gln Arg Asn Leu Asp Glu Val Arg Ser Leu Ala
65                  70                  75                  80

Ser Glu Lys Gln Trp Ser Asn Phe Lys Phe Ile Gln Gly Asp Ile Arg
                85                  90                  95

Asn Leu Asp Asp Cys Asn Asn Ala Cys Ala Gly Val Asp Tyr Val Leu
            100                 105                 110

His Gln Ala Ala Leu Gly Ser Val Pro Arg Ser Ile Asn Asp Pro Ile
        115                 120                 125

Thr Ser Asn Ala Thr Asn Ile Asp Gly Phe Leu Asn Met Leu Ile Ala
    130                 135                 140

Ala Arg Asp Ala Lys Val Gln Ser Phe Thr Tyr Ala Ala Ser Ser Ser
145                 150                 155                 160

Thr Tyr Gly Asp His Pro Gly Leu Pro Lys Val Glu Asp Thr Ile Gly
                165                 170                 175

Lys Pro Leu Ser Pro Tyr Ala Val Thr Lys Tyr Val Asn Glu Leu Tyr
            180                 185                 190

Ala Asp Val Phe Ser Arg Cys Tyr Gly Phe Ser Thr Ile Gly Leu Arg
        195                 200                 205

Tyr Phe Asn Val Phe Gly Arg Arg Gln Asp Pro Asn Gly Ala Tyr Ala
    210                 215                 220

Ala Val Ile Pro Lys Trp Thr Ser Ser Met Ile Gln Gly Asp Asp Val
225                 230                 235                 240

Tyr Ile Asn Gly Asp Gly Glu Thr Ser Arg Asp Phe Cys Tyr Ile Glu
                245                 250                 255

Asn Thr Val Gln Ala Asn Leu Leu Ala Ala Thr Ala Gly Leu Asp Ala
            260                 265                 270

Arg Asn Gln Val Tyr Asn Ile Ala Val Gly Gly Arg Thr Ser Leu Asn
        275                 280                 285

Gln Leu Phe Phe Ala Leu Arg Asp Gly Leu Ala Glu Asn Gly Val Ser
    290                 295                 300

Tyr His Arg Glu Pro Val Tyr Arg Asp Phe Arg Glu Gly Asp Val Arg
305                 310                 315                 320

His Ser Leu Ala Asp Ile Ser Lys Ala Ala Lys Leu Leu Gly Tyr Ala 325                 330                 335
Pro Lys Tyr Asp Val Ser Ala Gly Val Ala Leu Ala Met Pro Trp Tyr
                340                 345                 350
Ile Met Phe Leu Lys
            355

<210> SEQ ID NO 2
<211> LENGTH: 383
<212> TYPE: PRT
<213> ORGANISM: Artificial Sequence
<220> FEATURE:
<223> OTHER INFORMATION: ER localized N-terminal Flag tagged WbpP with
      N-terminal AaSP signal peptide and C-terminal KDEL ER retention
      sequence

<400> SEQUENCE: 2

Met Lys Thr Ala Ala Leu Ala Pro Leu Phe Phe Leu Pro Ser Ala Leu
1               5                   10                  15

Ala Asp Tyr Lys Asp Asp Asp Met Asp Tyr Lys Asp Asp Asp Asp Lys
            20                  25                  30

His Val Glu Phe Ala Met Val Met Met Ser Arg Tyr Glu Glu Leu Arg
        35                  40                  45

Lys Glu Leu Pro Ala Gln Pro Lys Val Trp Leu Ile Thr Gly Val Ala
    50                  55                  60

Gly Ser Ile Gly Ser Asn Leu Leu Glu Thr Leu Leu Lys Leu Asp Gln
65                  70                  75                  80

Lys Val Val Gly Leu Asp Asn Phe Ala Thr Gly His Gln Arg Asn Leu
                85                  90                  95

Asp Glu Val Arg Ser Leu Ala Ser Glu Lys Gln Trp Ser Asn Phe Lys
            100                 105                 110

Phe Ile Gln Gly Asp Ile Arg Asn Leu Asp Asp Cys Asn Asn Ala Cys
        115                 120                 125

Ala Gly Val Asp Tyr Val Leu His Gln Ala Ala Leu Gly Ser Val Pro
    130                 135                 140

Arg Ser Ile Asn Asp Pro Ile Thr Ser Asn Ala Thr Asn Ile Asp Gly
145                 150                 155                 160

Phe Leu Asn Met Leu Ile Ala Ala Arg Asp Ala Lys Val Gln Ser Phe
                165                 170                 175

Thr Tyr Ala Ala Ser Ser Ser Thr Tyr Gly Asp His Pro Gly Leu Pro
            180                 185                 190

Lys Val Glu Asp Thr Ile Gly Lys Pro Leu Ser Pro Tyr Ala Val Thr
        195                 200                 205

Lys Tyr Val Asn Glu Leu Tyr Ala Asp Val Phe Ser Arg Cys Tyr Gly
    210                 215                 220

Phe Ser Thr Ile Gly Leu Arg Tyr Phe Asn Val Phe Gly Arg Arg Gln
225                 230                 235                 240

Asp Pro Asn Gly Ala Tyr Ala Ala Val Ile Pro Lys Trp Thr Ser Ser
                245                 250                 255

Met Ile Gln Gly Asp Asp Val Tyr Ile Asn Gly Asp Gly Glu Thr Ser
            260                 265                 270

Arg Asp Phe Cys Tyr Ile Glu Asn Thr Val Gln Ala Asn Leu Leu Ala
        275                 280                 285

Ala Thr Ala Gly Leu Asp Ala Arg Asn Gln Val Tyr Asn Ile Ala Val
    290                 295                 300

Gly Gly Arg Thr Ser Leu Asn Gln Leu Phe Phe Ala Leu Arg Asp Gly
305                 310                 315                 320

Leu Ala Glu Asn Gly Val Ser Tyr His Arg Glu Pro Val Tyr Arg Asp
            325                 330                 335

Phe Arg Glu Gly Asp Val Arg His Ser Leu Ala Asp Ile Ser Lys Ala
            340                 345                 350

Ala Lys Leu Leu Gly Tyr Ala Pro Lys Tyr Asp Val Ser Ala Gly Val
        355                 360                 365

Ala Leu Ala Met Pro Trp Tyr Ile Met Phe Leu Lys Asp Glu Leu
        370                 375                 380

<210> SEQ ID NO 3
<211> LENGTH: 488
<212> TYPE: PRT
<213> ORGANISM: Artificial Sequence
<220> FEATURE:
<223> OTHER INFORMATION: Golgi localized WbpP with N-terminal Flag tag,
      N-terminally fused to GalNAc-T2 TMD and stem region

<400> SEQUENCE: 3

Met Asp Tyr Lys Asp Asp Asp Lys Met Arg Arg Ser Arg Met
1               5                   10                  15

Leu Leu Cys Phe Ala Phe Leu Trp Val Leu Gly Ile Ala Tyr Tyr Met
            20                  25                  30

Tyr Ser Gly Gly Gly Ser Ala Leu Ala Gly Gly Ala Gly Gly Ala
        35                  40                  45

Gly Arg Lys Glu Asp Trp Asn Glu Ile Asp Pro Ile Lys Lys Lys Asp
    50                  55                  60

Leu His His Ser Asn Gly Glu Glu Lys Ala Gln Ser Met Glu Thr Leu
65                  70                  75                  80

Pro Pro Gly Lys Val Arg Trp Pro Asp Phe Asn Gln Glu Ala Tyr Val
                85                  90                  95

Gly Gly Thr Met Val Arg Ser Gly Gln Asp Pro Tyr Ala Arg Asn Lys
            100                 105                 110

Phe Asn Gln Val Glu Ser Asp Lys Leu Arg Met Asp Arg Ala Ile Pro
        115                 120                 125

Asp Thr Arg His Asp Gln Cys Gln Arg Lys Gln Trp Arg Val Asp Leu
    130                 135                 140

Pro Ala Thr Met Met Ser Arg Tyr Glu Glu Leu Arg Lys Glu Leu Pro
145                 150                 155                 160

Ala Gln Pro Lys Val Trp Leu Ile Thr Gly Val Ala Gly Ser Ile Gly
                165                 170                 175

Ser Asn Leu Leu Glu Thr Leu Leu Lys Leu Asp Gln Lys Val Val Gly
            180                 185                 190

Leu Asp Asn Phe Ala Thr Gly His Gln Arg Asn Leu Asp Glu Val Arg
        195                 200                 205

Ser Leu Ala Ser Glu Lys Gln Trp Ser Asn Phe Lys Phe Ile Gln Gly
    210                 215                 220

Asp Ile Arg Asn Leu Asp Asp Cys Asn Asn Ala Cys Ala Gly Val Asp
225                 230                 235                 240

Tyr Val Leu His Gln Ala Ala Leu Gly Ser Val Pro Arg Ser Ile Asn
                245                 250                 255

Asp Pro Ile Thr Ser Asn Ala Thr Asn Ile Asp Gly Phe Leu Asn Met
            260                 265                 270

Leu Ile Ala Ala Arg Asp Ala Lys Val Gln Ser Phe Thr Tyr Ala Ala
        275                 280                 285

Ser Ser Ser Thr Tyr Gly Asp His Pro Gly Leu Pro Lys Val Glu Asp

```
                290                 295                 300
Thr Ile Gly Lys Pro Leu Ser Pro Tyr Ala Val Thr Lys Tyr Val Asn
305                 310                 315                 320

Glu Leu Tyr Ala Asp Val Phe Ser Arg Cys Tyr Gly Phe Ser Thr Ile
                325                 330                 335

Gly Leu Arg Tyr Phe Asn Val Phe Gly Arg Arg Gln Asp Pro Asn Gly
                340                 345                 350

Ala Tyr Ala Ala Val Ile Pro Lys Trp Thr Ser Met Ile Gln Gly
                355                 360                 365

Asp Asp Val Tyr Ile Asn Gly Asp Gly Glu Thr Ser Arg Asp Phe Cys
                370                 375                 380

Tyr Ile Glu Asn Thr Val Gln Ala Asn Leu Leu Ala Ala Thr Ala Gly
385                 390                 395                 400

Leu Asp Ala Arg Asn Gln Val Tyr Asn Ile Ala Val Gly Gly Arg Thr
                405                 410                 415

Ser Leu Asn Gln Leu Phe Phe Ala Leu Arg Asp Gly Leu Ala Glu Asn
                420                 425                 430

Gly Val Ser Tyr His Arg Glu Pro Val Tyr Arg Asp Phe Arg Glu Gly
                435                 440                 445

Asp Val Arg His Ser Leu Ala Asp Ile Ser Lys Ala Ala Lys Leu Leu
450                 455                 460

Gly Tyr Ala Pro Lys Tyr Asp Val Ser Ala Gly Val Ala Leu Ala Met
465                 470                 475                 480

Pro Trp Tyr Ile Met Phe Leu Lys
                485

<210> SEQ ID NO 4
<211> LENGTH: 119
<212> TYPE: PRT
<213> ORGANISM: Artificial Sequence
<220> FEATURE:
<223> OTHER INFORMATION: MUC1- 3.5 TR with an N-terminal hexa His tag
      and an N-terminal signal sequence AaSP for secretion and

<400> SEQUENCE: 4

Met Lys Thr Ala Ala Leu Ala Pro Leu Phe Phe Leu Pro Ser Ala Leu
1               5                   10                  15

Ala Thr Thr His Val His His His His His Ser Ser Gly Leu Val
                20                  25                  30

Pro Arg Gly Ser His Met Ala Ser Met Thr Gly Gly Gln Gln Met Gly
                35                  40                  45

Arg Asp Pro Asn Ser Val Thr Ser Ala Pro Asp Thr Arg Pro Ala Pro
50                  55                  60

Gly Ser Thr Ala Pro Gln Ala His Gly Val Thr Ser Ala Pro Asp Thr
65                  70                  75                  80

Arg Pro Ala Pro Gly Ser Thr Ala Pro Pro Ala His Gly Val Thr Ser
                85                  90                  95

Ala Pro Asp Thr Arg Pro Ala Pro Gly Ser Thr Ala Pro Pro Ala His
                100                 105                 110

Gly Thr Ser Ala Pro Asp Thr
        115

<210> SEQ ID NO 5
<211> LENGTH: 571
<212> TYPE: PRT
<213> ORGANISM: Homo sapiens
```

```
<400> SEQUENCE: 5

Met Arg Arg Arg Ser Arg Met Leu Leu Cys Phe Ala Phe Leu Trp Val
1               5                   10                  15

Leu Gly Ile Ala Tyr Tyr Met Tyr Ser Gly Gly Ser Ala Leu Ala
            20                  25                  30

Gly Gly Ala Gly Gly Ala Gly Arg Lys Glu Asp Trp Asn Glu Ile
        35                  40                  45

Asp Pro Ile Lys Lys Lys Asp Leu His His Ser Asn Gly Glu Glu Lys
50                  55                  60

Ala Gln Ser Met Glu Thr Leu Pro Pro Gly Lys Val Arg Trp Pro Asp
65                  70                  75                  80

Phe Asn Gln Glu Ala Tyr Val Gly Gly Thr Met Val Arg Ser Gly Gln
                85                  90                  95

Asp Pro Tyr Ala Arg Asn Lys Phe Asn Gln Val Glu Ser Asp Lys Leu
            100                 105                 110

Arg Met Asp Arg Ala Ile Pro Asp Thr Arg His Asp Gln Cys Gln Arg
        115                 120                 125

Lys Gln Trp Arg Val Asp Leu Pro Ala Thr Ser Val Val Ile Thr Phe
130                 135                 140

His Asn Glu Ala Arg Ser Ala Leu Leu Arg Thr Val Val Ser Val Leu
145                 150                 155                 160

Lys Lys Ser Pro Pro His Leu Ile Lys Glu Ile Ile Leu Val Asp Asp
                165                 170                 175

Tyr Ser Asn Asp Pro Glu Asp Gly Ala Leu Leu Gly Lys Ile Glu Lys
            180                 185                 190

Val Arg Val Leu Arg Asn Asp Arg Arg Glu Gly Leu Met Arg Ser Arg
        195                 200                 205

Val Arg Gly Ala Asp Ala Ala Gln Ala Lys Val Leu Thr Phe Leu Asp
210                 215                 220

Ser His Cys Glu Cys Asn Glu His Trp Leu Glu Pro Leu Leu Glu Arg
225                 230                 235                 240

Val Ala Glu Asp Arg Thr Arg Val Val Ser Pro Ile Ile Asp Val Ile
                245                 250                 255

Asn Met Asp Asn Phe Gln Tyr Val Gly Ala Ser Ala Asp Leu Lys Gly
            260                 265                 270

Gly Phe Asp Trp Asn Leu Val Phe Lys Trp Asp Tyr Met Thr Pro Glu
        275                 280                 285

Gln Arg Arg Ser Arg Gln Gly Asn Pro Val Ala Pro Ile Lys Thr Pro
290                 295                 300

Met Ile Ala Gly Gly Leu Phe Val Met Asp Lys Phe Tyr Phe Glu Glu
305                 310                 315                 320

Leu Gly Lys Tyr Asp Met Met Met Asp Val Trp Gly Gly Glu Asn Leu
                325                 330                 335

Glu Ile Ser Phe Arg Val Trp Gln Cys Gly Gly Ser Leu Glu Ile Ile
            340                 345                 350

Pro Cys Ser Arg Val Gly His Val Phe Arg Lys Gln His Pro Tyr Thr
        355                 360                 365

Phe Pro Gly Gly Ser Gly Thr Val Phe Ala Arg Asn Thr Arg Arg Ala
370                 375                 380

Ala Glu Val Trp Met Asp Glu Tyr Lys Asn Phe Tyr Tyr Ala Ala Val
385                 390                 395                 400

Pro Ser Ala Arg Asn Val Pro Tyr Gly Asn Ile Gln Ser Arg Leu Glu
                405                 410                 415
```

```
Leu Arg Lys Lys Leu Ser Cys Lys Pro Phe Lys Trp Tyr Leu Glu Asn
            420                 425                 430

Val Tyr Pro Glu Leu Arg Val Pro Asp His Gln Asp Ile Ala Phe Gly
        435                 440                 445

Ala Leu Gln Gln Gly Thr Asn Cys Leu Asp Thr Leu Gly His Phe Ala
    450                 455                 460

Asp Gly Val Val Gly Val Tyr Glu Cys His Asn Ala Gly Gly Asn Gln
465                 470                 475                 480

Glu Trp Ala Leu Thr Lys Glu Lys Ser Val Lys His Met Asp Leu Cys
                485                 490                 495

Leu Thr Val Val Asp Arg Ala Pro Gly Ser Leu Ile Lys Leu Gln Gly
            500                 505                 510

Cys Arg Glu Asn Asp Ser Arg Gln Lys Trp Glu Gln Ile Glu Gly Asn
        515                 520                 525

Ser Lys Leu Arg His Val Gly Ser Asn Leu Cys Leu Asp Ser Arg Thr
    530                 535                 540

Ala Lys Ser Gly Gly Leu Ser Val Glu Val Cys Gly Pro Ala Leu Ser
545                 550                 555                 560

Gln Gln Trp Lys Phe Thr Leu Asn Leu Gln Gln
                565                 570

<210> SEQ ID NO 6
<211> LENGTH: 578
<212> TYPE: PRT
<213> ORGANISM: Homo sapiens

<400> SEQUENCE: 6

Met Ala Val Arg Trp Thr Trp Ala Gly Lys Thr Cys Leu Leu Leu Ala
1               5                   10                  15

Phe Leu Thr Val Ala Tyr Ile Phe Val Glu Leu Leu Val Ser Thr Phe
            20                  25                  30

His Ala Ser Ala Gly Ala Gly Arg Ala Arg Glu Leu Gly Ser Arg Arg
        35                  40                  45

Leu Ser Asp Leu Gln Lys Asn Thr Glu Asp Leu Ser Arg Pro Leu Tyr
    50                  55                  60

Lys Lys Pro Pro Ala Asp Ser Arg Ala Leu Gly Glu Trp Gly Lys Ala
65                  70                  75                  80

Ser Lys Leu Gln Leu Asn Glu Asp Glu Leu Lys Gln Gln Glu Glu Leu
                85                  90                  95

Ile Glu Arg Tyr Ala Ile Asn Ile Tyr Leu Ser Asp Arg Ile Ser Leu
            100                 105                 110

His Arg His Ile Glu Asp Lys Arg Met Tyr Glu Cys Lys Ser Gln Lys
        115                 120                 125

Phe Asn Tyr Arg Thr Leu Pro Thr Thr Ser Val Ile Ala Phe Tyr
    130                 135                 140

Asn Glu Ala Trp Ser Thr Leu Leu Arg Thr Ile His Ser Val Leu Glu
145                 150                 155                 160

Thr Ser Pro Ala Val Leu Leu Lys Glu Ile Ile Leu Val Asp Asp Leu
                165                 170                 175

Ser Asp Arg Val Tyr Leu Lys Thr Gln Leu Glu Thr Tyr Ile Ser Asn
            180                 185                 190

Leu Asp Arg Val Arg Leu Ile Arg Thr Asn Lys Arg Glu Gly Leu Val
        195                 200                 205

Arg Ala Arg Leu Ile Gly Ala Thr Phe Ala Thr Gly Asp Val Leu Thr
```

```
            210                 215                 220
Phe Leu Tyr Cys His Cys Glu Cys Asn Ser Gly Trp Leu Glu Pro Leu
225                 230                 235                 240

Leu Glu Arg Ile Gly Arg Tyr Glu Thr Ala Val Val Cys Pro Val Ile
                245                 250                 255

Asp Thr Ile Asp Trp Asn Thr Phe Glu Phe Tyr Met Gln Ile Gly Glu
            260                 265                 270

Pro Met Ile Gly Gly Phe Asp Trp Arg Leu Thr Phe Gln Trp His Ser
        275                 280                 285

Val Pro Lys Gln Glu Arg Asp Arg Arg Ile Ser Arg Ile Asp Pro Ile
290                 295                 300

Arg Ser Pro Thr Met Ala Gly Gly Leu Phe Ala Val Ser Lys Lys Tyr
305                 310                 315                 320

Phe Gln Tyr Leu Gly Thr Tyr Asp Thr Gly Met Glu Val Trp Gly Gly
                325                 330                 335

Glu Asn Leu Glu Leu Ser Phe Arg Val Trp Gln Cys Gly Gly Lys Leu
            340                 345                 350

Glu Ile His Pro Cys Ser His Val Gly His Val Phe Pro Lys Arg Ala
        355                 360                 365

Pro Tyr Ala Arg Pro Asn Phe Leu Gln Asn Thr Ala Arg Ala Ala Glu
370                 375                 380

Val Trp Met Asp Glu Tyr Lys Glu His Phe Tyr Asn Arg Asn Pro Pro
385                 390                 395                 400

Ala Arg Lys Glu Ala Tyr Gly Asp Ile Ser Glu Arg Lys Leu Leu Arg
                405                 410                 415

Glu Arg Leu Arg Cys Lys Ser Phe Asp Trp Tyr Leu Lys Asn Val Phe
            420                 425                 430

Pro Asn Leu His Val Pro Glu Asp Arg Pro Gly Trp His Gly Ala Ile
        435                 440                 445

Arg Ser Arg Gly Ile Ser Ser Glu Cys Leu Asp Tyr Asn Ser Pro Asp
450                 455                 460

Asn Asn Pro Thr Gly Ala Asn Leu Ser Leu Phe Gly Cys His Gly Gln
465                 470                 475                 480

Gly Gly Asn Gln Phe Phe Glu Tyr Thr Ser Asn Lys Glu Ile Arg Phe
                485                 490                 495

Asn Ser Val Thr Glu Leu Cys Ala Glu Val Pro Glu Gln Lys Asn Tyr
            500                 505                 510

Val Gly Met Gln Asn Cys Pro Lys Asp Gly Phe Pro Val Pro Ala Asn
        515                 520                 525

Ile Ile Trp His Phe Lys Glu Asp Gly Thr Ile Phe His Pro His Ser
530                 535                 540

Gly Leu Cys Leu Ser Ala Tyr Arg Thr Pro Glu Gly Arg Pro Asp Val
545                 550                 555                 560

Gln Met Arg Thr Cys Asp Ala Leu Asp Lys Asn Gln Ile Trp Ser Phe
                565                 570                 575

Glu Lys

<210> SEQ ID NO 7
<211> LENGTH: 960
<212> TYPE: PRT
<213> ORGANISM: Artificial Sequence
<220> FEATURE:
<223> OTHER INFORMATION: (HA)GalNAc-T2-2A-FWbpP polyprotein which is
      co-translationally spliced into the respective two functional
      proteins, i.e. HA-tagged GalNAc-T2 and N-terminal Flag-tagged WbpP
```

```
<220> FEATURE:
<221> NAME/KEY: 2Aseqence
<222> LOCATION: (581)..(603)

<400> SEQUENCE: 7

Met Tyr Pro Tyr Asp Val Pro Asp Tyr Ala Arg Arg Ser Arg Met
1               5                   10                  15

Leu Leu Cys Phe Ala Phe Leu Trp Val Leu Gly Ile Ala Tyr Tyr Met
            20                  25                  30

Tyr Ser Gly Gly Gly Ser Ala Leu Ala Gly Ala Gly Gly Ala
        35                  40                  45

Gly Arg Lys Glu Asp Trp Asn Glu Ile Asp Pro Ile Lys Lys Lys Asp
50                  55                  60

Leu His His Ser Asn Gly Glu Glu Lys Ala Gln Ser Met Glu Thr Leu
65                  70                  75                  80

Pro Pro Gly Lys Val Arg Trp Pro Asp Phe Asn Gln Glu Ala Tyr Val
                85                  90                  95

Gly Gly Thr Met Val Arg Ser Gly Gln Asp Pro Tyr Ala Arg Asn Lys
            100                 105                 110

Phe Asn Gln Val Glu Ser Asp Lys Leu Arg Met Asp Arg Ala Ile Pro
        115                 120                 125

Asp Thr Arg His Asp Gln Cys Gln Arg Lys Gln Trp Arg Val Asp Leu
130                 135                 140

Pro Ala Thr Ser Val Val Ile Thr Phe His Asn Glu Ala Arg Ser Ala
145                 150                 155                 160

Leu Leu Arg Thr Val Val Ser Val Leu Lys Lys Ser Pro Pro His Leu
                165                 170                 175

Ile Lys Glu Ile Ile Leu Val Asp Asp Tyr Ser Asn Asp Pro Glu Asp
            180                 185                 190

Gly Ala Leu Leu Gly Lys Ile Glu Lys Val Arg Val Leu Arg Asn Asp
        195                 200                 205

Arg Arg Glu Gly Leu Met Arg Ser Arg Val Arg Gly Ala Asp Ala Ala
210                 215                 220

Gln Ala Lys Val Leu Thr Phe Leu Asp Ser His Cys Glu Cys Asn Glu
225                 230                 235                 240

His Trp Leu Glu Pro Leu Leu Glu Arg Val Ala Glu Asp Arg Thr Arg
                245                 250                 255

Val Val Ser Pro Ile Ile Asp Val Ile Asn Met Asp Asn Phe Gln Tyr
            260                 265                 270

Val Gly Ala Ser Ala Asp Leu Lys Gly Gly Phe Asp Trp Asn Leu Val
        275                 280                 285

Phe Lys Trp Asp Tyr Met Thr Pro Glu Gln Arg Arg Ser Arg Gln Gly
290                 295                 300

Asn Pro Val Ala Pro Ile Lys Thr Pro Met Ile Ala Gly Gly Leu Phe
305                 310                 315                 320

Val Met Asp Lys Phe Tyr Phe Glu Glu Leu Gly Lys Tyr Asp Met Met
                325                 330                 335

Met Asp Val Trp Gly Gly Glu Asn Leu Glu Ile Ser Phe Arg Val Trp
            340                 345                 350

Gln Cys Gly Gly Ser Leu Glu Ile Ile Pro Cys Ser Arg Val Gly His
        355                 360                 365

Val Phe Arg Lys Gln His Pro Tyr Thr Phe Pro Gly Gly Ser Gly Thr
370                 375                 380

Val Phe Ala Arg Asn Thr Arg Arg Ala Ala Glu Val Trp Met Asp Glu
```

```
            385                 390                 395                 400
Tyr Lys Asn Phe Tyr Tyr Ala Ala Val Pro Ser Ala Arg Asn Val Pro
                405                 410                 415

Tyr Gly Asn Ile Gln Ser Arg Leu Glu Leu Arg Lys Lys Leu Ser Cys
                420                 425                 430

Lys Pro Phe Lys Trp Tyr Leu Glu Asn Val Tyr Pro Glu Leu Arg Val
                435                 440                 445

Pro Asp His Gln Asp Ile Ala Phe Gly Ala Leu Gln Gln Gly Thr Asn
    450                 455                 460

Cys Leu Asp Thr Leu Gly His Phe Ala Asp Gly Val Val Gly Val Tyr
465                 470                 475                 480

Glu Cys His Asn Ala Gly Gly Asn Gln Glu Trp Ala Leu Thr Lys Glu
                485                 490                 495

Lys Ser Val Lys His Met Asp Leu Cys Leu Thr Val Val Asp Arg Ala
                500                 505                 510

Pro Gly Ser Leu Ile Lys Leu Gln Gly Cys Arg Glu Asn Asp Ser Arg
                515                 520                 525

Gln Lys Trp Glu Gln Ile Glu Gly Asn Ser Lys Leu Arg His Val Gly
    530                 535                 540

Ser Asn Leu Cys Leu Asp Ser Arg Thr Ala Lys Ser Gly Gly Leu Ser
545                 550                 555                 560

Val Glu Val Cys Gly Pro Ala Leu Ser Gln Gln Trp Lys Phe Thr Leu
                565                 570                 575

Asn Leu Gln Gln Gly Ser Gly Gln Thr Leu Asn Phe Asp Leu Leu Lys
                580                 585                 590

Leu Ala Gly Asp Val Glu Ser Asn Pro Gly Pro Met Asp Tyr Lys Asp
                595                 600                 605

Asp Asp Asp Lys His Val Glu Phe Ala Met Val Met Ser Arg Tyr
    610                 615                 620

Glu Glu Leu Arg Lys Glu Leu Pro Ala Gln Pro Lys Val Trp Leu Ile
625                 630                 635                 640

Thr Gly Val Ala Gly Phe Ile Gly Ser Asn Leu Leu Glu Thr Leu Leu
                645                 650                 655

Lys Leu Asp Gln Lys Val Val Gly Leu Asp Asn Phe Ala Thr Gly His
                660                 665                 670

Gln Arg Asn Leu Asp Glu Val Arg Ser Leu Val Ser Glu Lys Gln Trp
                675                 680                 685

Ser Asn Phe Lys Phe Ile Gln Gly Asp Ile Arg Asn Leu Asp Asp Cys
                690                 695                 700

Asn Asn Ala Cys Ala Gly Val Asp Tyr Val Leu His Gln Ala Ala Leu
705                 710                 715                 720

Gly Ser Val Pro Arg Ser Ile Asn Asp Pro Ile Thr Ser Asn Ala Thr
                725                 730                 735

Asn Ile Asp Gly Phe Leu Asn Met Leu Ile Ala Ala Arg Asp Ala Lys
                740                 745                 750

Val Gln Ser Phe Thr Tyr Ala Ala Ser Ser Ser Thr Tyr Gly Asp His
                755                 760                 765

Pro Gly Leu Pro Lys Val Glu Asp Thr Ile Gly Lys Pro Leu Ser Pro
    770                 775                 780

Tyr Ala Val Thr Lys Tyr Val Asn Glu Leu Tyr Ala Asp Val Phe Ser
785                 790                 795                 800

Arg Cys Tyr Gly Phe Ser Thr Ile Gly Leu Arg Tyr Phe Asn Val Phe
                805                 810                 815
```

```
Gly Arg Arg Gln Asp Pro Asn Gly Ala Tyr Ala Val Ile Pro Lys
            820                 825                 830
Trp Thr Ser Ser Met Ile Gln Gly Asp Asp Val Tyr Ile Asn Gly Asp
        835                 840                 845
Gly Glu Thr Ser Arg Asp Phe Cys Tyr Ile Glu Asn Thr Val Gln Ala
850                 855                 860
Asn Leu Leu Ala Ala Thr Ala Gly Leu Asp Ala Arg Asn Gln Val Tyr
865                 870                 875                 880
Asn Ile Ala Val Gly Gly Arg Thr Ser Leu Asn Gln Leu Phe Phe Ala
                885                 890                 895
Leu Arg Asp Gly Leu Ala Glu Asn Gly Val Ser Tyr His Arg Glu Pro
            900                 905                 910
Val Tyr Arg Asp Phe Arg Glu Gly Asp Val Arg His Ser Leu Ala Asp
        915                 920                 925
Ile Ser Lys Ala Ala Lys Leu Leu Gly Tyr Ala Pro Lys Tyr Asp Val
    930                 935                 940
Ser Ala Gly Val Ala Leu Ala Met Pro Trp Tyr Ile Met Phe Leu Lys
945                 950                 955                 960

<210> SEQ ID NO 8
<211> LENGTH: 945
<212> TYPE: PRT
<213> ORGANISM: Artificial Sequence
<220> FEATURE:
<223> OTHER INFORMATION: WbpPF-2A-GalNAc-T2 polyprotein which is
      co-translationally spliced into Golgi localized GalNAc-T2 and
      cytosollic N-terminal Flag-tagged WbpP
<220> FEATURE:
<221> NAME/KEY: 2Asequence
<222> LOCATION: (355)..(374)

<400> SEQUENCE: 8

Met Met Ser Arg Tyr Glu Glu Leu Arg Lys Glu Leu Pro Ala Gln Pro
1               5                   10                  15
Lys Val Trp Leu Ile Thr Gly Val Ala Gly Ser Ile Gly Ser Asn Leu
            20                  25                  30
Leu Glu Thr Leu Leu Lys Leu Asp Gln Lys Val Gly Leu Asp Asn
        35                  40                  45
Phe Ala Thr Gly His Gln Arg Asn Leu Asp Glu Val Arg Ser Leu Ala
    50                  55                  60
Ser Glu Lys Gln Trp Ser Asn Phe Lys Phe Ile Gln Gly Asp Ile Arg
65                  70                  75                  80
Asn Leu Asp Asp Cys Asn Asn Ala Cys Ala Gly Val Asp Tyr Val Leu
                85                  90                  95
His Gln Ala Ala Leu Gly Ser Val Pro Arg Ser Ile Asn Asp Pro Ile
            100                 105                 110
Thr Ser Asn Ala Thr Asn Ile Asp Gly Phe Leu Asn Met Leu Ile Ala
        115                 120                 125
Ala Arg Asp Ala Lys Val Gln Ser Phe Thr Tyr Ala Ala Ser Ser Ser
    130                 135                 140
Thr Tyr Gly Asp His Pro Gly Leu Pro Lys Val Glu Asp Thr Ile Gly
145                 150                 155                 160
Lys Pro Leu Ser Pro Tyr Ala Val Thr Lys Tyr Val Asn Glu Leu Tyr
                165                 170                 175
Ala Asp Val Phe Ser Arg Cys Tyr Gly Phe Ser Thr Ile Gly Leu Arg
            180                 185                 190
```

```
Tyr Phe Asn Val Phe Gly Arg Arg Gln Asp Pro Asn Gly Ala Tyr Ala
            195                 200                 205

Ala Val Ile Pro Lys Trp Thr Ser Ser Met Ile Gln Gly Asp Asp Val
210                 215                 220

Tyr Ile Asn Gly Asp Gly Glu Thr Ser Arg Asp Phe Cys Tyr Ile Glu
225                 230                 235                 240

Asn Thr Val Gln Ala Asn Leu Leu Ala Thr Ala Gly Leu Asp Ala
            245                 250                 255

Arg Asn Gln Val Tyr Asn Ile Ala Val Gly Arg Thr Ser Leu Asn
            260                 265                 270

Gln Leu Phe Phe Ala Leu Arg Asp Gly Leu Ala Glu Asn Gly Val Ser
            275                 280                 285

Tyr His Arg Glu Pro Val Tyr Arg Asp Phe Arg Glu Gly Asp Val Arg
            290                 295                 300

His Ser Leu Ala Asp Ile Ser Lys Ala Ala Lys Leu Leu Gly Tyr Ala
305                 310                 315                 320

Pro Lys Tyr Asp Val Ser Ala Gly Val Ala Leu Ala Met Pro Trp Tyr
                325                 330                 335

Ile Met Phe Leu Lys Asp Tyr Lys Asp Asp Asp Lys Leu Glu Gly
            340                 345                 350

Ser Gly Gln Thr Leu Asn Phe Asp Leu Leu Lys Leu Ala Gly Asp Val
            355                 360                 365

Glu Ser Asn Pro Gly Pro Met Arg Arg Ser Arg Met Leu Leu Cys
            370                 375                 380

Phe Ala Phe Leu Trp Val Leu Gly Ile Ala Tyr Tyr Met Tyr Ser Gly
385                 390                 395                 400

Gly Gly Ser Ala Leu Ala Gly Gly Ala Gly Gly Ala Gly Arg Lys
                405                 410                 415

Glu Asp Trp Asn Glu Ile Asp Pro Ile Lys Lys Lys Asp Leu His His
            420                 425                 430

Ser Asn Gly Glu Glu Lys Ala Gln Ser Met Glu Thr Leu Pro Pro Gly
            435                 440                 445

Lys Val Arg Trp Pro Asp Phe Asn Gln Glu Ala Tyr Val Gly Gly Thr
450                 455                 460

Met Val Arg Ser Gly Gln Asp Pro Tyr Ala Arg Asn Lys Phe Asn Gln
465                 470                 475                 480

Val Glu Ser Asp Lys Leu Arg Met Asp Arg Ala Ile Pro Asp Thr Arg
                485                 490                 495

His Asp Gln Cys Gln Arg Lys Gln Trp Arg Val Asp Leu Pro Ala Thr
            500                 505                 510

Ser Val Val Ile Thr Phe His Asn Glu Ala Arg Ser Ala Leu Leu Arg
            515                 520                 525

Thr Val Val Ser Val Leu Lys Lys Ser Pro Pro His Leu Ile Lys Glu
530                 535                 540

Ile Ile Leu Val Asp Asp Tyr Ser Asn Asp Pro Glu Asp Gly Ala Leu
545                 550                 555                 560

Leu Gly Lys Ile Glu Lys Val Arg Val Leu Arg Asn Asp Arg Arg Glu
                565                 570                 575

Gly Leu Met Arg Ser Arg Val Arg Gly Ala Asp Ala Ala Gln Ala Lys
            580                 585                 590

Val Leu Thr Phe Leu Asp Ser His Cys Glu Cys Asn Glu His Trp Leu
            595                 600                 605

Glu Pro Leu Leu Glu Arg Val Ala Glu Asp Arg Thr Arg Val Val Ser
```

Pro Ile Ile Asp Val Ile Asn Met Asp Asn Phe Gln Tyr Val Gly Ala
625                 630                 635                 640

Ser Ala Asp Leu Lys Gly Gly Phe Asp Trp Asn Leu Val Phe Lys Trp
            645                 650                 655

Asp Tyr Met Thr Pro Glu Gln Arg Ser Arg Gln Gly Asn Pro Val
                660                 665                 670

Ala Pro Ile Lys Thr Pro Met Ile Ala Gly Gly Leu Phe Val Met Asp
            675                 680                 685

Lys Phe Tyr Phe Glu Glu Leu Gly Lys Tyr Asp Met Met Met Asp Val
690                 695                 700

Trp Gly Gly Glu Asn Leu Glu Ile Ser Phe Arg Val Trp Gln Cys Gly
705                 710                 715                 720

Gly Ser Leu Glu Ile Ile Pro Cys Ser Arg Val Gly His Val Phe Arg
                725                 730                 735

Lys Gln His Pro Tyr Thr Phe Pro Gly Gly Ser Gly Thr Val Phe Ala
                740                 745                 750

Arg Asn Thr Arg Arg Ala Ala Glu Val Trp Met Asp Glu Tyr Lys Asn
            755                 760                 765

Phe Tyr Tyr Ala Ala Val Pro Ser Ala Arg Asn Val Pro Tyr Gly Asn
770                 775                 780

Ile Gln Ser Arg Leu Glu Leu Arg Lys Lys Leu Ser Cys Lys Pro Phe
785                 790                 795                 800

Lys Trp Tyr Leu Glu Asn Val Tyr Pro Glu Leu Arg Val Pro Asp His
                805                 810                 815

Gln Asp Ile Ala Phe Gly Ala Leu Gln Gln Gly Thr Asn Cys Leu Asp
                820                 825                 830

Thr Leu Gly His Phe Ala Asp Gly Val Val Gly Val Tyr Glu Cys His
            835                 840                 845

Asn Ala Gly Gly Asn Gln Glu Trp Ala Leu Thr Lys Glu Lys Ser Val
850                 855                 860

Lys His Met Asp Leu Cys Leu Thr Val Val Asp Arg Ala Pro Gly Ser
865                 870                 875                 880

Leu Ile Lys Leu Gln Gly Cys Arg Glu Asn Asp Ser Arg Gln Lys Trp
                885                 890                 895

Glu Gln Ile Glu Gly Asn Ser Lys Leu Arg His Val Gly Ser Asn Leu
                900                 905                 910

Cys Leu Asp Ser Arg Thr Ala Lys Ser Gly Gly Leu Ser Val Glu Val
            915                 920                 925

Cys Gly Pro Ala Leu Ser Gln Gln Trp Lys Phe Thr Leu Asn Leu Gln
930                 935                 940

Gln
945

<210> SEQ ID NO 9
<211> LENGTH: 951
<212> TYPE: PRT
<213> ORGANISM: Artificial Sequence
<220> FEATURE:
<223> OTHER INFORMATION: GalNAc-T2-2A-FWbpP polyprotein which is
      co-translationally spliced into Golgi Localized GalNAc-T2 and
      cytosolic N-terminal Flag-tagged WbpP

<400> SEQUENCE: 9

Met Arg Arg Arg Ser Arg Met Leu Leu Cys Phe Ala Phe Leu Trp Val
1               5                   10                  15

-continued

Leu Gly Ile Ala Tyr Tyr Met Tyr Ser Gly Gly Ser Ala Leu Ala
         20                  25                  30

Gly Gly Ala Gly Gly Ala Gly Arg Lys Glu Asp Trp Asn Glu Ile
         35                  40                  45

Asp Pro Ile Lys Lys Asp Leu His His Ser Asn Gly Glu Glu Lys
 50                  55                  60

Ala Gln Ser Met Glu Thr Leu Pro Pro Gly Lys Val Arg Trp Pro Asp
 65                  70                  75                  80

Phe Asn Gln Glu Ala Tyr Val Gly Gly Thr Met Val Arg Ser Gly Gln
                     85                  90                  95

Asp Pro Tyr Ala Arg Asn Lys Phe Asn Gln Val Glu Ser Asp Lys Leu
             100                 105                 110

Arg Met Asp Arg Ala Ile Pro Asp Thr Arg His Asp Gln Cys Gln Arg
             115                 120                 125

Lys Gln Trp Arg Val Asp Leu Pro Ala Thr Ser Val Ile Thr Phe
 130                 135                 140

His Asn Glu Ala Arg Ser Ala Leu Leu Arg Thr Val Val Ser Val Leu
 145                 150                 155                 160

Lys Lys Ser Pro Pro His Leu Ile Lys Glu Ile Ile Leu Val Asp Asp
                 165                 170                 175

Tyr Ser Asn Asp Pro Glu Asp Gly Ala Leu Leu Gly Lys Ile Glu Lys
                 180                 185                 190

Val Arg Val Leu Arg Asn Asp Arg Arg Glu Gly Leu Met Arg Ser Arg
         195                 200                 205

Val Arg Gly Ala Asp Ala Ala Gln Ala Lys Val Leu Thr Phe Leu Asp
 210                 215                 220

Ser His Cys Glu Cys Asn Glu His Trp Leu Glu Pro Leu Leu Glu Arg
 225                 230                 235                 240

Val Ala Glu Asp Arg Thr Arg Val Val Ser Pro Ile Ile Asp Val Ile
                 245                 250                 255

Asn Met Asp Asn Phe Gln Tyr Val Gly Ala Ser Ala Asp Leu Lys Gly
                 260                 265                 270

Gly Phe Asp Trp Asn Leu Val Phe Lys Trp Asp Tyr Met Thr Pro Glu
         275                 280                 285

Gln Arg Arg Ser Arg Gln Gly Asn Pro Val Ala Pro Ile Lys Thr Pro
         290                 295                 300

Met Ile Ala Gly Gly Leu Phe Val Met Asp Lys Phe Tyr Phe Glu Glu
 305                 310                 315                 320

Leu Gly Lys Tyr Asp Met Met Met Asp Val Trp Gly Gly Glu Asn Leu
                 325                 330                 335

Glu Ile Ser Phe Arg Val Trp Gln Cys Gly Gly Ser Leu Glu Ile Ile
                 340                 345                 350

Pro Cys Ser Arg Val Gly His Val Phe Arg Lys Gln His Pro Tyr Thr
         355                 360                 365

Phe Pro Gly Gly Ser Gly Thr Val Phe Ala Arg Asn Thr Arg Arg Ala
         370                 375                 380

Ala Glu Val Trp Met Asp Glu Tyr Lys Asn Phe Tyr Tyr Ala Ala Val
 385                 390                 395                 400

Pro Ser Ala Arg Asn Val Pro Tyr Gly Asn Ile Gln Ser Arg Leu Glu
                 405                 410                 415

Leu Arg Lys Lys Leu Ser Cys Lys Pro Phe Lys Trp Tyr Leu Glu Asn
                 420                 425                 430

-continued

```
Val Tyr Pro Glu Leu Arg Val Pro Asp His Gln Asp Ile Ala Phe Gly
            435                 440                 445

Ala Leu Gln Gln Gly Thr Asn Cys Leu Asp Thr Leu Gly His Phe Ala
450                 455                 460

Asp Gly Val Val Gly Val Tyr Glu Cys His Asn Ala Gly Gly Asn Gln
465                 470                 475                 480

Glu Trp Ala Leu Thr Lys Glu Lys Ser Val Lys His Met Asp Leu Cys
                485                 490                 495

Leu Thr Val Val Asp Arg Ala Pro Gly Ser Leu Ile Lys Leu Gln Gly
            500                 505                 510

Cys Arg Glu Asn Asp Ser Arg Gln Lys Trp Glu Gln Ile Glu Gly Asn
        515                 520                 525

Ser Lys Leu Arg His Val Gly Ser Asn Leu Cys Leu Asp Ser Arg Thr
    530                 535                 540

Ala Lys Ser Gly Gly Leu Ser Val Glu Val Cys Gly Pro Ala Leu Ser
545                 550                 555                 560

Gln Gln Trp Lys Phe Thr Leu Asn Leu Gln Gln Gly Ser Gly Gln Thr
                565                 570                 575

Leu Asn Phe Asp Leu Leu Lys Leu Ala Gly Asp Val Glu Ser Asn Pro
            580                 585                 590

Gly Pro Met Asp Tyr Lys Asp Asp Asp Lys His Val Glu Phe Ala
        595                 600                 605

Met Val Met Met Ser Arg Tyr Glu Glu Leu Arg Lys Glu Leu Pro Ala
    610                 615                 620

Gln Pro Lys Val Trp Leu Ile Thr Gly Val Ala Gly Phe Ile Gly Ser
625                 630                 635                 640

Asn Leu Leu Glu Thr Leu Leu Lys Leu Asp Gln Lys Val Val Gly Leu
                645                 650                 655

Asp Asn Phe Ala Thr Gly His Gln Arg Asn Leu Asp Glu Val Arg Ser
            660                 665                 670

Leu Val Ser Glu Lys Gln Trp Ser Asn Phe Lys Phe Ile Gln Gly Asp
        675                 680                 685

Ile Arg Asn Leu Asp Asp Cys Asn Asn Ala Cys Ala Gly Val Asp Tyr
    690                 695                 700

Val Leu His Gln Ala Ala Leu Gly Ser Val Pro Arg Ser Ile Asn Asp
705                 710                 715                 720

Pro Ile Thr Ser Asn Ala Thr Asn Ile Asp Gly Phe Leu Asn Met Leu
                725                 730                 735

Ile Ala Ala Arg Asp Ala Lys Val Gln Ser Phe Thr Tyr Ala Ala Ser
            740                 745                 750

Ser Ser Thr Tyr Gly Asp His Pro Gly Leu Pro Lys Val Glu Asp Thr
        755                 760                 765

Ile Gly Lys Pro Leu Ser Pro Tyr Ala Val Thr Lys Tyr Val Asn Glu
    770                 775                 780

Leu Tyr Ala Asp Val Phe Ser Arg Cys Tyr Gly Phe Ser Thr Ile Gly
785                 790                 795                 800

Leu Arg Tyr Phe Asn Val Phe Gly Arg Arg Gln Asp Pro Asn Gly Ala
                805                 810                 815

Tyr Ala Ala Val Ile Pro Lys Trp Thr Ser Ser Met Ile Gln Gly Asp
            820                 825                 830

Asp Val Tyr Ile Asn Gly Asp Gly Glu Thr Ser Arg Asp Phe Cys Tyr
        835                 840                 845

Ile Glu Asn Thr Val Gln Ala Asn Leu Leu Ala Ala Thr Ala Gly Leu
```

```
                850                 855                 860
Asp Ala Arg Asn Gln Val Tyr Asn Ile Ala Val Gly Gly Arg Thr Ser
865                 870                 875                 880

Leu Asn Gln Leu Phe Phe Ala Leu Arg Asp Gly Leu Ala Glu Asn Gly
                    885                 890                 895

Val Ser Tyr His Arg Glu Pro Val Tyr Arg Asp Phe Arg Glu Gly Asp
                900                 905                 910

Val Arg His Ser Leu Ala Asp Ile Ser Lys Ala Lys Leu Leu Gly
            915                 920                 925

Tyr Ala Pro Lys Tyr Asp Val Ser Ala Gly Val Ala Leu Ala Met Pro
        930                 935                 940

Trp Tyr Ile Met Phe Leu Lys
945                 950

<210> SEQ ID NO 10
<211> LENGTH: 74
<212> TYPE: DNA
<213> ORGANISM: Artificial Sequence
<220> FEATURE:
<223> OTHER INFORMATION: PBY7For primer

<400> SEQUENCE: 10
gagctcatgg attacaagga cgacgacgac aagcacgtgg aattcgccat ggttatgatg   60
agtcgttatg aaga                                                    74

<210> SEQ ID NO 11
<211> LENGTH: 1083
<212> TYPE: PRT
<213> ORGANISM: Artificial Sequence
<220> FEATURE:
<223> OTHER INFORMATION: FT2GolWbpP-2A-T2 polyprotein which is
      co-translationally spliced into Golgi localized N-terminal Flag
      tagged WbpP and GalNAc-T2
<220> FEATURE:
<221> NAME/KEY: 2Asequence
<222> LOCATION: (493)..(512)

<400> SEQUENCE: 11

Met Asp Tyr Lys Asp Asp Asp Asp Lys Arg Arg Arg Ser Arg Met Leu
1               5                   10                  15

Leu Cys Phe Ala Phe Leu Trp Val Leu Gly Ile Ala Tyr Tyr Met Tyr
            20                  25                  30

Ser Gly Gly Gly Ser Ala Leu Ala Gly Gly Ala Gly Gly Ala Gly
        35                  40                  45

Arg Lys Glu Asp Trp Asn Glu Ile Asp Pro Ile Lys Lys Asp Leu
    50                  55                  60

His His Ser Asn Gly Glu Glu Lys Ala Gln Ser Met Glu Thr Leu Pro
65                  70                  75                  80

Pro Gly Lys Val Arg Trp Pro Asp Phe Asn Gln Glu Ala Tyr Val Gly
                85                  90                  95

Gly Thr Met Val Arg Ser Gly Gln Asp Pro Tyr Ala Arg Asn Lys Phe
            100                 105                 110

Asn Gln Val Glu Ser Asp Lys Leu Arg Met Asp Arg Ala Ile Pro Asp
        115                 120                 125

Thr Arg His Asp Gln Cys Gln Arg Lys Gln Trp Arg Val Asp Leu Pro
    130                 135                 140

Ala Thr Met Met Ser Arg Tyr Glu Glu Leu Arg Lys Glu Leu Pro Ala
145                 150                 155                 160
```

```
Gln Pro Lys Val Trp Leu Ile Thr Gly Val Ala Gly Ser Ile Gly Ser
                165                 170                 175

Asn Leu Leu Glu Thr Leu Leu Lys Leu Asp Gln Lys Val Val Gly Leu
        180                 185                 190

Asp Asn Phe Ala Thr Gly His Gln Arg Asn Leu Asp Glu Val Arg Ser
        195                 200                 205

Leu Ala Ser Glu Lys Gln Trp Ser Asn Phe Lys Phe Ile Gln Gly Asp
        210                 215                 220

Ile Arg Asn Leu Asp Asp Cys Asn Asn Ala Cys Ala Gly Val Asp Tyr
225                 230                 235                 240

Val Leu His Gln Ala Ala Leu Gly Ser Val Pro Arg Ser Ile Asn Asp
                245                 250                 255

Pro Ile Thr Ser Asn Ala Thr Asn Ile Asp Gly Phe Leu Asn Met Leu
                260                 265                 270

Ile Ala Ala Arg Asp Ala Lys Val Gln Ser Phe Thr Tyr Ala Ala Ser
                275                 280                 285

Ser Ser Thr Tyr Gly Asp His Pro Gly Leu Pro Lys Val Glu Asp Thr
        290                 295                 300

Ile Gly Lys Pro Leu Ser Pro Tyr Ala Val Thr Lys Tyr Val Asn Glu
305                 310                 315                 320

Leu Tyr Ala Asp Val Phe Ser Arg Cys Tyr Gly Phe Ser Thr Ile Gly
                325                 330                 335

Leu Arg Tyr Phe Asn Val Phe Gly Arg Arg Gln Asp Pro Asn Gly Ala
                340                 345                 350

Tyr Ala Ala Val Ile Pro Lys Trp Thr Ser Ser Met Ile Gln Gly Asp
        355                 360                 365

Asp Val Tyr Ile Asn Gly Asp Gly Glu Thr Ser Arg Asp Phe Cys Tyr
        370                 375                 380

Ile Glu Asn Thr Val Gln Ala Asn Leu Leu Ala Ala Thr Ala Gly Leu
385                 390                 395                 400

Asp Ala Arg Asn Gln Val Tyr Asn Ile Ala Val Gly Gly Arg Thr Ser
                405                 410                 415

Leu Asn Gln Leu Phe Phe Ala Leu Arg Asp Gly Leu Ala Glu Asn Gly
                420                 425                 430

Val Ser Tyr His Arg Glu Pro Val Tyr Arg Asp Phe Arg Glu Gly Asp
        435                 440                 445

Val Arg His Ser Leu Ala Asp Ile Ser Lys Ala Ala Lys Leu Leu Gly
        450                 455                 460

Tyr Ala Pro Lys Tyr Asp Val Ser Ala Gly Val Ala Leu Ala Met Pro
465                 470                 475                 480

Trp Tyr Ile Met Phe Leu Lys Leu Glu Gly Ser Gly Gln Thr Leu Asn
                485                 490                 495

Phe Asp Leu Leu Lys Leu Ala Gly Asp Val Glu Ser Asn Pro Gly Pro
                500                 505                 510

Met Arg Arg Arg Ser Arg Met Leu Leu Cys Phe Ala Phe Leu Trp Val
        515                 520                 525

Leu Gly Ile Ala Tyr Tyr Met Tyr Ser Gly Gly Ser Ala Leu Ala
        530                 535                 540

Gly Gly Ala Gly Gly Ala Gly Arg Lys Glu Asp Trp Asn Glu Ile
545                 550                 555                 560

Asp Pro Ile Lys Lys Lys Asp Leu His His Ser Asn Gly Glu Glu Lys
                565                 570                 575

Ala Gln Ser Met Glu Thr Leu Pro Pro Gly Lys Val Arg Trp Pro Asp
```

-continued

```
            580             585             590
Phe Asn Gln Glu Ala Tyr Val Gly Gly Thr Met Val Arg Ser Gly Gln
            595             600             605

Asp Pro Tyr Ala Arg Asn Lys Phe Asn Gln Val Glu Ser Asp Lys Leu
            610             615             620

Arg Met Asp Arg Ala Ile Pro Asp Thr Arg His Asp Gln Cys Gln Arg
625             630             635             640

Lys Gln Trp Arg Val Asp Leu Pro Ala Thr Ser Val Val Ile Thr Phe
            645             650             655

His Asn Glu Ala Arg Ser Ala Leu Leu Arg Thr Val Val Ser Val Leu
            660             665             670

Lys Lys Ser Pro Pro His Leu Ile Lys Glu Ile Ile Leu Val Asp Asp
            675             680             685

Tyr Ser Asn Asp Pro Glu Asp Gly Ala Leu Leu Gly Lys Ile Glu Lys
            690             695             700

Val Arg Val Leu Arg Asn Asp Arg Arg Glu Gly Leu Met Arg Ser Arg
705             710             715             720

Val Arg Gly Ala Asp Ala Ala Gln Ala Lys Val Leu Thr Phe Leu Asp
            725             730             735

Ser His Cys Glu Cys Asn Glu His Trp Leu Glu Pro Leu Leu Glu Arg
            740             745             750

Val Ala Glu Asp Arg Thr Arg Val Val Ser Pro Ile Ile Asp Val Ile
            755             760             765

Asn Met Asp Asn Phe Gln Tyr Val Gly Ala Ser Ala Asp Leu Lys Gly
            770             775             780

Gly Phe Asp Trp Asn Leu Val Phe Lys Trp Asp Tyr Met Thr Pro Glu
785             790             795             800

Gln Arg Arg Ser Arg Gln Gly Asn Pro Val Ala Pro Ile Lys Thr Pro
            805             810             815

Met Ile Ala Gly Gly Leu Phe Val Met Asp Lys Phe Tyr Phe Glu Glu
            820             825             830

Leu Gly Lys Tyr Asp Met Met Met Asp Val Trp Gly Gly Glu Asn Leu
            835             840             845

Glu Ile Ser Phe Arg Val Trp Gln Cys Gly Gly Ser Leu Glu Ile Ile
            850             855             860

Pro Cys Ser Arg Val Gly His Val Phe Arg Lys Gln His Pro Tyr Thr
865             870             875             880

Phe Pro Gly Gly Ser Gly Thr Val Phe Ala Arg Asn Thr Arg Arg Ala
            885             890             895

Ala Glu Val Trp Met Asp Glu Tyr Lys Asn Phe Tyr Tyr Ala Ala Val
            900             905             910

Pro Ser Ala Arg Asn Val Pro Tyr Gly Asn Ile Gln Ser Arg Leu Glu
            915             920             925

Leu Arg Lys Lys Leu Ser Cys Lys Pro Phe Lys Trp Tyr Leu Glu Asn
            930             935             940

Val Tyr Pro Glu Leu Arg Val Pro Asp His Gln Asp Ile Ala Phe Gly
945             950             955             960

Ala Leu Gln Gln Gly Thr Asn Cys Leu Asp Thr Leu Gly His Phe Ala
            965             970             975

Asp Gly Val Val Gly Val Tyr Glu Cys His Asn Ala Gly Gly Asn Gln
            980             985             990

Glu Trp Ala Leu Thr Lys Glu Lys  Ser Val Lys His Met  Asp Leu Cys
            995             1000             1005
```

Leu Thr Val Val Asp Arg Ala Pro Gly Ser Leu Ile Lys Leu Gln
        1010                1015                1020

Gly Cys Arg Glu Asn Asp Ser Arg Gln Lys Trp Glu Gln Ile Glu
        1025                1030                1035

Gly Asn Ser Lys Leu Arg His Val Gly Ser Asn Leu Cys Leu Asp
        1040                1045                1050

Ser Arg Thr Ala Lys Ser Gly Gly Leu Ser Val Glu Val Cys Gly
        1055                1060                1065

Pro Ala Leu Ser Gln Gln Trp Lys Phe Thr Leu Asn Leu Gln Gln
        1070                1075                1080

<210> SEQ ID NO 12
<211> LENGTH: 39
<212> TYPE: DNA
<213> ORGANISM: Artificial Sequence
<220> FEATURE:
<223> OTHER INFORMATION: PBY7Rev primer

<400> SEQUENCE: 12
agcgctaggc ctgagctctc atttcaaaaa catgatgta                              39

<210> SEQ ID NO 13
<211> LENGTH: 144
<212> TYPE: PRT
<213> ORGANISM: Artificial Sequence
<220> FEATURE:
<223> OTHER INFORMATION: MUC1-3.5TR with C-terminal glycomodule (SP)10
      and N-terminal OsSP secretion peptide sequence

<400> SEQUENCE: 13

Met Ala Lys His Ser Thr Thr Met Ser Cys Leu Leu Phe Phe Val Leu
1               5                   10                  15

Leu Cys Leu Gly Ser His Leu Ala Gln Ala His Met Val Thr Ser Ala
            20                  25                  30

Pro Asp Thr Arg Pro Ala Pro Gly Ser Thr Ala Pro Pro Ala His Gly
        35                  40                  45

Val Thr Ser Ala Pro Asp Thr Arg Pro Ala Pro Gly Ser Thr Ala Pro
    50                  55                  60

Pro Ala His Gly Val Thr Ser Ala Pro Asp Thr Arg Pro Ala Pro Gly
65                  70                  75                  80

Ser Thr Ala Pro Pro Ala His Gly Val Thr Ser Ala Pro Asp Thr Leu
                85                  90                  95

Val Pro Arg Gly Ser Met Ala Ser Met Thr Gly Gly Gln Gln Met Gly
            100                 105                 110

Leu Ile Asn Ser Pro Ser Pro Ser Pro Ser Pro Ser Pro Ser Pro Ser
        115                 120                 125

Pro Ser Pro Ser Pro Ser Pro Leu Ile Asn His His His His His His
    130                 135                 140

<210> SEQ ID NO 14
<211> LENGTH: 124
<212> TYPE: PRT
<213> ORGANISM: Artificial Sequence
<220> FEATURE:
<223> OTHER INFORMATION: MUC1-3.5TR with N-terminal OsSP secretion
      signal peptide

<400> SEQUENCE: 14

Met Ala Lys His Ser Thr Thr Met Ser Cys Leu Leu Phe Phe Val Leu
1               5                   10                  15

```
Leu Cys Leu Gly Ser His Leu Ala Gln Ala His Met Val Thr Ser Ala
            20                  25                  30

Pro Asp Thr Arg Pro Ala Pro Gly Ser Thr Ala Pro Ala His Gly
        35                  40                  45

Val Thr Ser Ala Pro Asp Thr Arg Pro Ala Pro Gly Ser Thr Ala Pro
 50                  55                  60

Pro Ala His Gly Val Thr Ser Ala Pro Asp Thr Arg Pro Ala Pro Gly
 65                  70                  75                  80

Ser Thr Ala Pro Pro Ala His Gly Val Thr Ser Ala Pro Asp Thr Leu
                85                  90                  95

Val Pro Arg Gly Ser Met Ala Ser Met Thr Gly Gly Gln Gln Met Gly
            100                 105                 110

Leu Ile Asn Leu Ile Asn His His His His His His
            115                 120
```

`<210>` SEQ ID NO 15
`<211>` LENGTH: 121
`<212>` TYPE: PRT
`<213>` ORGANISM: Artificial Sequence
`<220>` FEATURE:
`<223>` OTHER INFORMATION: MUC1-3.5TR with N-terminal His tag and
    N-terminal OsSP secretion peptide sequence

`<400>` SEQUENCE: 15

```
Met Ala Lys His Ser Thr Thr Met Ser Cys Leu Leu Phe Phe Val Leu
 1               5                  10                  15

Leu Cys Leu Gly Ser His Leu Ala Gln Ala His Met His His His His
            20                  25                  30

His His Leu Ile Asn Met Ala Ser Met Thr Gly Gly Gln Gln Met Gly
        35                  40                  45

Leu Val Pro Arg Gly Ser Val Thr Ser Ala Pro Asp Thr Arg Pro Ala
 50                  55                  60

Pro Gly Ser Thr Ala Pro Pro Ala His Gly Val Thr Ser Ala Pro Asp
 65                  70                  75                  80

Thr Arg Pro Ala Pro Gly Ser Thr Ala Pro Pro Ala His Gly Val Thr
            85                  90                  95

Ser Ala Pro Asp Thr Arg Pro Ala Pro Gly Ser Thr Ala Pro Pro Ala
            100                 105                 110

His Gly Val Thr Ser Ala Pro Asp Thr
        115                 120
```

`<210>` SEQ ID NO 16
`<211>` LENGTH: 185
`<212>` TYPE: PRT
`<213>` ORGANISM: Artificial Sequence
`<220>` FEATURE:
`<223>` OTHER INFORMATION: Podoplanin (hPod) with N-terminal glycomodule
    and N-terminal OsSP signal sequence

`<400>` SEQUENCE: 16

```
Met Ala Lys His Ser Thr Thr Met Ser Cys Leu Leu Phe Phe Val Leu
 1               5                  10                  15

Leu Cys Leu Gly Ser His Leu Ala Gln Ala Gly Ala Pro His His His
            20                  25                  30

His His His Thr Arg Ser Pro Ser Pro Ser Pro Ser Pro Ser Pro Ser
        35                  40                  45

Pro Ser Pro Ser Pro Ser Pro Thr Arg Met Ala Ser Met Thr
 50                  55                  60
```

Gly Gly Gln Gln Met Gly Leu Val Pro Arg Gly Ser Gly Ser Gly Ala
65                  70                  75                  80

Ser Thr Gly Gln Pro Glu Asp Asp Thr Glu Thr Thr Gly Leu Glu Gly
                85                  90                  95

Gly Val Ala Met Pro Gly Ala Glu Asp Asp Val Val Thr Pro Gly Thr
            100                 105                 110

Ser Glu Asp Arg Tyr Lys Ser Gly Leu Thr Thr Leu Val Ala Thr Ser
            115                 120                 125

Val Asn Ser Val Thr Gly Ile Arg Ile Glu Asp Leu Pro Thr Ser Glu
    130                 135                 140

Ser Thr Val His Ala Gln Glu Gln Ser Pro Ser Ala Thr Ala Ser Asn
145                 150                 155                 160

Val Ala Thr Ser His Ser Thr Glu Lys Val Asp Gly Asp Gln Thr Thr
                165                 170                 175

Val Glu Lys Asp Gly Leu Ser Thr Val
            180                 185

<210> SEQ ID NO 17
<211> LENGTH: 347
<212> TYPE: PRT
<213> ORGANISM: Artificial Sequence
<220> FEATURE:
<223> OTHER INFORMATION: MUC1-3.5TR N-terminally fused to YFP

<400> SEQUENCE: 17

Met Gly Ala Ser Arg Ser Val Arg Leu Ala Phe Phe Leu Val Val Leu
1               5                   10                  15

Val Val Leu Ala Ala Leu Ala Glu Ala Val Thr Ser Ala Pro Asp Thr
            20                  25                  30

Arg Pro Ala Pro Gly Ser Thr Ala Pro Ala His Gly Val Thr Ser
        35                  40                  45

Ala Pro Asp Thr Arg Pro Ala Pro Gly Ser Thr Ala Pro Pro Ala His
    50                  55                  60

Gly Val Thr Ser Ala Pro Asp Thr Arg Pro Ala Pro Gly Ser Thr Ala
65                  70                  75                  80

Pro Pro Ala His Gly Val Thr Ser Ala Pro Asp Thr Val Leu Asn Leu
                85                  90                  95

Ser Leu Gly Ser Gly Gly Met Val Ser Lys Gly Glu Glu Leu Phe Thr
            100                 105                 110

Gly Val Val Pro Ile Leu Val Glu Leu Asp Gly Asp Val Asn Gly His
            115                 120                 125

Lys Phe Ser Val Ser Gly Glu Gly Glu Gly Asp Ala Thr Tyr Gly Lys
    130                 135                 140

Leu Thr Leu Lys Leu Ile Cys Thr Thr Gly Lys Leu Pro Val Pro Trp
145                 150                 155                 160

Pro Thr Leu Val Thr Thr Leu Gly Tyr Gly Leu Gln Cys Phe Ala Arg
                165                 170                 175

Tyr Pro Asp His Met Lys Gln His Asp Phe Phe Lys Ser Ala Met Pro
            180                 185                 190

Glu Gly Tyr Val Gln Glu Arg Thr Ile Phe Phe Lys Asp Asp Gly Asn
            195                 200                 205

Tyr Lys Thr Arg Ala Glu Val Lys Phe Glu Gly Asp Thr Leu Val Asn
    210                 215                 220

Arg Ile Glu Leu Lys Gly Ile Asp Phe Lys Glu Asp Gly Asn Ile Leu
225                 230                 235                 240

```
Gly His Lys Leu Glu Tyr Asn Tyr Asn Ser His Asn Val Tyr Ile Thr
            245                 250                 255

Ala Asp Lys Gln Lys Asn Gly Ile Lys Ala Asn Phe Lys Ile Arg His
            260                 265                 270

Asn Ile Glu Asp Gly Gly Val Gln Leu Ala Asp His Tyr Gln Gln Asn
            275                 280                 285

Thr Pro Ile Gly Asp Gly Pro Val Leu Leu Pro Asp Asn His Tyr Leu
            290                 295                 300

Ser Tyr Gln Ser Ala Leu Ser Lys Asp Pro Asn Glu Lys Arg Asp His
305                 310                 315                 320

Met Val Leu Leu Glu Phe Val Thr Ala Ala Gly Ile Thr Leu Gly Met
                325                 330                 335

Asp Glu Leu Tyr Lys His His His His His His
            340                 345

<210> SEQ ID NO 18
<211> LENGTH: 359
<212> TYPE: PRT
<213> ORGANISM: Artificial Sequence
<220> FEATURE:
<223> OTHER INFORMATION: MUC1-3.5TR C-terminally fused to YFP

<400> SEQUENCE: 18

Met Gly Lys Thr Asn Leu Phe Leu Phe Leu Ile Phe Ser Leu Leu Leu
1               5                   10                  15

Ser Leu Ser Ser Ala Glu Gln Val Ser Lys Gly Glu Glu Leu Phe Thr
            20                  25                  30

Gly Val Val Pro Ile Leu Val Glu Leu Asp Gly Asp Val Asn Gly His
            35                  40                  45

Lys Phe Ser Val Ser Gly Glu Gly Glu Gly Asp Ala Thr Tyr Gly Lys
        50                  55                  60

Leu Thr Leu Lys Leu Ile Cys Thr Thr Gly Lys Leu Pro Val Pro Trp
65                  70                  75                  80

Pro Thr Leu Val Thr Thr Leu Gly Tyr Gly Leu Gln Cys Phe Ala Arg
                85                  90                  95

Tyr Pro Asp His Met Lys Gln His Asp Phe Phe Lys Ser Ala Met Pro
            100                 105                 110

Glu Gly Tyr Val Gln Glu Arg Thr Ile Phe Phe Lys Asp Asp Gly Asn
            115                 120                 125

Tyr Lys Thr Arg Ala Glu Val Lys Phe Glu Gly Asp Thr Leu Val Asn
        130                 135                 140

Arg Ile Glu Leu Lys Gly Ile Asp Phe Lys Glu Asp Gly Asn Ile Leu
145                 150                 155                 160

Gly His Lys Leu Glu Tyr Asn Tyr Asn Ser His Asn Val Tyr Ile Thr
                165                 170                 175

Ala Asp Lys Gln Lys Asn Gly Ile Lys Ala Asn Phe Lys Ile Arg His
            180                 185                 190

Asn Ile Glu Asp Gly Gly Val Gln Leu Ala Asp His Tyr Gln Gln Asn
            195                 200                 205

Thr Pro Ile Gly Asp Gly Pro Val Leu Leu Pro Asp Asn His Tyr Leu
        210                 215                 220

Ser Tyr Gln Ser Ala Leu Ser Lys Asp Pro Asn Glu Lys Arg Asp His
225                 230                 235                 240

Met Val Leu Leu Glu Phe Val Thr Ala Ala Gly Ile Thr Leu Gly Met
                245                 250                 255
```

```
Asp Glu Leu Tyr Lys His Met Val Thr Ser Ala Pro Asp Thr Arg Pro
            260                 265                 270

Ala Pro Gly Ser Thr Ala Pro Ala His Gly Val Thr Ser Ala Pro
        275                 280                 285

Asp Thr Arg Pro Ala Pro Gly Ser Thr Ala Pro Ala His Gly Val
        290                 295                 300

Thr Ser Ala Pro Asp Thr Arg Pro Ala Pro Gly Ser Thr Ala Pro Pro
305                 310                 315                 320

Ala His Gly Val Thr Ser Ala Pro Asp Thr Leu Val Pro Arg Gly Ser
                325                 330                 335

Met Ala Ser Met Thr Gly Gly Gln Gln Met Gly Leu Ile Asn Leu Ile
            340                 345                 350

Asn His His His His His His
            355

<210> SEQ ID NO 19
<211> LENGTH: 238
<212> TYPE: PRT
<213> ORGANISM: Artificial Sequence
<220> FEATURE:
<223> OTHER INFORMATION: Interferon A2 B with C-terminal glycomodule

<400> SEQUENCE: 19

Met Gly Lys Met Ala Ser Leu Phe Ala Thr Phe Leu Val Val Leu Val
1               5                   10                  15

Ser Leu Ser Leu Ala Gln Thr Gly Ala Pro Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu Gln Glu Ser Leu Arg Ser Lys Glu Leu
            180                 185                 190

Val Pro Arg Gly Ser Met Ala Ser Met Thr Gly Gly Gln Gln Met Gly
        195                 200                 205

Thr Arg Ser Pro Ser Pro Ser Pro Ser Pro Ser Pro Ser Pro Ser Pro
    210                 215                 220

Ser Pro Ser Pro Ser Pro Thr Arg His His His His His
225                 230                 235

<210> SEQ ID NO 20
```

<211> LENGTH: 343
<212> TYPE: PRT
<213> ORGANISM: Artificial Sequence
<220> FEATURE:
<223> OTHER INFORMATION: MUC1-2TR with His tag embedded in GFP

<400> SEQUENCE: 20

```
Met Gly Lys Thr Asn Leu Phe Leu Phe Leu Ile Phe Ser Leu Leu Leu
1               5                   10                  15
Ser Leu Ser Ser Ala Glu Gln Val Ser Lys Gly Glu Glu Leu Phe Thr
            20                  25                  30
Gly Val Val Pro Ile Leu Val Glu Leu Asp Gly Asp Val Asn Gly His
        35                  40                  45
Lys Phe Ser Val Ser Gly Glu Gly Glu Gly Asp Ala Thr Tyr Gly Lys
    50                  55                  60
Leu Thr Leu Lys Phe Ile Cys Thr Thr Gly Lys Leu Pro Val Pro Trp
65                  70                  75                  80
Pro Thr Leu Val Thr Thr Leu Thr Tyr Gly Val Gln Cys Phe Ser Arg
                85                  90                  95
Tyr Pro Asp His Met Lys Gln His Asp Phe Phe Lys Ser Ala Met Pro
            100                 105                 110
Glu Gly Tyr Val Gln Glu Arg Thr Ile Phe Phe Lys Asp Asp Gly Asn
        115                 120                 125
Tyr Lys Thr Arg Ala Glu Val Lys Phe Glu Gly Asp Thr Leu Val Asn
    130                 135                 140
Arg Ile Glu Leu Lys Gly Ile Asp Phe Lys Glu Asp Gly Asn Ile Leu
145                 150                 155                 160
Gly His Lys Leu Glu Tyr Asn Tyr Asn Ser His Asn Val Tyr Ile Met
                165                 170                 175
Ala Asp Lys Gln Lys Asn Gly Ile Lys Val Asn Phe Lys Ile Arg His
            180                 185                 190
Asn Ile Glu Asp Gly Ser Gly His His His His His His Gly
        195                 200                 205
Ser Val Thr Ser Ala Pro Asp Thr Arg Pro Ala Pro Gly Ser Thr Ala
    210                 215                 220
Pro Pro Ala His Gly Val Thr Ser Ala Pro Asp Thr Arg Pro Ala Pro
225                 230                 235                 240
Gly Ser Thr Ala Pro Pro Ala His Gly Val Thr Ser Ala Pro Asp Thr
                245                 250                 255
Arg Pro Ala Pro Gly Ser His Gly Ser Glu Gln Lys Leu Ile Ser Glu
            260                 265                 270
Glu Asp Leu Gly Ser Gly Ser Val Gln Leu Ala Asp His Tyr Gln Gln
        275                 280                 285
Asn Thr Pro Ile Gly Asp Gly Pro Val Leu Leu Pro Asp Asn His Tyr
    290                 295                 300
Leu Ser Thr Gln Ser Lys Leu Ser Lys Asp Pro Asn Glu Lys Arg Asp
305                 310                 315                 320
His Met Val Leu Leu Glu Phe Val Thr Ala Ala Gly Ile Thr Leu Gly
                325                 330                 335
Met Asp Glu Leu Tyr Lys Gly
            340
```

<210> SEQ ID NO 21
<211> LENGTH: 246
<212> TYPE: PRT
<213> ORGANISM: Artificial Sequence -continued

```
<220> FEATURE:
<223> OTHER INFORMATION: MUC16-1.2TR with C-terminal T7 and His tag

<400> SEQUENCE: 21

Met Gly Lys Thr Asn Leu Phe Leu Phe Leu Ile Phe Ser Leu Leu Leu
1               5                   10                  15

Ser Leu Ser Ser Ala Glu Gln His Met Arg Ile Pro Val Pro Thr Ser
            20                  25                  30

Ser Thr Pro Gly Thr Ser Thr Val Asp Leu Gly Ser Gly Thr Pro Ser
        35                  40                  45

Ser Leu Pro Ser Pro Thr Thr Ala Gly Pro Leu Leu Val Pro Phe Thr
    50                  55                  60

Leu Asn Phe Thr Ile Thr Asn Leu Lys Tyr Glu Glu Asp Met His Cys
65                  70                  75                  80

Pro Gly Ser Arg Lys Phe Asn Thr Thr Glu Arg Val Leu Gln Ser Leu
                85                  90                  95

Leu Gly Pro Met Phe Lys Asn Thr Ser Val Gly Pro Leu Tyr Ser Gly
            100                 105                 110

Cys Arg Leu Thr Leu Leu Arg Ser Glu Lys Asp Gly Ala Ala Thr Gly
        115                 120                 125

Val Asp Ala Ile Cys Thr His Arg Leu Asp Pro Lys Ser Pro Gly Val
    130                 135                 140

Asp Arg Glu Gln Leu Tyr Trp Glu Leu Ser Gln Leu Thr Asn Gly Ile
145                 150                 155                 160

Lys Glu Leu Gly Pro Tyr Thr Leu Asp Arg Asn Ser Leu Tyr Val Asn
                165                 170                 175

Gly Phe Thr His Gln Thr Ser Ala Pro Asn Thr Ser Thr Pro Gly Thr
            180                 185                 190

Ser Thr Val Asp Leu Gly Thr Ser Gly Thr Pro Ser Ser Leu Pro Ser
        195                 200                 205

Pro Thr Ser Ala Gly Pro Leu Leu Val Pro Phe Thr Ala Ala Ala Gly
    210                 215                 220

Ser Gly Met Ala Ser Met Thr Gly Gly Gln Gln Met Gly Leu Ile Asn
225                 230                 235                 240

His His His His His His
                245

<210> SEQ ID NO 22
<211> LENGTH: 1453
<212> TYPE: PRT
<213> ORGANISM: Artificial Sequence
<220> FEATURE:
<223> OTHER INFORMATION: MUC1-3.5TR-Yfp-2A-GolwbppF-2A-T2 polyprotein
      which is co-translationally spliced into MUC1-3.5TR, Golgi-
      localized C-terminal Flag tagged WbpP and GalNAc-T2
<220> FEATURE:
<221> NAME/KEY: 2Asequence
<222> LOCATION: (353)..(370)
<223> OTHER INFORMATION: second 2A sequence from 863-882

<400> SEQUENCE: 22

Met Gly Ala Ser Arg Ser Val Arg Leu Ala Phe Phe Leu Val Val Leu
1               5                   10                  15

Val Val Leu Ala Ala Leu Ala Glu Ala Val Thr Ser Ala Pro Asp Thr
            20                  25                  30

Arg Pro Ala Pro Gly Ser Thr Ala Pro Pro Ala His Gly Val Thr Ser
        35                  40                  45

Ala Pro Asp Thr Arg Pro Ala Pro Gly Ser Thr Ala Pro Pro Ala His
```

```
                50                  55                  60
Gly Val Thr Ser Ala Pro Asp Thr Arg Pro Ala Pro Gly Ser Thr Ala
 65                  70                  75                  80

Pro Pro Ala His Gly Val Thr Ser Ala Pro Asp Thr Val Leu Asn Leu
                 85                  90                  95

Ser Leu Gly Ser Gly Gly Met Val Ser Lys Gly Glu Glu Leu Phe Thr
                100                 105                 110

Gly Val Val Pro Ile Leu Val Glu Leu Asp Gly Asp Val Asn Gly His
                115                 120                 125

Lys Phe Ser Val Ser Gly Glu Gly Glu Gly Asp Ala Thr Tyr Gly Lys
                130                 135                 140

Leu Thr Leu Lys Leu Ile Cys Thr Thr Gly Lys Leu Pro Val Pro Trp
145                 150                 155                 160

Pro Thr Leu Val Thr Thr Leu Gly Tyr Gly Leu Gln Cys Phe Ala Arg
                165                 170                 175

Tyr Pro Asp His Met Lys Gln His Asp Phe Phe Lys Ser Ala Met Pro
                180                 185                 190

Glu Gly Tyr Val Gln Glu Arg Thr Ile Phe Phe Lys Asp Asp Gly Asn
                195                 200                 205

Tyr Lys Thr Arg Ala Glu Val Lys Phe Glu Gly Asp Thr Leu Val Asn
                210                 215                 220

Arg Ile Glu Leu Lys Gly Ile Asp Phe Lys Glu Asp Gly Asn Ile Leu
225                 230                 235                 240

Gly His Lys Leu Glu Tyr Asn Tyr Asn Ser His Asn Val Tyr Ile Thr
                245                 250                 255

Ala Asp Lys Gln Lys Asn Gly Ile Lys Ala Asn Phe Lys Ile Arg His
                260                 265                 270

Asn Ile Glu Asp Gly Gly Val Gln Leu Ala Asp His Tyr Gln Gln Asn
                275                 280                 285

Thr Pro Ile Gly Asp Gly Pro Val Leu Leu Pro Asp Asn His Tyr Leu
                290                 295                 300

Ser Tyr Gln Ser Ala Leu Ser Lys Asp Pro Asn Glu Lys Arg Asp His
305                 310                 315                 320

Met Val Leu Leu Glu Phe Val Thr Ala Ala Gly Ile Thr Leu Gly Met
                325                 330                 335

Asp Glu Leu Tyr Lys His His His His His Thr Ser Gly Ser Gly
                340                 345                 350

Glu Gly Arg Gly Ser Leu Leu Thr Cys Gly Asp Val Glu Glu Asn Pro
                355                 360                 365

Gly Pro Met Arg Arg Arg Ser Arg Met Leu Leu Cys Phe Ala Phe Leu
                370                 375                 380

Trp Val Leu Gly Ile Ala Tyr Tyr Met Tyr Ser Gly Gly Gly Ser Ala
385                 390                 395                 400

Leu Ala Gly Gly Ala Gly Gly Ala Gly Arg Lys Glu Asp Trp Asn
                405                 410                 415

Glu Ile Asp Pro Ile Lys Lys Asp Leu His His Ser Asn Gly Glu
                420                 425                 430

Glu Lys Ala Gln Ser Met Glu Thr Leu Pro Pro Gly Lys Val Arg Trp
                435                 440                 445

Pro Asp Phe Asn Gln Glu Ala Tyr Val Gly Gly Thr Met Val Arg Ser
                450                 455                 460

Gly Gln Asp Pro Tyr Ala Arg Asn Lys Phe Asn Gln Val Glu Ser Asp
465                 470                 475                 480
```

-continued

Lys Leu Arg Met Asp Arg Ala Ile Pro Asp Thr Arg His Asp Gln Cys
            485                 490                 495
Gln Arg Lys Gln Trp Arg Val Asp Leu Pro Ala Thr Met Met Ser Arg
        500                 505                 510
Tyr Glu Glu Leu Arg Lys Glu Leu Pro Ala Gln Pro Lys Val Trp Leu
        515                 520                 525
Ile Thr Gly Val Ala Gly Ser Ile Gly Ser Asn Leu Leu Glu Thr Leu
    530                 535                 540
Leu Lys Leu Asp Gln Lys Val Val Gly Leu Asp Asn Phe Ala Thr Gly
545                 550                 555                 560
His Gln Arg Asn Leu Asp Glu Val Arg Ser Leu Ala Ser Glu Lys Gln
                565                 570                 575
Trp Ser Asn Phe Lys Phe Ile Gln Gly Asp Ile Arg Asn Leu Asp Asp
            580                 585                 590
Cys Asn Asn Ala Cys Ala Gly Val Asp Tyr Val Leu His Gln Ala Ala
        595                 600                 605
Leu Gly Ser Val Pro Arg Ser Ile Asn Asp Pro Ile Thr Ser Asn Ala
    610                 615                 620
Thr Asn Ile Asp Gly Phe Leu Asn Met Leu Ile Ala Ala Arg Asp Ala
625                 630                 635                 640
Lys Val Gln Ser Phe Thr Tyr Ala Ala Ser Ser Ser Thr Tyr Gly Asp
                645                 650                 655
His Pro Gly Leu Pro Lys Val Glu Asp Thr Ile Gly Lys Pro Leu Ser
            660                 665                 670
Pro Tyr Ala Val Thr Lys Tyr Val Asn Glu Leu Tyr Ala Asp Val Phe
        675                 680                 685
Ser Arg Cys Tyr Gly Phe Ser Thr Ile Gly Leu Arg Tyr Phe Asn Val
    690                 695                 700
Phe Gly Arg Arg Gln Asp Pro Asn Gly Ala Tyr Ala Ala Val Ile Pro
705                 710                 715                 720
Lys Trp Thr Ser Ser Met Ile Gln Gly Asp Asp Val Tyr Ile Asn Gly
                725                 730                 735
Asp Gly Glu Thr Ser Arg Asp Phe Cys Tyr Ile Glu Asn Thr Val Gln
            740                 745                 750
Ala Asn Leu Leu Ala Ala Thr Ala Gly Leu Asp Ala Arg Asn Gln Val
        755                 760                 765
Tyr Asn Ile Ala Val Gly Gly Arg Thr Ser Leu Asn Gln Leu Phe Phe
    770                 775                 780
Ala Leu Arg Asp Gly Leu Ala Glu Asn Gly Val Ser Tyr His Arg Glu
785                 790                 795                 800
Pro Val Tyr Arg Asp Phe Arg Glu Gly Asp Val Arg His Ser Leu Ala
                805                 810                 815
Asp Ile Ser Lys Ala Ala Lys Leu Leu Gly Tyr Ala Pro Lys Tyr Asp
            820                 825                 830
Val Ser Ala Gly Val Ala Leu Ala Met Pro Trp Tyr Ile Met Phe Leu
        835                 840                 845
Lys Asp Tyr Lys Asp Asp Asp Lys Leu Glu Gly Ser Gly Gln Thr
        850                 855                 860
Leu Asn Phe Asp Leu Leu Lys Leu Ala Gly Asp Val Glu Ser Asn Pro
865                 870                 875                 880
Gly Pro Met Arg Arg Arg Ser Arg Met Leu Leu Cys Phe Ala Phe Leu
                885                 890                 895

```
Trp Val Leu Gly Ile Ala Tyr Tyr Met Tyr Ser Gly Gly Ser Ala
            900                 905                 910

Leu Ala Gly Gly Ala Gly Gly Ala Gly Arg Lys Glu Asp Trp Asn
            915                 920                 925

Glu Ile Asp Pro Ile Lys Lys Lys Asp Leu His His Ser Asn Gly Glu
            930                 935                 940

Glu Lys Ala Gln Ser Met Glu Thr Leu Pro Pro Gly Lys Val Arg Trp
945                 950                 955                 960

Pro Asp Phe Asn Gln Glu Ala Tyr Val Gly Gly Thr Met Val Arg Ser
                965                 970                 975

Gly Gln Asp Pro Tyr Ala Arg Asn Lys Phe Asn Gln Val Glu Ser Asp
            980                 985                 990

Lys Leu Arg Met Asp Arg Ala Ile Pro Asp Thr Arg His Asp Gln Cys
            995                 1000                1005

Gln Arg Lys Gln Trp Arg Val Asp Leu Pro Ala Thr Ser Val Val
            1010                1015                1020

Ile Thr Phe His Asn Glu Ala Arg Ser Ala Leu Leu Arg Thr Val
            1025                1030                1035

Val Ser Val Leu Lys Lys Ser Pro Pro His Leu Ile Lys Glu Ile
            1040                1045                1050

Ile Leu Val Asp Asp Tyr Ser Asn Asp Pro Glu Asp Gly Ala Leu
            1055                1060                1065

Leu Gly Lys Ile Glu Lys Val Arg Val Leu Arg Asn Asp Arg Arg
            1070                1075                1080

Glu Gly Leu Met Arg Ser Arg Val Arg Gly Ala Asp Ala Ala Gln
            1085                1090                1095

Ala Lys Val Leu Thr Phe Leu Asp Ser His Cys Glu Cys Asn Glu
            1100                1105                1110

His Trp Leu Glu Pro Leu Leu Glu Arg Val Ala Glu Asp Arg Thr
            1115                1120                1125

Arg Val Val Ser Pro Ile Ile Asp Val Ile Asn Met Asp Asn Phe
            1130                1135                1140

Gln Tyr Val Gly Ala Ser Ala Asp Leu Lys Gly Gly Phe Asp Trp
            1145                1150                1155

Asn Leu Val Phe Lys Trp Asp Tyr Met Thr Pro Glu Gln Arg Arg
            1160                1165                1170

Ser Arg Gln Gly Asn Pro Val Ala Pro Ile Lys Thr Pro Met Ile
            1175                1180                1185

Ala Gly Gly Leu Phe Val Met Asp Lys Phe Tyr Phe Glu Glu Leu
            1190                1195                1200

Gly Lys Tyr Asp Met Met Met Asp Val Trp Gly Gly Glu Asn Leu
            1205                1210                1215

Glu Ile Ser Phe Arg Val Trp Gln Cys Gly Gly Ser Leu Glu Ile
            1220                1225                1230

Ile Pro Cys Ser Arg Val Gly His Val Phe Arg Lys Gln His Pro
            1235                1240                1245

Tyr Thr Phe Pro Gly Gly Ser Gly Thr Val Phe Ala Arg Asn Thr
            1250                1255                1260

Arg Arg Ala Ala Glu Val Trp Met Asp Glu Tyr Lys Asn Phe Tyr
            1265                1270                1275

Tyr Ala Ala Val Pro Ser Ala Arg Asn Val Pro Tyr Gly Asn Ile
            1280                1285                1290

Gln Ser Arg Leu Glu Leu Arg Lys Lys Leu Ser Cys Lys Pro Phe
```

```
                1295                1300                1305

Lys Trp Tyr Leu Glu Asn Val Tyr Pro Glu Leu Arg Val Pro Asp
    1310                1315                1320

His Gln Asp Ile Ala Phe Gly Ala Leu Gln Gln Gly Thr Asn Cys
    1325                1330                1335

Leu Asp Thr Leu Gly His Phe Ala Asp Gly Val Val Gly Val Tyr
    1340                1345                1350

Glu Cys His Asn Ala Gly Gly Asn Gln Glu Trp Ala Leu Thr Lys
    1355                1360                1365

Glu Lys Ser Val Lys His Met Asp Leu Cys Leu Thr Val Val Asp
    1370                1375                1380

Arg Ala Pro Gly Ser Leu Ile Lys Leu Gln Gly Cys Arg Glu Asn
    1385                1390                1395

Asp Ser Arg Gln Lys Trp Glu Gln Ile Glu Gly Asn Ser Lys Leu
    1400                1405                1410

Arg His Val Gly Ser Asn Leu Cys Leu Asp Ser Arg Thr Ala Lys
    1415                1420                1425

Ser Gly Gly Leu Ser Val Glu Val Cys Gly Pro Ala Leu Ser Gln
    1430                1435                1440

Gln Trp Lys Phe Thr Leu Asn Leu Gln Gln
    1445                1450

<210> SEQ ID NO 23
<211> LENGTH: 77
<212> TYPE: DNA
<213> ORGANISM: Artificial Sequence
<220> FEATURE:
<223> OTHER INFORMATION: PBY12For primer

<400> SEQUENCE: 23
gagctcatga agactgctgc tttggctcct tgttttttt tgccttctgc tttggctgat      60
tacaaggacg acgacga                                                    77

<210> SEQ ID NO 24
<211> LENGTH: 403
<212> TYPE: PRT
<213> ORGANISM: Artificial Sequence
<220> FEATURE:
<223> OTHER INFORMATION: hUGT1 transporter with C-terminal c-myc tag

<400> SEQUENCE: 24

Met Ala Ala Val Gly Ala Gly Gly Ser Thr Ala Ala Pro Gly Pro Gly
1               5                   10                  15

Ala Val Ser Ala Gly Ala Leu Glu Pro Gly Thr Ala Ser Ala Ala His
            20                  25                  30

Arg Arg Leu Lys Tyr Ile Ser Leu Ala Val Leu Val Val Gln Asn Ala
        35                  40                  45

Ser Leu Ile Leu Ser Ile Arg Tyr Ala Arg Thr Leu Pro Gly Asp Arg
    50                  55                  60

Phe Phe Ala Thr Thr Ala Val Val Met Ala Glu Val Leu Lys Gly Leu
65                  70                  75                  80

Thr Cys Leu Leu Leu Leu Phe Ala Gln Lys Arg Gly Asn Val Lys His
                85                  90                  95

Leu Val Leu Phe Leu His Glu Ala Val Leu Val Gln Tyr Val Asp Thr
            100                 105                 110

Leu Lys Leu Ala Val Pro Ser Leu Ile Tyr Thr Leu Gln Asn Asn Leu
        115                 120                 125
```

Gln Tyr Val Ala Ile Ser Asn Leu Pro Ala Ala Thr Phe Gln Val Thr
    130                 135                 140

Tyr Gln Leu Lys Ile Leu Thr Thr Ala Leu Phe Ser Val Leu Met Leu
145                 150                 155                 160

Asn Arg Ser Leu Ser Arg Leu Gln Trp Ala Ser Leu Leu Leu Leu Phe
                165                 170                 175

Thr Gly Val Ala Ile Val Gln Ala Gln Gln Ala Gly Gly Gly Gly Pro
            180                 185                 190

Arg Pro Leu Asp Gln Asn Pro Gly Ala Gly Leu Ala Ala Val Val Ala
        195                 200                 205

Ser Cys Leu Ser Ser Gly Phe Ala Gly Val Tyr Phe Glu Lys Ile Leu
    210                 215                 220

Lys Gly Ser Ser Gly Ser Val Trp Leu Arg Asn Leu Gln Leu Gly Leu
225                 230                 235                 240

Phe Gly Thr Ala Leu Gly Leu Val Gly Leu Trp Trp Ala Glu Gly Thr
                245                 250                 255

Ala Val Ala Thr Arg Gly Phe Phe Gly Tyr Thr Pro Ala Val Trp
            260                 265                 270

Gly Val Val Leu Asn Gln Ala Phe Gly Gly Leu Leu Val Ala Val Val
        275                 280                 285

Val Lys Tyr Ala Asp Asn Ile Leu Lys Gly Phe Ala Thr Ser Leu Ser
    290                 295                 300

Ile Val Leu Ser Thr Val Ala Ser Ile Arg Leu Phe Gly Phe His Val
305                 310                 315                 320

Asp Pro Leu Phe Ala Leu Gly Ala Gly Leu Val Ile Gly Ala Val Tyr
                325                 330                 335

Leu Tyr Ser Leu Pro Arg Gly Ala Ala Lys Ala Ile Ala Ser Ala Ser
            340                 345                 350

Ala Ser Ala Ser Gly Pro Cys Val His Gln Gln Pro Gly Gln Pro
        355                 360                 365

Pro Pro Pro Gln Leu Ser Ser His Arg Gly Asp Leu Ile Thr Glu Pro
370                 375                 380

Phe Leu Pro Lys Ser Val Leu Val Lys Glu Gln Lys Leu Ile Ser Glu
385                 390                 395                 400

Glu Asp Leu

<210> SEQ ID NO 25
<211> LENGTH: 17
<212> TYPE: PRT
<213> ORGANISM: Artificial Sequence
<220> FEATURE:
<223> OTHER INFORMATION: secretion signal peptide sequence of
      Rhamnogalacturonan acetylesterase from Aspergillus aculeatus

<400> SEQUENCE: 25

Met Lys Thr Ala Ala Leu Ala Pro Leu Phe Phe Leu Pro Ser Ala Leu
1               5                   10                  15

Ala

<210> SEQ ID NO 26
<211> LENGTH: 28
<212> TYPE: PRT
<213> ORGANISM: Artificial Sequence
<220> FEATURE:
<223> OTHER INFORMATION: secretion signal peptide sequence of
      alpha-amylase from Oryza sativa (japonica cultivar-group)

-continued

```
<400> SEQUENCE: 26

Met Ala Lys His Ser Thr Thr Met Ser Cys Leu Leu Phe Phe Val Leu
1               5                   10                  15

Leu Cys Leu Gly Ser His Leu Ala Gln Ala Gln Val
            20                  25

<210> SEQ ID NO 27
<211> LENGTH: 25
<212> TYPE: PRT
<213> ORGANISM: Artificial Sequence
<220> FEATURE:
<223> OTHER INFORMATION: secretion signal peptide sequence of aspartic
      protease from Physcomitrella patens

<400> SEQUENCE: 27

Met Gly Ala Ser Arg Ser Val Arg Leu Ala Phe Phe Leu Val Val Leu
1               5                   10                  15

Val Val Leu Ala Ala Leu Ala Glu Ala
            20                  25

<210> SEQ ID NO 28
<211> LENGTH: 21
<212> TYPE: PRT
<213> ORGANISM: Artificial Sequence
<220> FEATURE:
<223> OTHER INFORMATION: secretion signal peptide sequence of
      proline-rich protein 3 from Nicotiana tabacum

<400> SEQUENCE: 28

Met Gly Lys Met Ala Ser Leu Phe Ala Ser Leu Leu Val Val Leu Val
1               5                   10                  15

Ser Leu Ser Leu Ala
            20

<210> SEQ ID NO 29
<211> LENGTH: 21
<212> TYPE: PRT
<213> ORGANISM: Artificial Sequence
<220> FEATURE:
<223> OTHER INFORMATION: secretion signal peptide sequence of
      Arabidopsis thaliana Basic Chitinase

<400> SEQUENCE: 29

Met Gly Lys Thr Asn Leu Phe Leu Phe Leu Ile Phe Ser Leu Leu Leu
1               5                   10                  15

Ser Leu Ser Ser Ala
            20

<210> SEQ ID NO 30
<211> LENGTH: 21
<212> TYPE: PRT
<213> ORGANISM: Artificial Sequence
<220> FEATURE:
<223> OTHER INFORMATION: secretion signal peptide sequence of Nicotiana
      tabacum extensin precursor

<400> SEQUENCE: 30

Met Gly Lys Met Ala Ser Leu Phe Ala Thr Phe Leu Val Val Leu Val
1               5                   10                  15

Ser Leu Ser Leu Ala
            20

<210> SEQ ID NO 31
<211> LENGTH: 50
```

```
<212> TYPE: DNA
<213> ORGANISM: Artificial Sequence
<220> FEATURE:
<223> OTHER INFORMATION: PBY12Rev primer

<400> SEQUENCE: 31
agcgctaggc ctgagctctc atagctcatc tttcaaaaac atgatgtacc            50

<210> SEQ ID NO 32
<211> LENGTH: 44
<212> TYPE: DNA
<213> ORGANISM: Artificial Sequence
<220> FEATURE:
<223> OTHER INFORMATION: PT2anchorFor primer

<400> SEQUENCE: 32
cacgtggaat tcgccatggt tatgcggcgg cgctcgcgga tgct                  44

<210> SEQ ID NO 33
<211> LENGTH: 32
<212> TYPE: DNA
<213> ORGANISM: Artificial Sequence
<220> FEATURE:
<223> OTHER INFORMATION: PT2anchorrev primer

<400> SEQUENCE: 33
cgactcatca tggtggccgg cagatccacc cg                               32

<210> SEQ ID NO 34
<211> LENGTH: 32
<212> TYPE: DNA
<213> ORGANISM: Artificial Sequence
<220> FEATURE:
<223> OTHER INFORMATION: PGolwbppFor primer

<400> SEQUENCE: 34
gccggccacc atgatgagtc gttatgaaga gc                               32

<210> SEQ ID NO 35
<211> LENGTH: 40
<212> TYPE: DNA
<213> ORGANISM: Artificial Sequence
<220> FEATURE:
<223> OTHER INFORMATION: PGolwbppRev primer

<400> SEQUENCE: 35
agcgctaggc ctgagctctc atttcaaaaa catgatgtac                       40

<210> SEQ ID NO 36
<211> LENGTH: 38
<212> TYPE: DNA
<213> ORGANISM: Artificial Sequence
<220> FEATURE:
<223> OTHER INFORMATION: P-T4For primer

<400> SEQUENCE: 36
ggatccacgc gtaaaatggc ggtgaggtgg acttgggc                         38

<210> SEQ ID NO 37
<211> LENGTH: 31
<212> TYPE: DNA
<213> ORGANISM: Artificial Sequence
<220> FEATURE:
<223> OTHER INFORMATION: P-T4Rev primer

<400> SEQUENCE: 37
```

```
ggatccctat ttctcaaaac tccaaatttg a                                    31
```

<210> SEQ ID NO 38
<211> LENGTH: 61
<212> TYPE: DNA
<213> ORGANISM: Artificial Sequence
<220> FEATURE:
<223> OTHER INFORMATION: P-HAT2For primer

<400> SEQUENCE: 38

```
ggcttaauat gtacccatac gacgtcccag actacgcccg gcggcgctcg cggatgctgc    60
t                                                                    61
```

<210> SEQ ID NO 39
<211> LENGTH: 59
<212> TYPE: DNA
<213> ORGANISM: Artificial Sequence
<220> FEATURE:
<223> OTHER INFORMATION: P-HAT2Rev primer

<400> SEQUENCE: 39

```
acttaagcaa aucaaaattc aaagtttgac cagaaccctg ctgcaggttg agcgtgaac     59
```

<210> SEQ ID NO 40
<211> LENGTH: 66
<212> TYPE: DNA
<213> ORGANISM: Artificial Sequence
<220> FEATURE:
<223> OTHER INFORMATION: PFwbppFor primer

<400> SEQUENCE: 40

```
atttgcttaa gutggcagga gatgtggaat ctaacccagg acctatggat tacaaggacg    60
acgacg                                                               66
```

<210> SEQ ID NO 41
<211> LENGTH: 26
<212> TYPE: DNA
<213> ORGANISM: Artificial Sequence
<220> FEATURE:
<223> OTHER INFORMATION: PFwbppRev primer

<400> SEQUENCE: 41

```
ggtttaautc atttcaaaaa catgat                                         26
```

<210> SEQ ID NO 42
<211> LENGTH: 27
<212> TYPE: DNA
<213> ORGANISM: Artificial Sequence
<220> FEATURE:
<223> OTHER INFORMATION: PT2Rev primer

<400> SEQUENCE: 42

```
gagctcctac tgctgcaggt tgagcgt                                        27
```

<210> SEQ ID NO 43
<211> LENGTH: 33
<212> TYPE: DNA
<213> ORGANISM: Artificial Sequence
<220> FEATURE:
<223> OTHER INFORMATION: PFlagFor primer

<400> SEQUENCE: 43

```
tctagaatgg attacaagga cgacgacgac aag                                 33
```

<210> SEQ ID NO 44
<211> LENGTH: 90
<212> TYPE: DNA
<213> ORGANISM: Artificial Sequence
<220> FEATURE:
<223> OTHER INFORMATION: PBY9For primer

<400> SEQUENCE: 44
ctgcagatga agaccgccgc tcttgcaccg ctcttcttcc tccctctgc cctcgccact      60 actcacgtgc atcatcatca tcatcacagt                                     90

<210> SEQ ID NO 45
<211> LENGTH: 27
<212> TYPE: DNA
<213> ORGANISM: Artificial Sequence
<220> FEATURE:
<223> OTHER INFORMATION: PBY9REV primer

<400> SEQUENCE: 45
gagctcctag gtgtccgggg ccgaggt                                        27

<210> SEQ ID NO 46
<211> LENGTH: 24
<212> TYPE: DNA
<213> ORGANISM: Artificial Sequence
<220> FEATURE:
<223> OTHER INFORMATION: PPpSP-MUC1-3.5TRFor primer

<400> SEQUENCE: 46
ggcttaauat gggggcatcg agga                                           24

<210> SEQ ID NO 47
<211> LENGTH: 30
<212> TYPE: DNA
<213> ORGANISM: Artificial Sequence
<220> FEATURE:
<223> OTHER INFORMATION: PMUC1-3.5TRRev primer

<400> SEQUENCE: 47
ggtttaauac tgtatccggt gcggaagtga                                     30

<210> SEQ ID NO 48
<211> LENGTH: 96
<212> TYPE: DNA
<213> ORGANISM: Artificial Sequence
<220> FEATURE:
<223> OTHER INFORMATION: PAtSpYfpFor primer

<400> SEQUENCE: 48
gagctccatg gtaagacta atcttttct ctttctcatc ttttcacttc tcctatcatt      60
atcctcggcc gagcaagtga gcaagggcga ggagct                              96

<210> SEQ ID NO 49
<211> LENGTH: 25
<212> TYPE: DNA
<213> ORGANISM: Artificial Sequence
<220> FEATURE:
<223> OTHER INFORMATION: PYfpRev primer

<400> SEQUENCE: 49
catatgcttg tacagctcgt ccatg                                          25

<210> SEQ ID NO 50
<211> LENGTH: 29
<212> TYPE: DNA

```
<213> ORGANISM: Artificial Sequence
<220> FEATURE:
<223> OTHER INFORMATION: P-MUC1-2TR For primer

<400> SEQUENCE: 50
ccatggctct gttactagtg ctccagata                                29

<210> SEQ ID NO 51
<211> LENGTH: 26
<212> TYPE: DNA
<213> ORGANISM: Artificial Sequence
<220> FEATURE:
<223> OTHER INFORMATION: P-MUC1-2TRRev primer

<400> SEQUENCE: 51
ccatgggatc ccggagcagg tcttgt                                   26

<210> SEQ ID NO 52
<211> LENGTH: 98
<212> TYPE: DNA
<213> ORGANISM: Artificial Sequence
<220> FEATURE:
<223> OTHER INFORMATION: P-GFPFor primer

<400> SEQUENCE: 52
gagctccatg ggtaagacta atcttttttct ctttctcatc ttttcacttc tcctatcatt    60
atcctcggcc gagcaagtga gcaagggcga ggagctgt                             98

<210> SEQ ID NO 53
<211> LENGTH: 32
<212> TYPE: DNA
<213> ORGANISM: Artificial Sequence
<220> FEATURE:
<223> OTHER INFORMATION: P-GFPRev primer

<400> SEQUENCE: 53
gagctcctac cccttgtaca gctcgtccat gc                            32

<210> SEQ ID NO 54
<211> LENGTH: 26
<212> TYPE: DNA
<213> ORGANISM: Artificial Sequence
<220> FEATURE:
<223> OTHER INFORMATION: PpSP-MUC1-3.5TR-YfpFor primer

<400> SEQUENCE: 54
tctagaatgg gggcatcgag gagtgt                                   26

<210> SEQ ID NO 55
<211> LENGTH: 59
<212> TYPE: DNA
<213> ORGANISM: Artificial Sequence
<220> FEATURE:
<223> OTHER INFORMATION: PpSP-MUC1-3.5TR-YfpRev primer

<400> SEQUENCE: 55
gttaacaaag atcctctccc ttcaccacta ccactagtgt gatggtgatg gtgatgctt      59

<210> SEQ ID NO 56
<211> LENGTH: 57
<212> TYPE: DNA
<213> ORGANISM: Artificial Sequence
<220> FEATURE:
<223> OTHER INFORMATION: P2AGo1wbppFor primer

<400> SEQUENCE: 56
```

```
gttaacttgt ggagacgtgg aagagaaccc tggacctatg cggcggcgct cgcggat      57
```

<210> SEQ ID NO 57
<211> LENGTH: 67
<212> TYPE: DNA
<213> ORGANISM: Artificial Sequence
<220> FEATURE:
<223> OTHER INFORMATION: P2AGolwbppFRev primer

<400> SEQUENCE: 57

```
gctagcttca ggagatcaaa attaagagtt tgcccgctgc cctcgagctt gtcgtcgtcg      60
tccttgt                                                                67
```

<210> SEQ ID NO 58
<211> LENGTH: 54
<212> TYPE: DNA
<213> ORGANISM: Artificial Sequence
<220> FEATURE:
<223> OTHER INFORMATION: P2AT2For primer

<400> SEQUENCE: 58

```
gctagctgga gacgttgagt caaatccagg tccgatgcgg cggcgctcgc ggat            54
```

<210> SEQ ID NO 59
<211> LENGTH: 27
<212> TYPE: DNA
<213> ORGANISM: Artificial Sequence
<220> FEATURE:
<223> OTHER INFORMATION: P2AT2Rev primer

<400> SEQUENCE: 59

```
gagctcctac tgctgcaggt tgagcgt                                          27
```

<210> SEQ ID NO 60
<211> LENGTH: 9
<212> TYPE: PRT
<213> ORGANISM: Artificial Sequence
<220> FEATURE:
<223> OTHER INFORMATION: Flag-tag sequence

<400> SEQUENCE: 60

Met Asp Tyr Lys Asp Asp Asp Asp Lys
1               5

<210> SEQ ID NO 61
<211> LENGTH: 8
<212> TYPE: PRT
<213> ORGANISM: Artificial Sequence
<220> FEATURE:
<223> OTHER INFORMATION: Flag-tag sequence

<400> SEQUENCE: 61

Asp Tyr Lys Asp Asp Asp Asp Lys
1               5

<210> SEQ ID NO 62
<211> LENGTH: 32
<212> TYPE: DNA
<213> ORGANISM: Artificial Sequence
<220> FEATURE:
<223> OTHER INFORMATION: PwbppFor primer

<400> SEQUENCE: 62

```
gccggccacc atgatgagtc gttatgaaga gc                                    32
```

```
<210> SEQ ID NO 63
<211> LENGTH: 40
<212> TYPE: DNA
<213> ORGANISM: Artificial Sequence
<220> FEATURE:
<223> OTHER INFORMATION: PwbppRev primer

<400> SEQUENCE: 63
agcgctaggc ctgagctctc atttcaaaaa catgatgtac                    40

<210> SEQ ID NO 64
<211> LENGTH: 31
<212> TYPE: DNA
<213> ORGANISM: Artificial Sequence
<220> FEATURE:
<223> OTHER INFORMATION: Promoter sequence

<400> SEQUENCE: 64
ccatccggat ccgaattctg cagagctcat g                             31

<210> SEQ ID NO 65
<211> LENGTH: 29
<212> TYPE: DNA
<213> ORGANISM: Artificial Sequence
<220> FEATURE:
<223> OTHER INFORMATION: Terminator sequence

<400> SEQUENCE: 65
taggaaccta gcgctggtga ccagctcga                                29

<210> SEQ ID NO 66
<211> LENGTH: 104
<212> TYPE: DNA
<213> ORGANISM: Artificial Sequence
<220> FEATURE:
<223> OTHER INFORMATION: Fwbpp fusion

<400> SEQUENCE: 66
cgctcaacct gcagcagggt tctggtcaaa ctttgaattt tgatttgctt aagttggcag    60
gagatgtgga atctaaccca ggacctatgg attacaagga cgac                    104

<210> SEQ ID NO 67
<211> LENGTH: 35
<212> TYPE: PRT
<213> ORGANISM: Artificial Sequence
<220> FEATURE:
<223> OTHER INFORMATION: Fwbpp fusion

<400> SEQUENCE: 67

Thr Leu Asn Leu Gln Gln Gly Ser Gly Gln Thr Leu Asn Phe Asp Leu
1               5                   10                  15

Leu Lys Leu Ala Gly Asp Val Glu Ser Asn Pro Gly Pro Met Asp Tyr
            20                  25                  30

Lys Asp Asp
        35

<210> SEQ ID NO 68
<211> LENGTH: 28
<212> TYPE: DNA
<213> ORGANISM: Artificial Sequence
<220> FEATURE:
<223> OTHER INFORMATION: PwbppFor primer

<400> SEQUENCE: 68
```

-continued

```
tctagaatga tgagtcgtta tgaagagc                                        28
```

<210> SEQ ID NO 69
<211> LENGTH: 27
<212> TYPE: DNA
<213> ORGANISM: Artificial Sequence
<220> FEATURE:
<223> OTHER INFORMATION: PT2Rev primer

<400> SEQUENCE: 69

```
gagctcctac tgctgcaggt tgagcgt                                         27
```

<210> SEQ ID NO 70
<211> LENGTH: 6
<212> TYPE: PRT
<213> ORGANISM: Artificial Sequence
<220> FEATURE:
<223> OTHER INFORMATION: Trombin cleavage recognition sequence

<400> SEQUENCE: 70

Leu Val Pro Arg Gly Ser
1               5

<210> SEQ ID NO 71
<211> LENGTH: 11
<212> TYPE: PRT
<213> ORGANISM: Artificial Sequence
<220> FEATURE:
<223> OTHER INFORMATION: T7 epitope tag

<400> SEQUENCE: 71

Met Ala Ser Met Thr Gly Gly Gln Gln Met Gly
1               5                   10

<210> SEQ ID NO 72
<211> LENGTH: 102
<212> TYPE: DNA
<213> ORGANISM: Artificial Sequence
<220> FEATURE:
<223> OTHER INFORMATION: Yfp(H)6-2A-5'-GalNAc-T2

<400> SEQUENCE: 72

```
catcaccatc accatcacac tagtggtagt ggtgaaggga gaggatcttt gttaacttgt     60
ggagacgtgg aagagaaccc tggacctatg cggcggcgct cg                       102
```

<210> SEQ ID NO 73
<211> LENGTH: 34
<212> TYPE: PRT
<213> ORGANISM: Artificial Sequence
<220> FEATURE:
<223> OTHER INFORMATION: Yfp(H)6-2A-5'-GalNAc-T2

<400> SEQUENCE: 73

His His His His His His Thr Ser Gly Ser Gly Glu Gly Arg Gly Ser
1               5                   10                  15

Leu Leu Thr Cys Gly Asp Val Glu Glu Asn Pro Gly Pro Met Arg Arg
            20                  25                  30

Arg Ser

<210> SEQ ID NO 74
<211> LENGTH: 102
<212> TYPE: DNA
<213> ORGANISM: Artificial Sequence
<220> FEATURE:
<223> OTHER INFORMATION: 3'-GolT2wbppF-2A-5'-GalNAc-T2

```
<400> SEQUENCE: 74
gacgacgaca agctcgaggg cagcgggcaa actcttaatt ttgatctcct gaagctagct        60
ggagacgttg agtcaaatcc aggtccgatg cggcggcgct cg                          102

<210> SEQ ID NO 75
<211> LENGTH: 34
<212> TYPE: PRT
<213> ORGANISM: Artificial Sequence
<220> FEATURE:
<223> OTHER INFORMATION: 3'-GolT2wbppF-2A-5'-GalNAc-T2

<400> SEQUENCE: 75

Asp Asp Asp Lys Leu Glu Gly Ser Gly Gln Thr Leu Asn Phe Asp Leu
1               5                   10                  15

Leu Lys Leu Ala Gly Asp Val Glu Ser Asn Pro Gly Pro Met Arg Arg
            20                  25                  30

Arg Ser

<210> SEQ ID NO 76
<211> LENGTH: 40
<212> TYPE: DNA
<213> ORGANISM: Artificial Sequence
<220> FEATURE:
<223> OTHER INFORMATION: PwbppRev primer

<400> SEQUENCE: 76
agcgctaggc ctgagctctc atttcaaaaa catgatgtac                              40
```

METHODS FOR GLYCO-ENGINEERING PLANT CELLS FOR CONTROLLED HUMAN O-GLYCOSYLATION

This application claims benefit of Ser. No. 61/316,401, filed 23 Mar. 2010 in the United States and which application is incorporated herein by reference. A claim of priority to the extent appropriate is made.

FIELD OF THE INVENTION

The present invention concerns the development of a novel platform for recombinant production of bioactive glycoproteins by engineering plant cells to produce mammalian type O-glycosylation.

The invention has provided a promising model cancer vaccine by producing mucins and other proteins with cancer specific mucin-type O-glycosylation. The invention include a number of proprietary host cell systems for recombinant production of designed O-glycosylation, i.e. "human-like" glycoproteins, cell systems for exploring regulation of mammalian O-glycosylation, and improved cancer vaccines.

BACKGROUND OF THE INVENTION

Currently, mammalian cells are required for human O-glycosylation, but plants offer a unique cell platform for engineering O-glycosylation since they do not perform human mucin-type O-glycosylation. The invention has identified plant cells as the only eukaryotic cells without mammalian O-glycosylation or the competing (for sites) yeast O-mannosylation (Amano et al. 2008). Protein O-glycosylation in plants is intrinsically different to O-glycosylation in mammals, i.e. with respect to i) groups of proteins subjected to O-glycosylation, the particular amino acids modified and iii) the sugars constituting the O-glycans.

There are a number of alternative approaches to producing therapeutic proteins featuring modified O-glycans: Glycosylation in vitro using isolated glycosyltransferases and supplied nucleotide sugars solves the problem of undesired, further glycosylation of the O-glycan of interest, but does so at a price. Nucleotide sugars are expensive substrates and the method does not scale well. In addition for larger peptide/protein substrates, which can not be produced by chemical synthesis but have to be produced in non-glycosylating host cells like *E. coli*, it is complicated and laborious to define in vitro glycosylation status and achieve a homogenous product. Engineering human-type O-glycosylation into a fungal host cell has been described in the prior art (US20090068702) and may be regarded as a parallel approach to the problem solved by the present invention. The fungal O-mannosylation machinery mentioned above targets serine and threonine residues and thus poses a much higher risk of cross-talk than is observed in plant cells.

Once the ability to carry out the first steps of human-style O-glycosylation in a plant cell has been demonstrated with the aim of producing controlled, truncated glycans, it will be obvious to workers skilled in the art, that further engineering will allow the production of native length O-glycosylation of target proteins or peptides. It is further obvious that there are a number of therapeutic proteins for which a host cell performing native O-glycosylation would be an attractive production platform.

So in general, production of therapeutics in plants offer the obvious advantages of high yields, low costs, low risk of cross-talk from competing post-translational mechanisms of protein modification and no risk of contamination with infectious agents.

Attractive cancer vaccine candidates are selected from proteins, or parts thereof, that e.g. are exposed on cell surfaces and which feature modified, typically truncated glycans that set these protein epitopes apart from the similar structural features on healthy cells. Mucins are one class of particularly important cell surface proteins in this regard. A large family of 20 polypeptide GalNAc-transferases control the initiation step of mucin-type O-glycosylation, which defines the sites and patterns of O-glycan decoration of glycoproteins. The polypeptide GalNAc-transferase isoforms (GalNAc-Ts) have been demonstrated in in vitro studies to have different peptide substrate specificities, however, a significant degree of overlap in specificities exists especially with mucin-like substrates with high-density clustered acceptor sites. Cell and tissue expression patterns of individual GalNAc-transferase isoforms are also distinctly different but with significant overlap, and it is expected that all cells express multiple isoforms.

Mucins are a family of large (>200 kDa) heavily glycosylated proteins, which are characterized by a variable number of tandem repeats. Human mucin-1 (Muc1) is a member of this subfamily and has between 25 and 125 heavy glycosylated repeats, termed varying number of tandem repeats (VNTR), which is also known as the mucin-domain (Hattrup & Gendler 2008), presented towards the extra cellular matrix. Successful introduction of mucin-type protein O-glycosylation into plant cells requires:
i) that host plant cells do not modify the target peptide substrates to be used and
ii) that the appropriate enzymes and substrates are introduced into the plant cells such that O-glycosylation in the secretory pathway proceed and the glycosylated peptide substrates are preferentially exported to the exterior of the cell.

Human mucins are large heavily O-glycosylated glycoproteins (>200 kDa), which account for the majority of proteins in mucus layers, which hydrate, lubricate and protect cells from proteases as well as from pathogens. O-linked mucin glycans are truncated in many cancers, e.g. yielding the truncated cancer specific epitope Tn (a single GalNAc sugar attached to the amino acids Serine or Threonine, Cf. Tarp & Clausen 2008).

Compared to healthy epithelia tissue the mucin-type MUC1 protein is highly overexpressed and the protein contains truncated aberrant O-glycosylation in epithelia cancer cells.

Glycosylation is the enzymatic addition of glycan moieties to proteins. The initial steps of glycosylation involve recognition events between target protein and a glycosyltransferase, which events determine the sites of glycan attachment. Different glycosyltransferases have been isolated and a number of specific sites of glycan addition to proteins have been determined. Glycosylation of serine and threonine residues during mucin-type O-linked protein glycosylation is catalyzed by a family of GalNAc-Transferases (EC 2.4.1.41). GalNAc-Transferases characterized to date have distinct and/or overlapping acceptor substrate specificities. Bennett et al. (1996), supra; Wandall et al. (1997); Bennett et al. (1998); Gerken et al. (2006); Wandall et al. (2007). Recent findings have suggested that the GalNAc-transferases comprise a gene family and that each GalNAc-Transferase has distinct functions.

In plants, O-glycosylation cell wall hydroxyproline-rich glycoproteins (HRGP's) serine, threonine and hydroxyl-prolines (Hyp or 'O'). HRGP's can be divided into three families: extensins, arbinogalactan proteins (AGP's) and proline-rich proteins (PRP's). Substantial evidence points to that the primary sequences of the HRGP's are determinants of HRGP hydroxylation and glycosylation (Jamet et al. 2008). Only two proline C4-hydroxylases (P4Hs) from higher plants have been cloned and characterized so far (Hieta & Myllyharju 2002; Tiainen et al. 2005). Both recombinant P4Hs effectively hydroxylated synthetic peptides corresponding to Pro-rich repeats found in many plant glycoproteins. Plant and mammalian P4H sequence-specificities differ markedly. As a result, the proline residues of human collagen-I, which are otherwise hydroxylated in humans is e.g. not hydroxylated when produced in transgenic tobacco plants (Gomord and Faye 2004). A proposed code based on hydroxylation of a single Pro residue in vacuolar sporamin expressed in tobacco BY-2 cells correctly identifies many arabinogalactosylation sites in AGPs (Shimizu et al. 2005). The ideal P4H hydroxylation sequence motif was determined to be [AVSTG]-Pro-[AVSTGA]-[GAVPSTC]-[APS or acidic (D and E)] with the Pro residue being hydroxylated. While it is not claimed that this motif captures hydroxylation of every Hyp of the typical plant proteome, it is clear that plants are fundamentally different from mammals with regard to the amino acid sequences that are recognized as sites for O-glycosylation. There is but a single protein sequence from *homo sapiens* that serendipitously feature a plant O-glycosylation motif, and that is the hinge region 1 in IgA1, which was predicted to match the requirements for proline hydroxylation and glycosylation and also demonstrated experimentally to be hydroxylated and arabinosylated in a plant like fashion (Karnoup et al. 2005). Workers skilled in the art will appreciate that sequences of vaccine candidates may be evaluated by bioinformatic methods and modified should spurious plant glycosylation motives be detected.

Plants further do not contain GalNAc and this constitutes a second barrier to cross-talk from the glycosylation machinery of the plant cell. The side-activity of barley UDP-Glc/UDP-Gal C4-epimerase (UGE 1, EC 5.1.3.2) using UDP-GlcNAc in vitro has been measured to be 500-600 times lower than with the native substrates UDP-Glc and UDP-Gal (Qisen et al. 2006). Thus, UDP-GalNAc production has to be introduced into the plant cell. Subsequent successful introduction of GalNAc onto a polypeptide backbone will not render it recognizable be the post-translational modification system of the plant cell.

It is well known in the prior art that eukaryotic genes encoding, including mammalian genes, may be expressed in higher plants. The non-trivial interplay among gene products required for establishing mucin-type O-glycosylation in a plant host cell has, however, never been achieved. The present invention demonstrates successful glycosylation of mammalian target proteins using several types of higher plant host cells.

In the current invention introduction of basal mucin-type O-glycosylation in plants involves:
1. Engineering O-glycosylation capacity: Expression of Golgi-targeted human polypeptide GalNAc-Transferase(s) (GalNAc-T2 and optionally -T4) and a UDP-GlcNAc C4-epimerase (WbpP), which converts UDP-GlcNAc to UDP-GalNAc, as UDP-GalNAc is not part of the nucleotide sugar repertoire in plants.
2. Expression of human polypeptide target substrate in the O-glycosylation capacity background

SUMMARY OF THE INVENTION

In a first aspect the present invention provides a method for the initiation of mammalian O-glycosylation in a plant cell comprising the steps of introducing, by transient or stable transformation, a UDP-GlcNAc/UDP-Glc C4-epimerase and at least one polypeptide GalNAc-Transferase.

Preferably the GalNAc-Transferase is targeted to the Golgi apparatus and the UDP-GlcNAc/UDP-Glc C4-epimerase is cytosolic. In a particularly preferred embodiment the plant cell is further transformed with a UDP-GalNAc-Transporter.

In accordance with the method of the present invention it is preferred that the GalNAc-Transferase(s) is/are targeted to the Golgi apparatus and the UDP-GlcNAc/UDP-Glc C4-epimerase is targeted to the secretory pathway as a luminal protein or retained in the ER or in the Golgi. Also preferred is that the GalNAc-transferase(s) is/are selected from CAZy family GT27. More preferred is that the GalNAc-Transferase (s) is/are selected among the genes of *Homo sapiens* and their orthologs in other mammals. Most preferred is that the GalNAc-Transferase(s) is/are selected from genes encoding proteins that are more than 60% identical to the amino acid sequences of human UDP-GalNAc-T2 or human UDP-Gal-NAc-T4.

In an particularly preferred embodiment of the present invention the UDP-GlcNAc/UDP-Glc C4-epimerase is selected from either eukaryotic or prokaryotic C4'-epimerases, such as C4'-epimerase genes encoding proteins that are more than 45% identical to the amino acid sequence of the *Pseudomonas* WbpP epimerase.

The plant cell of the present invention is preferably selected from the genera *Nicotiana, Arabidopsis, Physcomitrella, Lemna, Hordeum, Triticum* or *Brachypodium*, such as a Chlorophyte or Charophyte alga.

Preferably the plant cell is further transformed, transiently or stably, with a nucleotide construct encoding a mucin-type protein, such as a nucleotide construct encoding a non-mucin-type therapeutic protein. In a particularly preferred embodiment of the present invention the protein of interest is secreted from the cell, in planta or in vitro.

In a second aspect of the present invention there is provided a mucin-derived or other therapeutic protein produced according to the method of the present invention.

BRIEF DESCRIPTION OF THE DRAWINGS

FIG. 1 shows the expression of cytoplasmic WbpP
FIG. 2. shows the expression of ER targeted WbpP
FIG. 3. shows the expression of Golgi targeted WbpP
FIG. 4. shows the expression of Golgi targeted GalNAc-T2
FIG. 5. shows the expression of cytoplasmic FWbpP and HA tagged Golgi GalNAc-T2 from one polycistronic transcript
FIG. 6. shows the expression of Golgi GalNAc-T2 and cytoplasmic WbpPF from one polycistronic transcript
FIG. 7. shows the expression of cytoplasmic FWbpP and Golgi GalNAc-T2 from one polycistronic transcript
FIG. 8. shows the expression of MUC1-3.5TR
FIG. 9. shows the structure of *E. coli* derived MUC1-3.5TR
FIG. 10. shows the structure of *A. thaliana* derived MUC1-3.5TR
FIG. 11. shows mucin-type O-glycosylation of MUC1-3.5TR with fused C-terminal Glycomodule
FIG. 12. shows mucin-type O-glycosylation of MUC1-3.5TR-Yfp target peptide
FIG. 13. shows transient expression of MUC1-3.5TR-Yfp in the moss *Physcomitrella patens*
FIG. 14. shows structure of MUC1-3.5TR-Yfp expressed in WT and O-glycosylation capacity background FIG. 15. shows single and combined constructs encoding Golgi targeted epimerase and GalNAc-T2 conferring Mucin-type O-glycosylation FIG. 16. shows stable *Arabidopsis* line expressing a single construct conferring Mucin-type O-glycosylation FIG. 17. shows mucin-type O-glycosylation of Yfp-MUC1-3.5TR target peptide FIG. 18. shows mucin-type O-glycosylation of embedded G-MUC1-2TR-fp target peptide FIG. 19. shows the expression and Mucin-type O-glycosylation of MUC16 target peptide FIG. 20. shows the expression and O-glycosylation of human interferon α2B FIG. 21. shows the expression of human podoplanin (hPOD)

FIG. 22. shows the expression of MUC1-3.5TR & GalNAc-T2 and localization of GalNAc-T2 in stably transformed tobacco BY-2 cells FIG. 23. shows the co-expression of MUC1-3.5TR and GalNAc-T2 in stably transformed *Arabidopsis thaliana*

DETAILED DESCRIPTION OF THE INVENTION

The examples underpinning the present invention regard the heterologous expression of the desired product in different host cell systems that are engineered to undertake the desired posttranslational modifications (PTMs). Mode of expression—single cells in vitro, intact plants of different species and transient versus stable transformation of host cells—is addressed in different scenarios in the examples that are summarized in the following. Expression of a sugar nucleotide epimerase and a sugar nucleotide transporter that supply the glycosyltranferases with their donor substrate is addressed. The transporter is investigated relative to cytosolic localization of the epimerase and is contrasted with localizing the epimerase to the secretory pathway which renders the transporter superfluous.

The examples further relate to the expression of GalNAc-transferases (GalNAc-T2 and -T4) that recognize different acceptor sequence motifs of the target protein or peptides. The examples further address effects on expression level and product stability of chimeric constructs in which the target substrate is fused to arabinogalactan modules or yellow fluorescent proteins.

Example E1.1 and the accompanying FIG. 1 demonstrate the successful expression of the UDP-GalNAc epimerase from *Pseudomonas*. The sequence was tagged with a Flag Tag and analyzed by Western blotting. An antibody against the Flag Tag specifically detected a protein of the expected MW.

Example E1.2 and the accompanying FIG. 2 demonstrate the successful expression of the epimerase of example E1.1 but targeted to the secretory pathway and retained in the endoplasmatic reticulum (ER) using a signal peptide from rice and the KDEL ER-retention signal. Analysis by Western blots as in E1.1.

Example E1.3 and the accompanying FIG. 3 demonstrate the successful anchoring of the epimerase to the Golgi membrane through the use of a chimeric construct comprising the N-terminal Golgi anchor of UDP-GalNAc-transferase T2, the epimerase and the Flag Tag. Analysis by Western blots as above.

Example E2 and the accompanying FIG. 4 demonstrate the successful heterologous expression of the Golgi-targeted UDP-GalNAc-transferase T2 (GalNAc-T2). The native membrane anchor of GalNAc-T2 is used without addition of any tags. Detection by Western using a monoclonal antibody raised against the T2-protein itself.

Example E3.1 and E3.3 plus the accompanying FIG. 5 and FIG. 7 demonstrate the successful co-expression of GalNAc-T2 and the epimerase from a polycistronic construct. The GalNAc-T2 is targeted to the Golgi while the epimerase is targeted to the cytoplasm. Cleavage of the two proteins is accomplished by use of the self-splicing 2A sequence, which interspaces the two enzymes in the polycistronic gene product. Both transient and stable expressions are demonstrated; and both a single cell system (BY-2 cells cultured in vitro) and intact plant systems are provided. In E3.1 Golgi GalNAc-T2 has an N-terminal Hema Agglutinin (HA) tag.

Example E3.2 and FIG. 6 accomplish the same as E3.1 and E3.3, with E3.2 having the inverse translational order of the two proteins in the polycistronic construct as compared to E3.1 and E3.3. E3.2 also embodies stable O-glycosylation capacity (here *N. benthaminana*) lines, in which virtually any O-glycosylation target peptide may be transiently expressed and O-glycosylated by the O-glycosylation machinery.

Example E4.1 demonstrates expression of the MUC1 target peptide both stably (*Arabidopsis*, duckweed) and transiently (*N. benthamiana*). Mass spectrometric analysis of MUC1 of stable *Arabidopsis* demonstrates that the targets are not post translationally modified in host cells according to the invention.

Example 4.2 provides evidence for the effect on level of expression of the target MUC peptide of using fusions with arabinogalactan protein sequences. A positive effect was observed in transiently expressed in *N. benthamiana*.

Example 4.6 demonstrates the transfer of GalNAc to the target MUC1 peptides linked to yellow fluorescent protein (YFP). 4.6.1 regards expression in example E3.1 background followed by analysis by Western using *Vicia villosa* lectin (VVA), which is specific to GalNAc rather than an antibody plus a pair of monoclonal antibodies specific to the naked peptide and the peptide with GalNAc residues, respectively. Example 4.6.2 demonstrates transient expression of the MUC1-YFP chimeric construct transiently in the moss *Physcomitrella patents*. Analysis using immunolabeling of fixed cells with the antibodies of the preceding example.

Example 4.6.3 analyses the products of the products described in the foregoing examples. Mass spectrometric analysis proves that MUC1 peptides are produced with 1, 2 and 3 GalNAc residues and that it can be raised to 4 GalNAc residues in host cells that co-express UDP-GalNAc-transferase T4 (which transfers to different residues on the peptide than does T2).

Examples 4.6.4 and 4.6.5 generalize the above findings to the E3.3-background, i.e. where the epimerase is targeted to the Golgi (E4.6.4) and where O-glycosylation has been accomplished from a single construct (4.6.5), both using transiently and stably transformed host cells.

Example 4.7 and FIG. 17 demonstrate that exchange of the translational order of the carrier (YFP) and target MUC1 peptides do not affect the expression level or glycosylation state or stability of the fusion target proteins in both transiently and stably transformed host cells systems.

Example 4.8 and FIG. 18 demonstrate that target MUC1 peptides embedded within a carrier protein (here GFP) has retained its substrate specificity for the O-glycosylation machinery in both transiently and stably transformed host cells systems.

Example 4.9 and FIG. 19 demonstrate, both in stably transformed BY-2 suspension cells and transiently transformed *N. benthamiana*, that another mucin, MUC16 is also expressed and GalNAc'ylated in an E3.1 background.

Example 4.10 further generalizes the invention to non-mucin targets using interferon α2B in a chimeric construct with an arabinogalactan protein module in an E3.1 background as in the previous example.

Example 5 regards co-expression of MUC1 target peptide along with the T2 GalNAc-Transferase, but no epimerase. No glycosylation of the target peptide is observed. The example demonstrates firstly that the epimerase is essential and secondly that the plant's own post-translational machinery does not take over. Rather, the naked target peptide is produced (as was already demonstrated in example 4.1).

Example 6 addresses pool-sizes of the essential UDP-GalNAc by demonstrating stimulation of GalNAc glycosylated MUC1 under e.g. example E3.1 conditions but with co-expression of the nucleotide sugar transporter hUGT1 from *Homo sapiens*.

a) ABBREVIATIONS

35S, CaMV Cauliflower mosaic virus promotor and terminator;
AGPs, arabinogalactan proteins;
C, C-terminal tags;
CDS, Coding sequence;
CGM, C-terminal GlycoModule and tags;
ESI-MS, Electrospray ionisation-mass spectrometry;
F, Flag tag ((M)DYKDDDD);
GalNAc-T2, GalNAc-transferase T2;
GalNAc-T4, GalNAc-transferase T4;
GM, Glyco Module;
Goi, gene of interest;
Gol, Cytoplasmic tail, TMD and stem region of Golgi anchored *H. sapiens* GalNAc-T2;
hPod=human podoplanin;
INF α2B, Interferon α2B;
N,N-terminal tags;
GalNAc, N-acetylgalactosamine
MALDI-TOF MS, Matrix-assisted laser desorption/ionization time-of-flight mass spectroscopy;
NGM, N-terminal GlycoModule and tags;
NOS, nopaline synthase of *Agrobacterium tumefaciens*;
Pro, Promotor;
pCAMBIA, pC;
PTMs, Post Translational Modifications;
RC, Reverse Complement;
SP, Signal peptide;
T2, polypeptide GalNAc-Transferase T2
Term, Terminator;
Transferase, T;
Ubi, Ubiquitin promotor and terminator of the *Nicotiana tabacum* Ubi. U4 gene;
UDP, Uridine-di-phospho-;
Yfp, Yellow fluorescence protein;

b) DEFINITIONS

MUC1 shall, for the purposes of the present invention, mean nucleotide sequences as well as the encoded amino acid sequence comprising repeats the 20 highly conserved amino acid residues: HGVTSAPDTRPAPGSTAPPA (Tarp et al. 2007). The number of repeats need not be integer and the repeats may be flanked or interspersed with sequences that aid targeting, secretion, purification, presentation of the antigenic epitopes to the immune system, or combinations thereof. Variants at the nucleotide level that are codon optimized for the plant host cell are embraced by the definition.

Each repeat contains 3 threonine and 2 serine residues (underlined) which all are potential O-glycosylation sites.

The modular structure comprising repeats is a defining feature of the class of mucins. The worker skilled in the art will thus readily generalize the MUC1 construct definition to the other mucins and thus be able to derive e.g. vaccine candidates from their amino acid sequences.

The word "target" is used generically for the polypeptide to be glycosylated, be it MUC1, or other candidate therapeutic proteins with acceptor sites for O-glycosylation.

GalNAc-Transferase shall mean any transferase catalyzing the addition of a GalNAc to a serine or thereonine residue of a given peptide. Suffixes will denote particular genes/enzymes. The different human GalNAc-Transferases have different specificities when a 20 amino acid MUC1 TR is used as protein substrate. In vitro studies have shown that GalNAc-T1-3 and T11 can use unglycosylated MUC1 target where GalNAc-T4 preferentially use preglycosylated MUC1 as target (Sorensen et al. 2006; Tarp & Clausen 2008).

In the present invention GalNAc-T2 (amino acid sequence posted under accession number NP_004472.1) has been used partly to produce the appropriate Tn cancer glycoform of MUC1 (Tarp et al 2007, Bennett et al. 1998). Production of the complete appropriate Tn cancer glycoform of MUC1 will be obtained by the introduction of the GalNAc-T4 isoform (acc no. NP_003765.2: Bennett et al. (1998)). Fifteen human GalNAc-T genes have been cloned and functionally expressed and additionally five putative GalNAc-T genes have been identified (Kato et al. (2006), Hassan et al. (2000), Ten Hagen (2005)). The twenty isoforms share 40-80% sequence identify and are grouped in CAZy-family GT27. Human glycosyltransferases, GalNAc-Ts included, are as a rule targeted correctly to the secretory pathway and are retained correctly in plant cells.

GalNAc-Ts included, are as a rule targeted correctly to the secretory pathway and are retained correctly in plant cells. This may not always apply, and in particular will not apply to many microbial gene products. Localization may alternatively be accomplished using signal sequences from plants or signal sequences with already known functionality in plant cells. Workers skilled in the art will know how to design chimeric constructs and thus amend GalNAc-Transferases with the appropriate targeting/retention signals. Variants at the nucleotide level that are codon optimized for the plant host cell are embraced by the definition.

UDP-GalNAc epimerase define the class of enzymes that catalyze the interconversion of UDP-GlcNAc and UDP-GalNAc. They are C4'-epimerases which, with overlapping specificities catalyse epimeration at C4' of UDP-Glc, UDP-GlcA and UDP-GlcNAc. That is an enzyme which is annotated as a UDP-Glc:UDP-Gal epimerase for example will have some activity towards UDP-GlcNAc as well. The epimerase is not anchored to e.g. the ER or Golgi membranes; nor is it known to be part of a protein complex with the GalNAc-Transferase or with a nucleotide-sugar transporter. This activity may be targeted to the cytoplasm or to the secretory pathway as a soluble protein or it may be deliberately engineered to be retained using methods that are well known in the art. The epimerase may in most cases be sourced rather freely from a wide range of organisms and is thus defined by its biochemical activity and the definition embraces nucleotide sequences appropriately engineered to allow for expression in a plant host cell. Workers skilled in the art will understand how to select epimerase activities of various eukaryotic origins comprising but not limited to *Homo sapiens* GALE (Acc no Q14376), bird (XP_417833.2), fish (NP_001035389.1) insect (NP_612044.1), yeast (NP_596043.1). It is documented in the present invention that a prokaryotic epimerase may be used by in casu the WbpP gene of *Pseudomonas* encoding the amino acid sequence of accession number AAF23998.1

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, mosses and various classes of algae, comprising but not limited to prasinophytes, chlorophytes and charophyacean green algae.

Plant-based production systems may be comprised of intact, autotrophic plants grown in soil or another substrate or the intact plant may be grown either heterotrophically or autotrophically in aseptic in vitro culture. Such in vitro systems for culturing intact organisms have been developed for *Lemna* (angiosperm), *Physcomitrella* (moss) and several species of algae; and may readily be adapted to other species. Plant-based production systems may also be comprised of cells or tissues isolated from a multicellular plant and cultured in vitro. Tobacco BY-2 cells will used to exemplify this type of production systems, but tissue and suspension cultures can in general be established from any multicellular plant.

The terms "nucleic acid" and "polynucleotide" are used synonymously and refer to a single or double-stranded polymer of deoxyribonucleotide or ribonucleotide bases read from the 5' to the 3' end. The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences that may be introduced to confirm with codon preference in a specific host cell.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is capable of initiating transcription in most environmental and developmental conditions and in nearly all tissue types, whereas a "tissue-specific promoter" initiates transcription only in one or a few particular tissue types. An "inducible" promoter is a promoter that is active under environmental or developmental regulation. The term "operably linked" refers to a functional linkage between a nucleic acid expression control sequence (such as a promoter) and a second nucleic acid sequence, the gene of interest, wherein the expression control sequence directs transcription of the nucleic acid corresponding to the second sequence.

The product encoded by the gene of interest will often comprise a signal peptide, which is a short (typically 3-60 amino acids long) peptide chain that directs the transport of a protein. Signal peptides may also be called targeting signals and signal sequences. Targeting to the secretory pathway are of particular relevance to the present invention, and here signal peptides are N-terminally located sequences usually comprising at least five hydrophobic amino acids. Targeting to the secretory pathway in a plant cell may be accomplished using both mammalian and fungal signal peptides as well as plant-derived signals. The gene of interest may thus encode a chimeric protein.

Techniques for transformation are well known and described in the technical and scientific literature. They vary by organism such that stable integration of the gene constructs in angiosperms is preferably carried out by particle bombardment or by *Agrobacterium* mediated transformation whereas homologous recombination is used for some algae and mosses. Workers skilled in the art will readily appreciate that once homologous recombination becomes practical in angiosperms, new strategies for transformation becomes realistic such as having the coding sequence of interest controlled by an endogenous promoter.

c) COMPONENTS FOR ENGINEERED MUCIN-TYPE O-GLYCOSYLATION IN PLANTS

The core genes/constructs needed for implementation of mucin-type O-glycosylation are described in the following.
UDP-GalNAc Production—Expression of the Epimerase.

The freedom to employ UDP-GalNAc-epimerase sourced over large phylogenetic distances argued above is documented here using the wbpp gene which is part of the B-band LPS cluster in *Pseudomonas aeruginosa* O6 (GenBank accession number AAF23998.1, Belanger et al. 1999). Kinetic properties and substrate specificities of cytosolic *P. aeruginosa* WbpP are described in Creuzenet et al. (2000) and Demendi et al. (2005). A patent 'WbpP and a method for assay of WbpP' has been issued (U.S. Pat. No. 6,582,910). In order to employ various existing UDP-GlcNAc pools in the plant cell, the WbpP has, in the current invention, been expressed as a N-terminally Flag-tagged cytosolic, ER—and Golgi targeted single enzyme or co-expressed with the GalNAc-T2 enzyme.

A Golgi transporter for transporting cytosolic UDP-GalNAc into the Golgi apparatus is not specifically needed. Transport may be limiting, however, in which case introduction of a specific transporter may increase the O-glycosylation capacity. The inventors will therefore additionally express the human UDP-Gal and UDP-GalNAc-Transporter (hUGT1) (Segawa et al. 2002) as part of the machinery for O-glycosylation capacity.
UDP-GalNAc-Transporters—Optimization of Golgi Lozalized UDP-GalNAc Pool.

UDP-GalNAc-Transporters are well-known integral membrane proteins that transport UDP-GalNAc synthesized in the cytoplasm into the secretory pathway. *Homo sapiens* UGT1 (Acc P78381-2) and UGT2 (Acc P78381-1) of the most studied examples of transporters that are useful in the present inventions. Other examples may be found among birds (e.g. NP 001026445.1) nematodes (NP 493723) and insects such as the fruitfly DmUGT (AB055493).
Expression of GalNAc-T2.

Successful engineering of mucin-type O-glycosylation machinery depends correct localization to the Golgi. The inventors have shown that fungal signals (Sorensen et al. 2000) as do Golgi targeting sequences from mammals (Skjøt et al 2002) work in plants. Our results agree with those of other workers leading to the general conclusion that signals for Golgi retention are generally understood across eukaryotic kingdoms and GalNAc-T2 is therefore expressed as the native full length Golgi targeted enzyme and Golgi targeted WbpP is expressed with the N-terminal cytoplasmic tail, TMD and stem region of GalNAc-T2 fused to the N-terminus of WbpP to enable co-localization with GalNAc-T2 in the Golgi apparatus. In this invention co-expression of these various WbpP's and full length native GalNAc-T2 are designated mucin-type O-glycosylation capacity (Cf. C3 and E3).

Expression of Targets with Mucin-Type O-Glycosylation Sites for Secretion Via the Secretory Pathway.

The mucin targets MUC1-3.5TR & MUC161.2TR and the mucin-type O-glycosylation site containing protein therapeutics human interferon α2B (hINF α2B), and podoplanin (hPod), have been N-terminally fused with various plant and fungal signal peptides for targeting to the secretory pathway. The targets have in addition fused affinity and antigen tags, and in some cases, additional glycomodules for enhanced secreted expression levels targeted at the endogenous plant O-glycosylation machinery (Xu et al. 2007).

The Plant Host Cells.

Production in plant cells may manifest itself in several different ways, each of which has its advantages. Aseptic production can be accomplished using cells cultured in vitro or whole plants for which sterile culture systems have been developed. Most practical of the latter category are members of the duckweed genus (Lemnaceae). Plant biotechnologists will realize that algae constitute a single cell alternative to aseptically grown duckweed. Expression in intact plants, field grown or cultivated in glasshouses or climate chambers, may either accomplished by transient or stable expression and it may be accomplished using constitutive expression or expression in particular organs, such as, but not limited to: tubers, seeds, fruits and photosynthetic tissues. Three plant expression systems are documented in the present invention: Mucin-type protein O-glycosylation has been accomplished transiently in Tobacco leaves and stably in Tobacco suspension culture BY-2 cells (higher plant, liquid based), *Arabidopsis thaliana* (higher plant, soil-grown) and partly in Duckweed (higher plant, liquid based). In present invention GalNAc-T2 and optionally -T4 have been used to produce the appropriate Tn cancer glycoform of MUC1 (Tarp et al 2007, Bennett et al. 1998). Certain tissues in multicellular systems are better suited to protein accumulation than others. Most notable are seeds and grains, which both offer cellular systems for protein accumulation and a system for dehydrated, stable storage. EP1668137, for example, discloses a method for accumulation heterologous protein at the expense of the native seed storage proteins in grains of barley. Such strategies are readily applicable to the present invention and workers skilled in the art will know how to generalize the method and select promoters and targeting sequences to accomplish accumulation of the heterologous protein in particular cells and organelles.

d) MATERIALS AND METHODS

Plant Cell Factories

*Lemna minor* is obtained from United States Department of Agriculture—APHiS, Plant Protection and Quarantine, 4700 River Road, Unit 140, Riverdale. Md. 20737. Transformation, cultivation and fermentation are done in accordance to Yamamoto et al (2001).

Tobacco Bright Yellow 2 (BY-2) suspension cells are cultivated, transformed and fermentation in accordance to Mayo et al. (2006). In accordance to (Lee et al. 2002), 2% gelatin was occasionally added as an additive.

Transformation, Inoculation and Growth Conditions of *A. thaliana* and *N. benthamiana*

*Agrobacterium tumefaciens* strain C58C1 pGV3850 was used for both stable transformation and transient *agrobacterium* mediated expression. Transformation is described in Horsch et al. (1985). Growth conditions for transgenic *Arabidopsis thaliana* plants are described in Egelund et al. (2007).

DNA Constructs for Plant Transformation and Transient Expression

Open source vectors used for transient *Agrobacterium* mediated expression and stable transformation in the present invention are:

pBI121 (genbank acc no AY781296)
pCAMBIA 2300 (genbank acc no AF234315)
pCAMBIA 1302 (genbank acc no AF234298)

For legacy of open source pCAMBIA binary vectors see http://www.cambia.org.

pPS48 is an intermediate *E. coli* only vector, which contains a cassette with the 35S promotor, a MSC and the 35S terminator (Odell et al. 1985), where the gene of interest (goi) is cloned in front of the 35 promotor using the MSC and the entire transcriptional unit (35S-Pro-goi-35S-term) is excised using XbaI or HindIII. pPS48 is a generous gift from Poul Erik Jensen, Faculty of Life, Copenhagen University.

Modified public domain vectors used for transient *Agrobacterium* mediated expression and stable transformation in the present invention is:

pC1302D 39 bp of the MSC of pCAMBIA1302 (9736-9792) was deleted leaving the SphI and HindIII sites resulting in the sequence gaattggcatgcaagctt (SphI and HindIII are underlined) yielding pC1302D.

pC2300D

Similar to the construction of p1302D, the MSC of pCAMBIA2300 was deleted leaving the SphI and HindIII sites, yielding pC2300D

*Nicotiana tabacum* Ubiquitin Promotor and Terminator Regions

*Nicotiana tabacum* Ubi.U4 gene (Genbank acc no X77456, Genschik et al. (1994)). Ubi.U4 gene derived promotor is pos 567-1360 (UbiPro) and Ubi.U4 gene derived terminator is pos 2401-2785 (UbiTer) in X77456, respectively. UbiPro is flanked with 5'-aagcttctagaggtacc-3' (HindIII, XbaI, KpnI) at the 5' end and with 5'-gagctccatgg-3' (SacI, NcoI) in the 3' end. UbiTer is flanked with 5'-gagctcgtcgacggtaacc-3' (SacI, SalI, BstEII) at the 5' end and with 5'-gcatgctctagaagctt-3' (SphI, XbaI, HindIII) in the 3' end.

35S Promoter and Terminator Sequences of pCAMBIA and pPS48 Derived Cassette

Cauliflower mosaic virus (CMV) 35S promoter (35SPro) and terminator (35STerm) sequence are derived from (Odell et al. 1985, GenBank Accession no X05868 and V00140).

Signal Peptides (SP)

*Aspergillus aculeatus* Rhamnogalacturonan acetylesterase [CAA61858] Kauppinen et al. (1995)
AaSP: MKTAALAPLFFLPSALA

*Oryza sativa* (japonica cultivar-group) alpha-amylase (CAA39778)
OsSP: MAKHSTTMSC LLFFVLLCLG SHLAQA/QV

*Physcomitrella patens* aspartic protease (ASP) (EMBL acc. No. AJ586914) (Schaaf et al. 2005)
PpSP: MGASRSVRLAFFLVVLVVLAALAEA NtSP: *Nicotiana tabacum* proline-rich protein 3 (UniProt acc no T03236, Q40502)
MGKMASLFASLLVVLVSLSLA AtSP: *Arabidopsis thaliana* Basic Chitinase (UniProt Q9SXJ4) (Samac et al. 1990)
MGKTNLFLFLIFSLLLSLSSA

*Nicotiana tabacum* extensin precursor (Q40502_TOBAC) NtSP2: MGKMASLFATFLVVLVSLSLA The SPs were codon-optimized with 1. organism: *Nicotiana tabacum* and 2. organism: *Arabidopsis thaliana*.

Enzymes, Genes and Constructs

The Epimerase pET23-WbpP (Creuzenet et al. 2000) was a generous gift from Joseph S. Lam (Dept of Microbiology, University of Guelph, Guelph, Ontario N1G 2W1, Canada).

The GalNAc-Transferases

Sequence of *Homo sapiens* UDP—N-acetylgalactosaminyltransferase transferase T2 and T4 (GalNAcT2 and -T4) are described in White et al. (1995), Bennett et al. (1998) and U.S. Pat. No. 6,465,220—Glycosylation using GalNAc-T4 transferase.

BvT2: N-terminal His- and T7 tagged GalNAc-T2 (pAcGP67A-GalNAc-T2-sol) is cloned, expressed in insect *Spodoptera frugiperda* 21 (Sf21) cells and purified as described in: Bennett et al. (1996), Glycosylation using GalNAc-T4 transferase—U.S. Pat. No. 6,465,220, pred. MW 58.000 Daltons.

Peptides and Proteins Targeted for O-Glycosylation

EcMUC1-3.5TR: MUC1-3.5TR(P15941) was cloned in pET28, yielding MUC1-3.5TR-pET28, and transformed into *E. coli* BL21(DE3) cells. 100 ml cultures of were inoculated and grown ON to a density of $OD_{600}$ 0.6 where after protein expression was induced by adding Isopropyl β-D-1-thiogalactopyranoside (IPTG) to a final conc of 0.15 mM and incubated for 5 h, 37° C., 200 RPM. Briefly, the cells were spun down, resuspended in 10 mL 50 mM Na—$PO_4$, 250 mM NaCl, 8 M Urea, pH 8.0), subjected to sonication using a Branson Model 450 sonifer, 2 times for periods of 30 sec (power set to 5). The sonicated fraction was spun at 20,000 g, 4° C., 10 min and the supernatant recovered. His-Tag purification of EcMUC1-3.5TR from the supernatant was done under denaturation conditions including 8M Urea using Ni-NTA beads in accordance to manufacturers recommendations (The QIAexpressionist™, Qiagen).

Monoclonal Antibodies for Use in Analysis

Monoclonal antibodies for detailed characterization of subcellular localization of enzymes used in this invention are described in Rottger et al. (1998) and Mandel et al. (1999). Antibodies that specifically binds GalNAc-glycosylated MUC1 product (Tn) are described in Tarp et al. (2007) and Sorensen et al. (2006).

Mouse 5E10 anti MUC1+/−GalNAc (epitope) mAb
Mouse 5E5 anti GalNAc-decorated MUC1 (epitope) mAb
Mouse 6B7 anti *H. sapiens* GalNAc-T2 GalNAc (epitope) mAb
Mouse 4C4 anti *H. sapiens* GalNAc-T2 GalNAc (epitope) mAb
Mouse 5B3 anti *H. sapiens* GalNAc-T4 GalNAc (epitope) mAb
Mouse M11 anti *H. sapiens* Mucin 16 (epitope) mAb
Mouse anti *P. aeruginosa* WbpP PAb raised against His-purified *E. coli* $(H)_6$WbpP
*Vicia Villosa* lectin, HRP conjugated *Vicia Villosa* (VVA) lectin is from EY laboratories, San Mateo, USA and binds GalNAcα1, O-Ser/Thr ($T_n$-antigen) blotting and development, was carried out in accordance to Wandall et al. (1997).

Western Positive Control Proteins

T7-control: T7-positive control (31.1 kDa) was from Roche.

BAP: Amino-terminal Bovine Serum Albumin Protein Met-FLAG (BAP) (468 a.a., 49.4 kDa) was from Sigma-Aldrich.

Standard PCR Conditions:

PCR is performed in 50 μl reaction volumes using the Expand High Fidelity system (Roche) with the touchdown cycle parameters: 3 min 97° C. (Denaturation), 20 cycles: 94° C. for 30 s, 68° C. for 30 s (with decrease of 0.5° C. after each cycle) and 72° C. for 1', then 10 cycles: 94° C. for 30 s, 58° C. for 30 s and 72° C. for 1' followed by 5 min at 72° C. All PCR amplifications are cloned into the pCR®2.1 vector using the TOPO-TA cloning kit (Invitrogen) and the authenticity of the inserts was verified by sequencing, before the final cloning into the end vector.

Expression and Purification of EcWbpP for Production of a Mouse Polyclonal Ab (pAb)

His tagged pET23-$(H)_6$wbpp (Creuzenet et al. 2000) was transformed into *E. coli* BL21(DE3) cells. 100 ml cultures of were inoculated and grown ON to a density of OD600 0.6 where after protein expression was induced by adding Isopropyl β-D-1-thiogalactopyranoside (IPTG) to a final conc of 0.15 mM and incubated for at 5 h, 30° C., 200 RPM. Briefly, the cells were spun down, resuspended in 10 mL of native buffer (50 mM Na—$PO_4$, 250 mM NaCl pH8.0), subjected to sonication using a Branson Model 450 sonifier, 2 times for periods of 30 sec, power set to 5. The sonicated fraction was spun at 20.000 g, 4C, 10 min and the supernatant recovered. His-Tag purification of EcWbpP from the supernatant was done under native conditions (50 mM Na—$PO_4$, 250 mM NaOH, pH 8.0) out using Ni-NTA beads in accordance to manufacturers recommendations (The QIAexpressionist™, Qiagen).

Generation of Polyclonal mouse Ab against EcWbpP was performed by immunizing mice with 5-10 μg recombinant expressed and purified protein as previously described (Mandel et al. 1999) and collection of blood by tail bleed 10 days after last boost.

*Agrobacterium* Mediated Transient Expression in *Nicotiana benthamiana* Leaves

*Agrobacterium* mediated expression was done essentially according to the method devised by Sainsbury and Lomonossoff (2008). 3-4 week old *N. benthamiana* plants were inoculated Agrobaterium containing the construct(s) in question and left for 6 days, where after proteinacious leaf extracts were prepared as described in the section 'Preparation of leaf extracts'.

Preparation of BY-2 Protoplasts 1 ml of BY-2 cells in exponential phase was pellet gently (150×g) then resuspended in 1 ml EB (25 mM MES, pH 5.5, 2 mM $CaCl_2$, 600 mM mannitol) containing 0.25% macerozyme (Yakult Honsha Co. Ltd., Japan) and 1% cellulase (Yakult Honsha Co. Ltd., Japan) and incubated for >=2 h with mild shaking (45 rpm). The suspension was then pelleted (150×g, RT) and resuspended in 0.5 ml EB. Generation of intact protoplast was checked—either visually (round spherical cells) or with 0.01% Calco flour white (which stains the cell wall) in distilled water for 2 sec to 2 min, then washed briefly in water.

Immunostaining of BY-2 Protoplasts

Protoplasts were dried onto Teflon printed diagnostic slides (Immuno-Cell Int., USA). Dried protoplasts were acetone fixed at −20° C. for 8 min's and airdried 1 h at room temperature. Protoplast permeabilization was done with 5% BSA incl. 0.2% saponin for 20 min's at room temperature. Slides were overlaid with primary antibody over night at 4° C. Slides were incubated with secondary fluorephore labeled secondary antibodies for 45 min's at room temperature. All washing steps between procedures were done with 1×PBS. Finally slides were mounted with fluoromount anti fade and imaged.

Preparation of Leaf Extracts

Freshly harvested leaves is frozen in liquid $N_2$ and comminuted using a pestle and mortar with 2 ml extraction buffer A (50 mM Na—$PO_4$, 250 mM NaOH, 5 mM Imidazol, pH8.0) containing Complete Proteinase Inhibitor (Roche) and 1 mM phenylmethanesulfonylfluoride (PMSF) per g tissue (fresh weight). The sample is incubated for 10 min. on ice and insoluble material pelleted by centrifugation (20,000×g) for 10 min., the supernatant is recovered and stored at −20° C.

Preparation of Plant Total Microsome Fraction

Freshly harvested leaves were crushed by a polytron for 30 sec, in (1 g leaves/3 ml microsome extraction buffer) microsome extraction buffer (50 mM Potassium Phosphate buffer, pH 7.2, 400 mM sucrose, 100 mM sodium ascorbate, 1 tablet of proteinase inhibitors (Roche)). The sample was then cleared by a pre-centrifugation at 1000×g for 10 min, 4° C., and total microsome was obtained by a 50 K rpm centrifugation, 1 hr, 4° C., using a Beckman Ultra SW70 Ti centrifugator.

SDS-PAGE and Western Blot

Leaf and cell suspension culture extracts were subjected to SDS-PAGE and Western Blot analysis were essentially done as described in Petersen et al. (2009). Primary antibodies 5E10 and 5E5 (cf below) in the form of unpurified hybridomas cell secrete were used for detection of MUC1-3.5TR target peptides. Primary antibodies 6B7 (western, denatured conditions) 4C4 (immunostainings, native conditions), in the form of unpurified hybridomas cell secrete, were used to detect GalNAc-T2. Detection of Flag-tagged WbpP on western blots is described in Petersen et al. (2009).

His-Tag Purification 50 ml cleared supernatant was incubated with 0.5 ml of Ni-NTA agarose beads (Qiagen) for 2 h, 4° C., under gentle rolling, then the beads were washed, 10 min with 20 ml of wash-buffer (50 mM Na—$PO_4$, 250 mM NaOH, 20 mM Imidazol, pH 8.0). His-tagged proteins were eluted from the beads using elution buffer (50 mM Na—$PO_4$, 250 mM NaOH, 250 mM Imidazol, pH 8.0).

Purification of MUC1-3.5TR Expressed in Plants and *E. coli*

Eluate from Ni-NTA column was applied on a Thermo C18 column attached to a HP 1100 HPLC. Proteins were separated based on reverse phase condition. Solvent used in separation were: A, 0.1% TFA in water; B, 0.1% TFA in 90% Acetonitrile. The program was: constant flow of 10% of B for 5 min, 15 min with linear increase of B to 100%, followed by 5 min of constant wash in 100% B. 210 nm and 280 nm signals of eluate were recorded by a HP 1100 Diode Array Detector.

Sample Purification Using Zip-Tip Column

A Zip-Tip column attached to a 20 µl micropipet (Gilson's Pipetman P20) was pre-conditioned using 100% ACN and milli-Q water. The sample dissolved in 20 µL of 0.1% TFA was withdrawn through the column and desalted using 0.5% formic acid. The peptides were extracted with 0.5% formic acid in 1:1(v/v) water: ACN and 100% ACN into a 200 µL eppendorf tube for MS analysis.

Matrix Assisted Desorption Time of Flight (MALDI-TOF) Analysis of Mucin-Type Targets Structure of MUC1 is determined using MALDI-TOF according to Wandall et al. (1997). Peptides from HPLC fractions were lyophilized, and resolved in 20 µl water. All mass spectra were acquired on a Voyager-Elite MALDI time of flight mass spectrometer (Perseptive Biosystem Inc., Framingham, Mass.), equipped with delayed extraction. The MALDI matrix was 25 g/L 2,5-dihydroxybenzoic acid (Sigma-Aldrich) dissolved in a 1:1 mixture of water and methanol. Samples were prepared for analysis by placing 0.5 µl of sample solution on a probe tip followed by 0.5 µA of matrix. All spectra were obtained in the linear mode and calibrated using external calibration.

Endo-Asp Digestion of MUC-3.5TR and subsequent HPLC purification

Approximately 25 µg purified MUC1-3.5TR-YFP was incubated with 1 µg endoproteinase Asp-N from *Pseudomonas fragi* (Sigma-Aldrich, product code P3303) in a 300 L reaction containing 100 mM Tris-HCl pH 8.0, for 16 hours at 37° C.

HPLC was carried out on a Dionex system consisting of a P580 Pump Unit and an AS1 100 Automated Sample Injector. Prior to injection, trifluoroacetic acid (TFA) was added to each sample to a final concentration of 0.05% (v/v). 40 µL of digested MUC1-3.5TR-YFP, containing approximately 2.5 µg total protein, was separated by reverse phase HPLC on a 150×4.6 mm Jupiter Proteo C12 column (Phenomenex) with a 90 Å pore size, 4 micron particle size, pre-equilibrated with 0.05% TFA, and 5% acetonitrile, in degassed water. Chromatographic separation was carried out in a two eluent system where eluent A was 0.05% TFA in water and eluent B was 0.05% TFA in acetonitrile, and the pump speed was a constant 0.5 mL min$^{-1}$. From 0-5 min, the eluent was 5% B, from 5-35 min, eluent B increased in a linear gradient to 40%, and from 35-45 min eluent B increased to 100%. Eluted peptides were monitored by measuring absorbance at 215 nm wavelength on a Dionex UVD340S detection system, and fractions collected manually in volumes of 200 pt, corresponding to an elution period of 24 s. Samples were freeze dried prior to preparation for mass spectroscopy analysis.

Hydrophobic Interaction Chromatography (HIC)

NaCl was added to a final concentration of 3 M to cleared leaf total extract, and pH was adjusted to 8.0 using 1 M Tris. The solution was incubated at 4° C. for one hour, centrifuged at 25000×g for 30 min and the supernatant was loaded to 15 ml CL-4B phenyl Sepharose® (GE Healthcare, Buckinghamshire, UK) column, which was washed with 25 ml of 50 mM Tris, pH 8.0, 2 M NaCl. Proteins were eluted by a gradient of B (33%-100%) in buffer A (50 mM Tris, pH 8.0, 3 M NaCl) and buffer B (MiliQ $H_2O$), 10 min with a flow rate of 3 ml/min, using a ÄKTA FPLC system.

*Vicia Villosa* Agglutinin Lectin Affinity Purification

Eluents (10 ml) from HIC were pooled and exchanged into 1×PBS by adding (1 ml 10×PBS buffer) and transferred to tubes containing 400 µA *Vicia Villosa* Agglutinin (VVA) lectin argarose beads (Sigma-Aldrich L9388), prewashed 5 min in 5 ml 1×PBS, incubated 3 hours at 4° C. under gentle rotation. Washes were done using 10 ml 1×PBS for 15 min at 4° C. Beads were collected by centrifugation at 1000×g for 5 min and loaded to a home made column. Elution of lectin bound MUC1 3.5TR-yfp was carried out by 1.5 ml of 40 mM GalNAc in 1×PBS.

The use of the above general method may be understood by reference to the following non-limiting examples, which are subdivided into examples of DNA-vector constructs, referred to by the letter 'C', and examples of detected expressed protein, including downstream analysis, referred to by the letter 'E'. Examples of preferred embodiments are also summarized in Table 1 and 2.

e) CONSTRUCT (C) LISTING

The construct is trailed by the encoded protein sequences, listed in the bracket '(SEQ ID NO X, ... )'

C1 Constructs Generating Sub-Cellular Pools of UDP-GalNAc

C1.1 A Construct Generating Cytoplasmic UDP-GalNAc pC2300-35SPro-Fwbpp-35Sterm (SEQ ID NO 1)

Full length wbpp was PCR amplified using standard PCR conditions, pET23-WbpP as template and the primers: 5'-gagctcatggattacaaggacgacgac-gacaagcacgtggaattcgccatggttatgatgagtcgttatgaaga-3' (PBY7For) and 5'-agcgctaggcctgagctc tca tttcaaaaacatgatgta-3'(PBY7Rev; SEQ ID NO 12), where underscoring designates SacI, PmII, EcoRI, NcoI, StuI & AfeI, italicized letters designates the Flag-tag sequence ((M)DYKDDDDK; SEQ ID NO 60), bold designates the 5' and 3' end sequence of Fwbpp, stop codon is bold and italicized. The PCR fragment was digested with SacI and sub-cloned into the SacI site of pPS48, a clone with the correct orientation with respect to the 35S promotor and 35S terminator sequence of pPS48 was obtained and the entire transcriptional unit (35SPro-Fwbpp-35STerm) was excised by HindIII and cloned into the MSC-HindIII site in pC2300, yielding pC2300-35SPro-Fwbpp-35Sterm (C1.1.).

C1.2 A construct generation ER localized UDP-GalNAc pC2300-35SPro-AaSP-FwbppKDEL-35STerm (SEQ ID NO 2)

Full length wbpp with was PCR-amplified using standard PCR conditions, pET23-wbpp as template and the primers: 5'-gagctcATGAAGACTGCTGCTTTGGCTC-CTTTGTTTTTTTTGCCTTCTGCTTTGGCT gattacaag-gacgacgacga-3' (PBY12For; SEQ ID NO 23) and 5'-agcgctaggcctgagctctcatagctcatctttcaaaaacatgatgtacc-3' (PBY12Rev; SEQ ID NO 61) where underscoring designates SacI, StuI, AfeI & SacI, italicized designates the Flag-tag sequence (DYKDDDDK), capital letters *A. aculeatus* signal peptide (AaSP), bold designates 5' and 3' sequence end of wbpp, ER retention signal KDEL bold and underscored, stop codon bold and italicized. The PCR fragment was digested with SacI, isolated and sub-cloned into the SacI site of pPS48 and the entire transcriptional unit (35SPro-Fwbpp-35STerm) was excised by HindIII, isolated and inserted into the MSC-HindIII site of pC2300, yielding pC2300-35SPro-AaSP-FwbppKDEL-35STerm (C1.2.).

C1.3 A Construct for Generation Golgi Localized UDP-GalNAc pC2300-35SPro-FT2Golwbpp-35STerm (SEQ ID NO 3)

PCR amplification and cloning of T2-anchor-stem-region: 5' end of human GalNAc-T2, comprising 5'cytoplasmic tail, cytoplasmic tail, TMD and stem region (1-414 bp 5'-atgcg-gcggcgctcg . . . gatctgccggccacc-3, 'MRRRS . . . DLPAT', Genbank acc no. X85019) was PCR amplified using a full length cDNA clone as template (unpublished), standard PCR conditions, and the primers: 5'-cacgtggaattcgccatggttatgcg-gcggcgctcgcggatgct-3' (PT2anchorFor; SEQ ID NO 32) and 5'-cgactcatcatggtggccggcagatccacccg-3' (PT2anchorRev; SEQ ID NO 33) where underscoring designates PmII, EcoRI & NcoI and Topo-TA cloned in pCR2.1TA (Invitrogen) yielding pCR2.1TA-Golwbpp.

PCR amplification and cloning of wbpp: Full length soluble wbpp with was amplified by PCR using standard PCR conditions, pET23-wbpp as template and the primers: 5'-5'-gccggccacc (3' end of T2Stem) atgatgagtcgttatgaagagc-3' (PwbppFor; SEQ ID NO 62) and 5'-agcgctaggcctgagctc tcatttcaaaaacatgatgtac-3' (PwbppRev; SEQ ID NO 63) where underscoring designates AfeI, StuI & SacI and Topo-TA cloned in pCR2.1TA, yielding pCR2.1TA-wbpp.

Golwbpp fusion was obtained by recombinant PCR using the primers PGolFor and PGolRev yielding the fragment Golwbpp. An N-terminal Flag-tag was introduced by replacing wbpp of pC2300-35SPro-AaSP-FwbppKDEL-35STerm with FGolwbpp using the using PmII and BstEII yielding pC2300-35SPro-Golwbpp-35STerm (C1.3).

C2 Constructs Conferring Golgi Targeted Polypeptide: GalNAc-Transferase Activity C2.1 Construct Encoding Secreted MUC1-3.5TR and Golgi Targeted GalNAc T2 pC1302D-35SPro-AaSP-MUC1-3.5TR-35STerm, 35SPro-T2-35STerm (SEQ ID NO 4, SEQ ID NO 5)

The NcoI-BstEII-Yfp fragment was excised from pC1302D-35SPro-AaSP-MUC1-3.5TR-35STerm, A double stranded oligo-linker was inserted into the NcoI/BstEII site of pC1302D, resulting in a deletion the NcoI site and introduction of a StuI site. Full length GalNAc-T2 (Genbank acc no. X85019) was excised from an existing PBKS plasmid with EcoRI, blunt ended and inserted into the StuI site thus leaving GalNAc-T2 under the control of 35S promotor and terminator sequence of pC1302D-35SPro-AaSP-MUC1-3.5TR-35STerm (C2.2) yielding pC1302D-35SPro-AaSP-MUC1-3.5TR-35STerm, 35SPro-T2-35STerm (C2.1) (promotor-5'CDS (ccatccggatccgaattctgcagagctcatg . . . ; SEQ ID NO 64, where underscoring designates BamHI, EcoRI, PstI and SacI, italics and bold designate 3'promoter sequence and 5'CDS, respectively) and 3' CDS-terminator sequence ( . . . taggaac-ctagcgctggtgacc agctcga; SEQ ID NO 65, where underscoring, bold and italics designate BstEII and 3'stop codon of CDS and 5'end of pC1302D 35S terminator, respectively).

C2.2 Construct Encoding Golgi Targeted GalNAc T2 pC1302D-35SPro-T2-35STerm (SEQ ID NO 5)

The HindIII-flanked SPro-AaSP-MUC1-3.5 TR-35STerm fragment of pC1302D-35SPro-AaSP-MUC1-3.5TR-35STerm, 35SPro-T2-35STerm (C2.1.) was excised and re-ligated, yielding pC1302D-35SPro-T2-35STerm.

C2.3 Construct Encoding Golgi Targeted GalNAc T4 pBI121-35SPro-T4-NosTerm (SEQ ID NO 6)

Human GalNAc-T4 (Y08564) was PCR amplified using standard PCR conditions, pcDNA-T4 (Bennett et al. 1998) as template, and the primers: P-T4For (SEQ ID NO 36): 5'-GGATCCACGCGTAAAATGGCGGTGAG-GTGGACTTGGGC-3', P-T4Rev (SEQ ID NO 37): 5'-GGATCCCTATTTCTCAAAACTCCAAATTTGA-3', yielding fragment BamHI-T4-BamHI, subcloned in to pCR2.1-TA and inserted into the BamHI site of pBI121, yielding pMI21-35SPro-T4-35STerm.

C3 Constructs Conferring Mucin-Type O-Glycosylation Capacity

C3.1 Construct Encoding Polycistronic HA Tagged Golgi Targeted GalNAc-T2 and Cytosolic Epimerase pC1302-35SPro-HAT2-2A-Fwbpp-35STerm (SEQ ID NO 7)

PCR amplification and cloning of HAT2: Heme Agglutenin (HA) N-terminally fused to GalNAc-T2 (HAT2) was PCR amplified using standard PCR conditions, GalNAc-T2 (C2.1) as template and the primers: P-HAT2For (SEQ ID NO 38): 5'-ggcttaaUatgtacccatacgacgtc-ccagactacgcccggcggcgctcgcggatgctgct-3' and P-HAT2Rev (SEQ ID NO 39): 5'-ACT TAAGCAAAUCAAAAT-TCAAAGTTTGACCAGAACCCTGCTGCAG-GTTGAGCGTGAAC-3', yielding the HAT2 fragment with uracil nucleotides at both ends.

PCR amplification and cloning of Fwbpp: Flag-tagged wbpp was PCR amplified using standard PCR conditions, pC2300-35SPro-Fwbpp-35Sterm (C1.1.) as template and the primers: PFwbppFor (SEQ ID NO 40): 5'-ATTTGCT-TAAGUTGGCAGGAGATGTGGAATCTAAC-CCAGGACCTATGGATTACAAGGACGACGACG-3', PFwbppRev (SEQ ID NO 41): 5'-ggtttaaU tcatttcaaaaacatgat- 3', yielding the Fwbpp fragment with uracil at both ends. The two fragments were cloned into the USER vector pC130035Su in accordance to Nour-Eldin et al. (2006) and Geu-Flores et al. (2007). HAT2 3'-end-2A-5' Fwbpp fusion is:

```
cgctcaacctgcagcag

T  L  N  L  Q  Q ggttctggtcaaactttgaattttgatttgcttaagttggcaggagatgtggaatctaacccagga
*cct*

G  S  G  Q  T  L  N  F  D  L  L  K  L  A  G  D  V  E  S  N  P  G  *P*

Atggattacaaggacgac (SEQ ID NO 66)

M  D  Y  K  D  D  (SEQ ID NO 67)
``` where italics designates the 2A sequence (Szymczak et al. 2004, El Amrani et al. 2004), 'P' the site of cleavage, 'MDYKDD . . . ' start of Flag tag, yielding pC1302-35SPro-HAT2-2A-Fwbpp-35STerm (C3.1.). HA sequence YPYD-VPDYA (Chen et al. 1993); Yfp was cloned from pC2300u vector (Nour-Eldin et al. 2006).

C3.2 Construct Encoding Polycistronic Cytosolic Epimerase and Golgi Targeted GalNAc-T2
pBI121-35SPro-wbppF-2A-T2-NosTerm (SEQ ID NO 8)

35SPro-wbppF-2A-T2 was PCR-amplified using standard PCR conditions, pBI121-35Pro-PpSP-MUC1-3.5TR-Yfp-2A-Golwbpp-2A-T2-NosTerm (C6.1.) as template and the primers: 5'-tctagaATGATGAGTCGTTATGAAGAGC-3' (PwbppFor; SEQ ID NO 68) and 5'-gagctcctactgctgcaggt-tgagcgt (PT2Rev; SEQ ID NO 69) were used to PCR-amplify the fragment wbppF-2A-T2-35STerm. This fragment was then inserted into pBI121 vector using the XbaI and SacI site, yielding pBI121-35SPro-wbppF-2A-T2-NosTerm.

C3.3 Construct Encoding Polycistronic Golgi Targeted GalNAc-T2 and Cytosolic Epimerase
p1302D-35SPro-T2-2A-Fwbpp-35STerm (SEQ ID NO 9)

The HindIII flanked 35SPro-AaSP-MUC1-3.5TR-Yfp (H)$_6$-35STerm cassette of pC1302D-35SPro-AaSP-MUC1-3.5TR-Yfp(H)$_6$-35STerm; 35SPro-T2-2A-FWbp (C6.2.) (cf below) was cut out by HindIII and re-ligated to yield p1302D-35SPro-T2-2A-Fwbpp-35STerm.

C3.4 Construct Encoding Cytosolic Epimerase and Golgi Targeted GalNAc-T2 from Separate Transcripts
pC1302D-35SPro-FWbpP-35STerm; 35SPro-T2-35STerm (SEQ ID NO 1, SEQ ID NO 5)

The XbaI-35SPro-FWbpP-35STerm-XbaI fragment was excised of pC2300-35SPro-Fwbpp-35Sterm (C1.1), and inserted into XbaI site of pC1302D-35SPro-T2-35STerm (C2.2.), yielding pC1302D-35SPro-FWbpP-35STerm; 35SPro-T2-35STerm.

C3.5. Construct Encoding Polycistronic Golgi Targeted Epimerase and Golgi Targeted GalNAc-T2
pBI121-35SPro-FT2GolWbpP-2A-T2-NosTerm (SEQ ID NO 11)

35SPro-FT2GolWbpP-2A-T2 was PCR-amplified using standard PCR conditions, pBI121-35Pro-PpSP-MUC1-3.5TR-Yfp-2A-Golwbpp-2A-T2-NosTerm (C6.1) as template and the primers: 5'-tctagaatggattacaaggacgacgac-gacaag-3'(PFlagFor; SEQ ID NO 43) and 5'-gagctcctactgctgcaggttgagcgt (PT2Rev; SEQ ID NO 42) were used to PCR-amplify the yielding fragment FT2Golwbpp-2A-T2. This fragment was then inserted into pBI121 vector using the XbaI and SacI sites, yielding pBI121-35SPro-FT2Golwbpp-2A-T2-NosTerm.

C4 Constructs Expressing Mucins and Other O-Glycosylation Target Peptides
C4.1 Construct Encoding MUC1-3.5TR with AaSP Signal Peptide
pC1302D-35SPro-AaSP-MUC1-3.5TR-35STerm (SEQ ID NO 4)

MUC1-3.5TR (P15941) was PCR-amplified using standard PCR conditions, pET28-MUC1-3.5TR as template and the primers: 5'-CtgcagATGAAGACCGCCGCTCTTGCAC-CGCTCTTCTTCCTCCCCTCTGCCCTCGC-CACTACTcacgtgcatcatcatcatcat-cacAgtagcggcctggtgccgcgcggcagccatatggctagcatgactggtgga cagcaaatgg gtcgggatccgaattctGTCACCTCGGC-CCCGGACACCAGGCCGGCCCCGGGCTCCACCGCCC CCCAAGCCCACGGT-3' (PBY9For; SEQ ID NO 44) and 5'-gagctcCTAGGTGTCCGGGGCCGAGGT-3' (PBY9REV; SEQ ID NO 45). The PCR fragment was digested with PstI and SacI, isolated and sub-cloned into the PstI-SacI site of pPS48 and the entire transcriptional unit (35SPro-AaSP-MUC1-3.5TR-35STerm) was excised by HindIII, isolated and inserted into the MSC-HindIII site of pC1302D, yielding pC1302D-35SPro-AaSP-MUC1-3.5TR-35STerm.

C4.2 Construct Encoding MUC1-3.5TR with OsSP Signal Peptide and C-Terminal Glycomodule
pC2300-UbiPro-OsSP-MUC1-3.5TR-CGM-35STerm (SEQ ID NO 13) Codon optimized (1. Organism: *Nicotiana tabacum*, 2. Organism: *Arabidopsis thaliana*) OsSP-MUC1-3.5TR-CGM (C-terminal GM and tags) flanked by UbiPro and 35STerm was synthesized and inserted into pUC57 by GenScript (USA Inc.), yielding pUC57-UbiPro-OsSP-MUC1-3.5TR-CGM-35STerm. UbiPro-OsSP-MUC1-3.5 TR-CGM-35STerm was excised by HindIII, isolated and inserted into the MSC-HindIII site of pC2300, yielding pC2300-UbiPro-OsSP-MUC1-3.5TR-CGM-35STerm.

C4.3 Construct Encoding MUC1-3.5TR with OsSP Signal Peptide and C-Terminal T7 and His Tag
pC2300-UbiPro-OsSP-MUC1-3.5TR-C-35STerm (SEQ ID NO 14)

pC2300-UbiPro-OsSP-MUC1-3.5TR-C-35STerm (C4.3) is derived from pC2300-UbiPro-OsSP-MUC1-3.5TR-CGM-35STerm (C4.2) where the PacI flanked (SP)$_{10}$ GM was excised and re-ligated.

C4.4 Construct Encoding MUC1-3.5TR with N-Terminal OsSP Signal Peptide and N-Terminal Tag T7 and his Tag
pC2300-UbiPro-OsSP-MUC1-3.5TR-35STerm) (SEQ ID NO 15)

Codon optimized (1. Organism: *Nicotiana tabacum*, 2. Organism: *Arabidopsis thaliana*) N-OsSP-MUC1-3.5TR (N-terminal tags) was synthesized GenScript (USA Inc.) and inserted into pUC57. The SacI-OsSP-MUC1-3.5TR-CGM fragment of pUC57-UbiPro-OsSP-MUC1-3.5TR-CGM-35STerm was replaced by the SacI-OsSP-MUC1-3.5TR fragment, yielding pUC57-UbiPro-OsSP-MUC1-3.5TR-UbiTerm35STerm. UbiPro-OsSP-MUC1-3.5TR-35STerm was excised by HindIII, isolated and inserted into the MSC-HindIII site of pC2300, yielding pC2300-UbiPro-OsSP-MUC1-3.5TR-35STerm.

C4.5 Construct Encoding hPOD with N-Terminal OsSP Signal Peptide and N-Terminal Glycomodule
p2300D-UbiPro-OsSP-NGM-hPod-35STerm (SEQ ID NO 16)

Codon optimized *Homo sapiens* podoplanin (GenBank acc no AY194238) (1. Organism: *Nicotiana tabacum*, 2. Organism: *Arabidopsis thaliana*) OsSP-NGM-hPod (N-teuninal GM and tags) was synthesized and delivered in pUC57 by GenScript (USA Inc.). OsSP-MUC1-3.5TR-CGM of pUC57-UbiPro-OsSP-MUC1-3.5TR-CGM-35STerm was cut out using SacI and replaced by SacI-fragment OsSP-NGM-hPod, yielding pUC57-UbiPro-OsSP-NGM-hPod-35STerm. UbiPro-OsSP-NGM-hPod-35STerm was excised by HindIII, isolated and inserted into the MSC-HindIII site of pC2300D, yielding pC2300D-UbiPro-OsSP-NGM-hPod-35STerm.

C4.6 Construct encoding MUC1-3.5TR N-terminally fused to Yfp with PpSP signal peptide pC2300u-35SPro-PpSP-MUC1-3.5TR-Yfp(H)$_6$-35STerm (SEQ ID NO 17) MUC1-3.5TR was synthesized by MWG (Germany), and codon optimized for expression in *Arabidopsis thaliana*, and the signal peptide for secretion was from *Physcomitrella patens* aspartic protease (ASP) (EMBL acc. No. AJ586914, Schaaf et al. 2005). MUC1-3.5TR was PCR-amplified using the primers 5'-GGCTTAAUatggggggcatcgagga-3' (PPpSP-MUC1-3.5TRFor) and 5'-ggtttaaUactgtatccggtcggaagtga-3' (PMUC1-3.5TRRev), and inserted into pC2300u vector containing Yfp (Nour-Eldin et al. 2006), yielding pC2300u-35SPro-PpSP-MUC1-3.5TR-Yfp(H)$_6$-35STerm.

C4.7 Construct Encoding MUC1-3.5TR C-Terminally Fused to Yfp with ChiSP Signal Peptide
p2300D-UbiPro-chiSP-YfpMUC1-3.5TR-35STerm (SEQ ID NO 18)

AtSp-YfpMUC1-3.5TR-TrT7(H)$_6$ was PCR-amplified using standard PCR conditions, pC2300u-35SPro-PpSP-MUC1-3.5TR-Yfp(H)$_6$-35STerm (C4.6) as template and the primers: 5'-gagctccatgggtaagac-taatcttttctctttctcatatttcacttctcctatcattatcctcggccgagcaa Gtgagcaagggcgaggagct-3' (PAtSpYfpFor; SEQ ID NO 46) and 5'-catatgatgtacagctcgtccatg-3' (PYfpRev; SEQ ID NO 47), where Tr, T7 & (H)$_6$ designate, Trombin cleavage site, T7 epitope, & (H)$_6$, respectively, underscore designate SacI, BamHI & NdeI, italics designates AtSp sequence and 5'Yfp sequence, isolated and inserted into p2300D using NdeI and EcoRI, yielding pC2300D-UbiPro-AtSp-YfpMUC1-3.5TR-TrT7(H)$_6$-35STerm.

C4.8 Construct Encoding Interferon of2B with C-Terminal Glycomodule and NtSP2 Signal peptide
p2300D-UbiPro-NtSP2-INF-α2B-CGM-35STerm (SEQ ID NO 19)

Codon optimized (1. Organism: *Nicotiana tabacum*, 2. Organism: *Arabidopsis thaliana*) *Homo sapiens* Interferon α2 B (INF-α2B-CGM, Genebank acc no. AY255838.1, C-terminal GM and tags) was synthesized and delivered in pUC57 by GenScript (USA Inc.). where NtSP2 designates signal sequence of *Nicotiana tabacum* proline-rich protein 3 (UniProt acc no T03236, Q40502), SP designates signal sequence of *Nicotiana tabacum* proline-rich protein 3 (UniProt acc no T03236, Q40502)), underscore designate EcoRI, SacI, NcoI, AscI, MluI, SalI, AfeI & BstEII, His tag (H)$_6$, Trombin cleavage recognition sequence (LVPRGS; SEQ ID NO 70), T7 epitope tag (MASMTGGQQMG; SEQ ID NO 71) and (SP)$_{10}$ Glyco module (GM). The SacI fragment in p2300D-UbiPro-OsSP-NGM-hPod-35STerm (C4.5) was replaced by the SacI-flanked INF-α2B-CGM fragment, yielding p2300D-UbiPro-NtSP2-INF-α2B-CGM-35STerm.

C4.9 Construct Encoding MUC1-2TR Embedded in YFP with OsSP Signal Peptide
pC2300-UbiPro-OsSP-GF-((H)$_8$MUC1-2TR-c-myc)FP-35STerm (SEQ ID NO 20)

(H)$_8$MUC1-2TR fragment was PCR-amplified using pC2300-UbiPro-OsSP-MUC1-3.5TR-CGM-35STerm (C4.2) as template and the primers: P-MUC1-2TR For (SEQ ID NO 50): 5'-CCATGGCTCTGTTACTAGTGCTCCA-GATA-3', P-MUC1-2TRRev SEQ ID NO 51): 5'-CCATGG-GATCCCGGAGCAGGTCTTGT-3', sub-cloned into pCR2.1TA, and excised using NcoI, yielding NcoI-(H)$_8$ Muc1-2TR-NcoI, which was inserted into pCold III-mfGFP vector (Kobayashi et al. 2008) between amino acid Asp173-Gly174 of GFP with a C-terminal c-myc tag, yielding the translational G-(H)$_8$Muc1-2TR-FP-c-myc fusion. GF-((H)$_8$MUC1-2TR-c-myc)FP was then PCR amplified using the primers: P-GFPFor SEQ ID NO 52): 5'-GAGCTCCATGGG-TAAGACTAATCTTTTTCTCTTTCT-CATCTTTTCACTTCTCCTATCAT TATCCTCGGC-CGAGCAAGTGAGCAAGGGCGAGGAGCTGT-3', and P-GFPRev (SEQ ID NO 53) 5'-GAGCTCCTACCCCTTG-TACAGCTCGTCCATGC-3', subcloned into pCR2.1TA, and inserted into pC2300-UbiPro-OsSP-MUC1-3.5TR-CGM-35STerm (C4.2) using SacI, yielding pC2300-UbiPro-OsSP-GF-((H)$_8$MUC1-2 TR-c-myc)FP)-35STerm.

C4.10 Construct Encoding MUC16-1.2TR with OsSP Signal Peptide and C-Terminal T7 and His tag
pC2300-UbiPro-OsSP-Muc16-1.2TR-T7-(H)$_6$-35STerm (SEQ ID NO 21)

Codon optimized (1. Organism: *N. benthamiana*, 2. Organism: *Arabidopsis thaliana*) OsSP-MUC16 1.2TR-T7H$_6$ (C-terminal T7 and H$_6$ tags) was synthesized using human Mucin 16 (AF414442.2) as template and inserted into pUC57 by MWG (Germany), yielding pUC57-OsSP-MUC16-1.2TR-T7(H)$_6$-35STerm. OsSP-MUC16-1.2TR-T7(H)$_6$ was excised by SacI, isolated and inserted into the SacI site of pC2300-UbiPro-OsSP-MUC1-3.5TR-CGM-35STerm (C4.2), yielding pC2300-UbiPro-OsSP-Muc16-1.2TR-T7-H$_6$-35STerm.

C5 Construct for Determining the Presence or Absence of UDP-GalNAc in Plants

For construction of pC1302D-35SPro-AaSP-MUC1-3.5TR-35STerm, 35SPro-T2-35STerm (C2.1) see pC1302D-35SPro-T2-35STerm (C2.2).

C6 Single Constructs Implementing Mucin-Type O-glycosylation

C6.1 Single Polycistronic Construct Encoding MUC1-3.5TR-YFP and Golgi Targeted Epimerase and GalNAc T2 Interspaced by Two 2a Sequences
pBI121-35Pro-PpSP-MUC1-3.5TR-Yfp-2A-Golwbpp-2A-T2-NosTerm (SEQ ID NO 17, SEQ ID NO 3, SEQ ID NO 5)

PpSP-MUC1-3.5TR-Yfp was PCR amplified using standard PCR conditions, pC2300u-35SPro-PpSP-MUC1-3.5TR-Yfp(H)$_6$-35STerm (C4.6) as template and the primers: PpSP-MUC1-3.5TR-YfpFor (SEQ ID NO 54): 5'tctaga ATGGGGGCATCGAGGAGTGT-3' and reverse primer PpSP-MUC1-3.5TR-YfpRev (SEQ ID NO 55): 5' Gttaacaaa-gatcctctcccttcaccactaccac-taGTGTGATGGTGATGGTGATGCTT-3, where underscore disignate XbaI, HpaI, italics designates 2A sequence, capital letters designate 5'-MUC1 and 3'-Yfp sequences, yielding the 'MUC1-Yfp-2A' where 2A is partial. Resulting 3'-Yf$_P$(H)$_6$-2A-5'-GalNAc-T2 (SEQ ID NO 72): 5'-catcac-catcaccatcacactagt ggtagtggtgaagggagaggatctttgttaacttgtggagacgtggaagagaaccctgga *cct* atgcggcggcgctcg-3', HHHHHHTS GSGEGRGSLLTCGDVEENPG *P* MRRRS (SEQ ID NO 73).

2A(partial)-Golwbpp-2A-(2A-5'end) was PCR amplified using standard PCR conditions, pC2300-35SPro-FT2Golwbpp-35STerm (C1.3) as template and the primers 5'-gttaacttgtggagacgtggaagagaaccctggacct ATGCGGCG-GCGCTCGCGGAT-3' (PGolwbppFFor; SEQ ID NO 56), 5'-gctagcttcaggagatcaaaattaagagtttgcccgctgccctcgag CTTGTCGTCGTCGTCCTTGT-3' (PGolwbppFRev; SEQ ID NO 57), where underscore designate HpaI & NheI, italics designates 2A sequence, capital letters designate Golwbpp. Resulting 3'-GolT2wbppF-2A-5'-GalNAc-T2 (SEQ ID NO 74): 5'-gacgacgacaagctcgag ggcagcgggcaaactct-taattttgatctcctgaagctagctggagacgttgagtcaaatccaggt *ccg* atgcggcggcgctcg, DDDKLE GSGQTLNFDLLKLAGD-VESNPG *P* MRRRSU (SEQ ID NO 75). 2A(partial)-T2 was PCR amplified using standard PCR conditions, pC1302D-35SPro-AaSP-MUC1-3.5TR-35STerm, 35SPro-T2-35STerm (C2.1) as template and the primers: 5'-gctagctg-gagacgttgagtcaaatccaggtccg ATGCGGCGGCGCTCGCG-GAT (P2AT2For; SEQ ID NO 58) 5'-gagctcCTACTGCTGCAGGTTGAGCGT-3' (P2AT2Rev; SEQ ID NO 59), where underscore designate NheI & SacI, italics designates 2A sequence, capital letters designate Gal-NAc-T2.

2A sequences were codon optimized for expression in *Nicotiana tabacum* and *Arabidopsis thaliana*.

Assembling the three fragments: first, the NheI-T2-SacI fragment was cloned into TOPO vector pCR2.1 already containing the HpaI-GolwbppF-NheI fragment using NheI and SacI. Then XbaI-MUC1-Yfp-2A-HpaI was inserted using XbaI and HpaI. The XbaI-SacI three genes—2×2A fragment was isolated and inserted into XbaI-SacI of pBI121, yielding pBI121-35Pro-PpSP-MUC1-3.5TR-Yfp-2A-Golwbpp-2A-T2-NosTerm.

C6.2 Single Construct Encoding MUC1-3.5TR-YFP and Polycistronic Cytosolic Epimerase and GalNAc T2 Interspaced by the 2A Sequence
pC1302D-35SPro-AaSP-MUC1-3.5TR-Yfp(H)$_6$-35STerm; 35SPro-T2-2A-FWbp (SEQ ID NO 17, SEQ ID NO 5, SEQ ID NO 1).

Removal of Hema Aglutinin (HA) tag: The 35SPro-T2-Fwbpp-35Sterm was PCR-amplified using 35SPro-pC1300-HAT2-Fwbpp-35Sterm (C3.1) as template and the primers 5'-cacgtggaattcgccatggttatgcggcggcgctcgcggatgct-3'
(PT2anchorFor; SEQ ID NO 32) and 5'-agcgctaggcctgagctc tcatttcaaaaacatgatgtac-3 (PwbppRev; SEQ ID NO 76) where underscoring designates SacI, StuI, AfeI, SacI, bold designates 5' T2 and 3' wbpp sequences and stop codon bold and italicized. The PCR fragment was digested with StuI and AfeI, isolated and StuI-AfeI fragment of pC1302D-35Pro-MUC1-3.5TR-35STerm; 35Pro-T2-35STerm was replaced by the StuI-AfeI C-terminal part of T2.

Substituting AaSP-MUC1-3.5TR with AaSP-MUC1-3.5TR-Yfp(H)$_6$: 35 SPro-AaSP-MUC1-3.5TR-35STerm of pC1302D-35SPro-AaSP-MUC1-3.5TR-35STerm; 35SSPro-T2-35STerm was replaced by 35Pro-AaSP-MUC1-3.5TR-Yfp(H)$_6$-35STerm of pC2300-AaSP-MUC1 Yfp(H)$_6$ using HindIII site, yielding p1302D-35SPro-AaSP-MUC1-3.5TR-Yfp(H)$_6$-35STerm; 35SProT2-2A-FWbp with both transcriptional units having the same orientation.
C7. Construct for Introduction of UDP-GalNAc-Transporter hUGT1
pC2300-UbiPro-hUGT1-c-myc-35STerm (SEQ ID NO 24)
Codon optimized (1. Organism: *N. benthamiana*, 2. Organism: *Arabidopsis thaliana*) C-terminal c-myc tagged hUGT1 (P78381-2) is synthesized and cloned into pUC57 by MWG (Germany). The SacI-insert of pC2300-UbiPro-OsSP-MUC1-3.5TR-CGM-35STerm (C4.2) is replaced with SacI delineated fragment of hUGT1 of hUGT1-pUC57, yielding pC2300-UbiPro-hUGT1-c-myc-35STerm.

f) EXAMPLE E1-E7

Example E1

Subcellular Specific Expression of *P. aeruginosa* C4 Epimerase (WbpP)

E1.1 Expression of Cytoplasmic WbpP
pC2300-35SPro-Fwbpp-35Sterm (C1.1)
N-terminal Flag tagged soluble epimerase (FWbpP) is expressed with the expected size (39.7 kDa) in *Arabidopsis thaliana* transgenic for the construct pC2300-35SPro-Fwbpp-35Sterm (C1.1).

FIG. 1. Western analysis of total proteinacious leaf derived extracts of wt and a transgenic *Arabidopsis thaliana* line expressing cytoplasmic N-terminally Flag-tagged WbpP (FWbpP) pC2300-35SPro-Fwbpp-35Sterm (C1.1). Primary mAb: anti Flag (DYKDDDD) M2 mAb (Sigma-Aldrich). Positive control: Flag-tagged Bovine Serum albumine Protein (BAP, Sigma-Aldrich).
E1.2 Expression of ER Targeted WbpP
pC2300-35SPro-AaSP-FwbppKDEL-35STerm (C1.2)
N-terminal Flag tagged soluble WbpP (FWbpP-KDEL) including aa N-terminal *Oryza sativa* alpha-amylase signal peptide (AaSP) and the C-terminal ER retention signal KDEL (FWbpP-KDEL) is expressed with the expected size (40.1 kDa) in *Arabidopsis thaliana* transgenic for the construct pC2300-35SPro-AaSP-FwbppKDEL-35Sterm (C1.2.).

FIG. 2. Western analysis using anti Flag primary mAb on total protein leaf-extracts of wt and a transgenic *Arabidopsis thaliana* line ER targeted FWbpP-KDEL pC2300-35SPro-Fwbpp-35Sterm (C1.2). Primary mAb: anti Flag (DYKD-DDD) M2 mAb (Sigma-Aldrich). Positive control: Flag-tagged Bovine Serum albumine Protein (BAP, Sigma-Aldrich).
E1.3 Expression of Golgi Targeted WbpP
pC2300-35SPro-FT2Golwbpp-35STerm (C1.3)
N-terminal Flag tagged Golgi targeted WbpP (FT2GolWbpP: Flag-tagged GalNAc-T2 cytoplasmic tail+TMD and stem region fused to WbpP) is expressed with the expected size (56.1 kDa) in *Arabidopsis thaliana* transgenic for the construct pC2300-35SPro-FT2Golwbpp-35STerm (C1.3).

FIG. 3. Western analysis using anti Flag primary mAb on total proteinacious leaf-extracts of wt and a transgenic *Arabidopsis thaliana* line expressing Flag-tagged Golgi targeted WbpP (FT2GolWbpP: Flag-tagged GalNAc-T2 cytoplasmic tail, TMD and stem region fused to WbpP, pC2300-35SPro-FT2Golwbpp-35STerm (C1.3). Primary mAb: anti Flag (DYKDDDD) M2 mAb (Sigma-Aldrich). Positive control: Flag-tagged Bovine Serum albumine Protein (BAP, Sigma-Aldrich).

Example E2

Expression of Golgi Targeted GalNAc-Transferases

E2.1. Expression of Golgi Targeted GalNAc-T2
pC1302D-35SPro-T2-35STerm (C2.2)
GalNAc-T2 is stably expressed with the expected size (64.7 kDa) in *Arabidopsis thaliana* transgenic for the construct pC1302D-35SPro-T2-35STerm (C2.2) and GalNAc-T2 is associated with membranes (microsomal fraction) as demonstrated by Western blot analysis of total proteinacious leaf-extracts which was sub-fractionated in to a microsomal (total membrane) and soluble fraction.

FIG. 4. Western analysis of total proteinacious leaf-extracts of wt and a transgenic *Arabidopsis thaliana* (A) and total proteinacious leaf-extracts of transient *N. bethamiana*, which were sub-fractionated into a microsomal (total membrane) and soluble fraction (B) both expressing GalNAc-T2 (pC1302D-35SPro-T2-35STerm (C2.2)). Primary mAb 6B7 (anti GalNAc-T2), T.E. (Total proteinacious extracts), Sup. (Soluble fraction), Mic. (Microsomal fraction). Positive control: soluble part of GalNAc-T2 expressed in and purified from Baculo virus Sf9 cells (BvT2).

E2.2 Expression of Golgi Targeted GalNAc-T4

Example E3

Expression of Enzymes Conferring Mucin-Type O-glycosylation Capacity

E3.1 Expression of Cytoplasmic FWbpP and HA Tagged Golgi GalNAc-T2 from One Polycistronic Transcript pC1302-35SPro-HAT2-2A-FWbpP-35STerm (C3.1)

Mucin-type O-glycosylation capacity has been implemented by the polycistronic construct pC1302-35SPro-HAT2-2A-Fwbpp-35STerm (C3.1) where (HA)GalNAc-T2 (Golgi targeted) and *P. aeruginosa* C4 epimerase (WbpP, cytosolic), interspaced by the self splicing 2A sequence (Cf Materials and Methods), are expressed as a single polyprotein which is co-translationally spliced into the respective two functional proteins, as e.g. evidenced by stable and transient expression of pC1302-35SPro-HAT2-2A-Fwbpp-35STerm (C3.1) in *A. thaliana*, and *N. benthamiana*, respectively. (HA) GalNAc-T2 has a Hemma Agglutinin (HA) tag fused to the N-terminus of GalNAcT2.

FIG. 5. Western analysis of GalNAc-T2 and *P. aeruginosa* C4 epimerase (WbpP) expressed transiently in *N. benthamiana* from polycistronic construct pC1302-35SPro-HAT2-2A-FWbpP-35STerm (C3.1). Total protein extracts from *N. benthamiana* leaves, inoculated with (+) or without (−) pC1302-35SPro-HAT2-2A-FWbpP-35STerm (C3.1) construct, containing polycistronic sequence encoding Golgi targeted GalNAc-T2 transferase and cytosolic WbpP, were subjected to immunoblotting using the primary mAbs 6B7 (anti GalNAc T2, A) anti-Flag M2 mAb (FWbpP, B), respectively. Calculated approximate MWs of GalNAc-T2 and FWbpP are 66 and 39 kDa, respectively. Strong signals are detected at positions consistent with these masses in protein extracts from the inoculated plants, and absent in the control sample. Protein molecular mass marker is indicated (M), and presence or absence of pC1302-35SPro-HAT2-2A-FWbpP-35STerm (C3.1) in the inoculated *N. benthamiana* is indicated with (−) or (+). Approximately 30 μg total protein was loaded in each lane.

E3.2 Expression of Golgi GalNAc-T2 and Cytoplasmic WbpPF from One Polycistronic Transcript pBI121-35SPro-wbppF-2A-T2-35STerm (C3.2)

Mucin-type O-glycosylation capacity has been implemented by the polycistronic construct pBI121-35SPro-wbppF-2A-T2-NosTerm (C3.2) where *P. aeruginosa* C4 epimerase (WbpP, cytosolic) and GalNAc-T2 (Golgi targeted), interspaced by the self splicing 2A sequence (Cf Materials and Methods) are expressed as a single polyprotein which is co-translationally spliced into the respective two functional proteins, as e.g. evidenced by transient expression of pBI121-35SPro-wbppF-2A-T2-NosTerm (C3.2) in *N. benthamiana*, and stable expression both in *N. benthamiana* and BY-2 cells. pBI121-35SPro-wbppF-2A-T2-NosTerm (C3.2) and pC1302-35SPro-HAT2-2A-FWbpP-35STerm (C3.1) have reverse translational order of the functional Golgi targeted and cytosolic enzymes.

FIG. 6. Western analysis of *P. aeruginosa* C4 epimerase (WbpP, cytosolic) and GalNAc-T2 (Golgi targeted) expressed transiently in *N. benthamiana* from polycistronic construct pBI121-35SPro-wbppF-2A-T2-35STerm (C3.2). Total protein extracts from *N. benthamiana* leaves, inoculated with (+) or without (−) the pBI121-35SPro-wbppF-2A-T2-NosTerm (C3.2) construct, containing polycistronic sequence encoding cytosolic WbpP and Golgi targeted GalNAc-T2, were subjected to Western analysis using the primary mAbs anti-Flag M2 (FWbpP, B) and 6B7 (GalNAc-T2, A), respectively. Calculated approximate MWs of GalNAc-T2 and FWbpP are 66 and 39 kDa, respectively. Strong signals are detected at positions consistent with these masses in protein extracts from the inoculated plants, and absent in the control sample. Protein molecular mass marker is indicated (M), and presence or absence of pBI121-35SPro-wbppF-2A-T2-NosTerm (C3.2) in the inoculated *N. benthamiana* is indicated with (−) or (+). Positive control: soluble part of GalNAc-T2 expressed in and purified from Baculo virus Sf9 cells (BvT2) and Flag-tagged Bovine Serum albumine Protein (BAP, Sigma-Aldrich). Approximately 30 μg total protein was loaded in each lane.

E3.3 Expression of Cytoplasmic FWbpP and Golgi GalNAc-T2 from One Polycistronic Transcript p1302D-35SPro-T2-2A-Fwbpp-35STerm (C3.3)

Mucin-type O-glycosylation capacity has been implemented by the polycistronic construct p1302D-35SPro-T2-2A-Fwbpp-35STerm (C3.3) where Golgi targeted GalNAc-T2 and cytosolic *P. aeruginosa* C4 epimerase (WbpP) interspaced by the self splicing 2A sequence (Cf Materials and Methods), are expressed as a single polyprotein which is co-translationally spliced into the respective two functional proteins, as e.g. evidenced by transient expression in *N. benthamiana*, and stable expression in BY-2 cells and *A. thaliana*. The difference between pC1302-35SPro-HAT2-2A-FWbpP-35STerm (C3.1) and p1302D-35SPro-T2-2A-Fwbpp-35STerm (C3.3) is the presence of a Hemma Agglutinin (HA) tag in the N-terminus of GaNAc T2 ((HA)GaNAc T2) in pC1302-35SPro-HAT2-2A-FWbpP-35STerm (C3.1).

FIG. 7. Western analysis of GalNAc-T2 and *P. aeruginosa* C4 epimerase (WbpP) expressed transiently in *N. benthamiana* from polycistronic construct p1302D-35SPro-T2-2A-Fwbpp-35STerm (C3.3). Total protein extracts from *N. benthamiana* leaves, inoculated with (+) or without (−) the p1302D-35SPro-T2-2A-Fwbpp-35STerm (C3.3) construct, containing polycistronic sequences encoding Golgi targeted GalNAc-T2 transferase and cytosolic WbpP, were subjected to Western analysis using the primary mAbs 6B7 (anti GalNAc T2, A) and anti-Flag M2 (FWbpP, B), respectively. Calculated approximate MWs of GalNAc-T2 and FWbpP are 66 and 39 kDa, respectively. Strong signals are detected at positions consistent with these masses in protein extracts from the inoculated plants, and absent in the control sample. Protein molecular mass marker is indicated (M), and presence or absence of p1302D-35SPro-T2-2A-Fwbpp-35STerm (C3.3) in the inoculated *N. benthamiana* is indicated with (−) or (+). Positive control: soluble part of GalNAc-T2 expressed in and purified from Baculo virus Sf9 cells (BvT2) and Flag-tagged Bovine Serum albumin Protein (BAP, Sigma-Aldrich). Approximately 30 µg total protein was loaded in each lane.

Example E4

Expression and Structure of Mucin-type O-Glycosylation Target Peptides in wt and O-Glycosylation Capacity Backgrounds It should be noted that MUC1-3.5TR peptide tends to migrate as a dimer (i.e. ca 2× the predicted MW) on the SDS-PAGE gel system used here. This is also the case for the identical MUC1-3.5TR (positive control: EcMUC1-3.5TR) expressed in, and purified form, E. coli cells.

E4.1.1 Expression of MUC1-3.5TR
pC1302D-35SPro-AaSP-MUC1-3.5TR-35STerm (C4.1)

The 3.5 Tandem Repeat of the mucin MUC1 (MUC1-3.5TR) has been expressed with the somewhat predicted MW (10.2 kDa) (Cf. above) in stable transgenic Arabidopsis thaliana and Lemna minor and transiently in N. benthamiana.

FIG. 8. Western analysis of total proteinacious leaf-extracts of wt and A. thaliana (A), Lemna minor (B), N. benthamiana (C) expressing MUC1-3.5TR from pC1302D-35SPro-AaSP-MUC1-3.5TR-35STerm (C4.1) using primary mAb 5E10 (MUC1-3.5TR specific). Positive control: MUC1-3.5TR expressed and purified from E. coli (Ec-MUC1). Approximately 30 µg total protein was loaded in each lane.

E4.1.2 Structure of E. coli Derived MUC1-3.5TR

The 3.5 Tandem Repeat of the mucin MUC1 (MUC1-3.5TR) was expressed in E. coli with a mass (ESI-MS) identical to the predicted mass, i.e. without secondary post translations modifications (PTMs) thus allowing for E. coli derived MUC1-3.5TR (EcMUC1-3.5TR) to be used as experimental 'zero' reference.

FIG. 9. MS analysis of Asp-N digest following C18 zip tip column clean up of MUC1-3.5TR purified from E. coli. m/z with red star marker (Z=+3 charge peaks: m=629.65, m=639.99, and m=702.01) are the peptide-fragments identified from the MUC1-3.5TR amino acid sequence.

E4.1.3 Structure of A. thaliana Derived MUC1-3.5TR
pC1302D-35SPro-AaSP-MUC1-3.5TR-35STerm (C4.1)
pC1302D-35SPro-AaSP-MUC1-3.5TR-35STerm, 35SPro-T2-35STerm (C2.1)

MUC1-3.5TR of E. coli and stable transgenic A. thaliana line (5.10) is expressed as with identical masses (MALDI-TOF MS) and MUC1-3.5TR is thus expressed as native unmodified peptide, i.e. without secondary post translations modifications (PTMs), in the two A. thaliana transgenic lines.

The identical masses of E. coli and A. thaliana expressed MUC1-3.5TR strongly indicate that the plant derived MUC1-3.5TR is not modified by e.g. the endogenous plant prolyl-hydroxylation/O-glycosylation machinery in A. thaliana.

FIG. 10. MALDI-TOF MS analysis of A) a transgenic A. thaliana line co-expressing MUC1-3.5TR and GalNAc-T2 (pC1302D-35SPro-AaSP-MUC1-3.5TR-35STerm, 35SPro-T2-35STerm, C2.1), and B) a transgenic A. thalinana line only expressing MUC1-3.5TR from pC1302D-35SPro-AaSP-MUC1-3.5TR-35STerm (C4.1). MUC1-3.5TR was purified, Asp-N digested, following by C18 zip tip column clean up (Cf Materials and Methods). The MUC1-3.5TR Asp-N digested peptides m/z 1886.96=DTRPAPG STAP-PAHGVT SAP, 1917.96=DTRPAPG STAPQAHGVT SAP, 2103.03=DTRPAPGSTAPPAHGVTSAPDT are identical for both the co- and the single expression(s). The residual minor peaks m/z=1955,91, 2153,12, 2301,16 and 2332,17 do not correspond to plant derived proline hydroxylations or glycosylations, and are considered minor non-relevant contaminants.

E4.2 Mucin-Type O-Glycosylation of MUC1-3.5TR with Fused C-Terminal Glycomodule
pC2300-UbiPro-OsSP-MUC1-3.5TR-CGM-35STerm (C4.2)

MUC1-3.5TR has been expressed as a single protein with a C-terminal glycomodule (CGM, $(SP)_{10}$), for direction of AGP type of plant derived glycosylation to the glycomodule ($(SP)_{10}$) with an somewhat apparent MW centered around 20-25 kDa, when transiently expressed in N. benthamiana. The presence of the C-terminal GM ($(SP)_{10}$) resulted in an ca. 5 fold increase in the expression level as compared to constructs MUC1-3.5TR devoid of the GM.

FIG. 11. Western analysis of total proteinacious leaf-extracts of wt (p19) and wt of N. benthamiana transiently expressing MUC1-3.5 TR-CGM from pC2300-UbiPro-OsSP-MUC1-3.5TR-CGM-35STerm (C4.2), i.e. MUC1-3.5TR with a C-terminal $(SP)_{10}$ glycomodule (MUC1-CGM) using primary mAb 5E10 (MUC1-3.5TR specific). Positive control (EcMUC1-3.5TR). Approximately 30 µg total protein was loaded in each lane.

E4.6 Mucin-Type O-Glycosylation of MUC1-3.5TR-Yfp Target Peptide
pC1302-35SPro-HAT2-2A-FWbpP-35STerm (C3.1)
pC2300u-35SPro-PpSP-MUC1-3.5TR-Yfp$(H)_6$-35STerm (C4.6)
pBI121-35SPro-T4-NosTerm (C2.3)

E4.6.1 Mucin-Type O-Glycosylation of MUC1-3.5TR-YFP Target Peptide

Mucin-type O-glycosylation was accomplished by co-expression of construct for expression of the target MUC1-3.5TR from pC2300u-35SPro-PpSP-MUC1-3.5TR-Yfp $(H)_6$-35STerm (C4.6) together with a construct expressing the O-glycosylation machinery (pC1302-35SPro-HAT2-2A-FWbpP-35STerm (C3.1)) as evidenced Western blot analysis using glycosylation sensitive mAb 5E5 (MUC1-3.5TR-GalNAc specific (Tn)) and Vicia villosa lectin (VVA) blot and mAb 5E10 (MUC1-3.5TR specific). Introduction of heterologous expressed ER-Golgi localized UDP-GalNAc transporter is thus not strictly needed.

FIG. 12. Mucin-type O-glycosylation of MUC1-3.5TR-Yfp from pC2300u-35SPro-PpSP-MUC1-3.5TR-Yfp$(H)_6$-35STerm (C4.6) expressed in N. benthamiana leaves inoculated with (+) or without (−) polycistronic construct pC1302-35SPro-HAT2-2A-FWbpP-35STerm (C3.1), expressing (HA)GalNAc-T2 transferase and P. aeruginosa C4 epimerase (FWbpP) as evidenced by A) MUC1-3.5TR specific (mAb 5E10) and B) MUC1-3.5TR-GalNAc (Tn) specific (mAb 5E5) Western blot and C) Vicia villosa (VVA) lectin blot analysis. M, protein molecular mass marker; p19, protein extracts from N. benthamiana inoculated only with p19 anti-silencing construct. Signal was detected at approximately 40 kDa, which is close to the predicted molecular mass of MUC1-3.5TR-Yfp. The appearance of a double band may indicate partial processing of the 20 aa signal peptide located on MUC1-3.5TR-YFP. The absence of a signal in this sample on both the 5E5 mAb probed immunoblot and the VVA lectin-blot indicated that the MUC1-3.5TR component of MUC1-3.5TR-YFP was not modified by GalNAc sugars. When the MUC1-3.5TR-Yfp was co-expressed with pC1302-35SPro-HAT2-2A-FWbpP-35STerm (C3.1), a signal of ca. 42 kDa was also detected by 5E5 (MUC1-3.5TR-GalNAc specific) mAb and VVA lectin. This strongly indicated that the MUC1 moiety of the MUC1-3.5TR-YFP was modified with GalNAc sugars in these samples. In each case, the signal from plants co-inoculated with pC1302-35SPro-HAT2-2A-FWbpP-35STerm (C3.1) had an apparent molecular mass of about 1-2 kDa greater than that detected in samples expressing only MUC1-3.5TR-YFP. This is consistent with a mass increase resulting from the modification of MUC1 with GalNAc sugar residues. Approximately 30 μg total protein was loaded in each lane.

E4.6.2 Transient Expression of MUC1-3.5TR-Yfp in the Moss *Physcomitrella patens*
pC2300u-35SPro-PpSP-MUC1-3.5TR-Yfp(H)$_6$-35STerm (C4.6)

Transient expression of MUC1-3.5TR-YFP in the moss *Physcomitrella patens* was achieved as evidenced from fluorescence microscopy, i.e. florescence derived from YFP (carrier) of target MUC1-3.5TR-YFP in protoplasts of *P. patens* transiently transformed with pC2300u-35SPro-PpSP-MUC1-3.5TR-Yfp(H)$_6$-35STerm (C4.6).

FIG. 13. Red fluorescence represents chlorophyll autofluorescence (A), Green fluorescence derived for a single protoplast cell expressing MUC1-3.5TR-Yfp, B) (Except for the wavelengths, A and B is the same picture). Formation of protoplasts was essentially done as described in 'Preparation of BY-2 protoplasts' in the 'Material and Methods' section.

E4.6.3 Structure of MUC1-3.5TR-Yfp Expressed in WT and O-Glycosylation Capacity Background
pC1302-35SPro-HAT2-2A-FWbpP-35STerm (C3.1)
pC2300u-35SPro-PpSP-MUC1-3.5TR-Yfp(H)$_6$-35STerm (C4.6)
pBI121-35SPro-T4-NosTerm (C2.3)

Structural data (ESI and MALDI-TOF MS) demonstrating O-glycosylation of MUC1-3.5TR, i.e. mucin-type O-glycosylation was accomplished by co-expression of target MUC1-3.5TR-Yfp from pC2300u-35SPro-PpSP-MUC1-3.5TR-Yfp(H)$_6$-35STerm (C4.6) and the O-glycosylation machinery (pC1302-35SPro-HAT2-2A-FWbpP-35STerm (C3.1)), thus cooperating the data presented in e.g. E4.6.1. GalNAc-T2 mediated glycosylation yielded 1-, 2- and 3 GalNAc sugars attached per MUC1-1TR (full GalNAc-T2 mediated occupancy), which seemingly could be increased to 4 GalNAcs per MUC1-1TR when GalNAc-T4 (pBI121-35SPro-T4-NosTerm (C2.3)) was ectopically expressed.

FIG. 14. Structural determination of mucin-type O-glycosylation of MUC1 derived peptides as part of a MUC1-3.5TR-Yfp from pC2300u-35SPro-PpSP-MUC1-3.5TR-Yfp(H)$_6$-35STerm (C4.6) transiently expressed together with GalNAc-T2 transferase and WbpP (pC1302-35SPro-HAT2-2A-FWbpP-35STerm (C3.1), upper panel), and ectopically expressed with GalNAc-T4 transferase (pC1302-35SPro-HAT2-2A-FWbpP-35STerm (C3.1)+pBI121-35SPro-T4-NosTerm (C2.3), lower panel), in leaves of *N. benthamiana*. MS data was obtained by ESI-MS and MALDI-TOF MS for the combinations: pC1302-35SPro-HAT2-2A-FWbpP-35STerm (C3.1)+pC2300u-35SPro-PpSP-MUC1-3.5TR-Yfp(H)$_6$-35STerm (C4.6) and pC1302-35SPro-HAT2-2A-FWbpP-35STerm (C3.1)+pBI121-35SPro-T4-NosTerm (C2.3)+pC2300u-35SPro-PpSP-MUC1-3.5TR-Yfp(H)$_6$-35STerm (C4.6), respectively.

E4.6.4 Single and Combined Constructs Encoding Golgi Targeted Epimerase and GalNAc-T2 Conferring Mucin-Type O-Glycosylation
pBI121-35Pro-PpSP-MUC1-3.5TR-Yfp(H)$_6$-2A-FGolwbpp-2A-T2-NosTerm (C6.1)
pBI121-35SPro-GolwbppF-2A-T2-NosTerm (C3.5)
pC2300u-35SPro-PpSP-MUC1-3.5TR-Yfp(H)$_6$-35STerm (C4.6)

Mucin-type O-glysosylation was accomplished using one single construct pBI121-35Pro-PpSP-MUC1-3.5TR-Yfp-2A-Golwbpp-2A-T2-NosTerm (C6.1), which mediated expression of the target MUC1-3.5TR-YFP and the O-glycosylation machinery (Golgi targeted epimerase (FGolWbpP) and GalNAc-T2) as one single polyprotein, with two times 2A auto splicing sequence interspacing the three proteins, driven by a single promoter transiently in leaves of *N. benthamiana* and in stably transformed tobacco BY-2 cells as evidenced by glycosylation insensitive (mAb 5E10) and glycosylation sensitive (mAb 5E5) MUC1-3.5TR specific Western blot analysis of the target MUC1-3.5TR.

Mucin-type O-glysosylation was additionally accomplished using the construct pBI121-35SPro-T2GolWbpPF-2A-T2-NosTerm (C3.5), identical to pBI121-35Pro-PpSP-MUC1-3.5TR-Yfp-2A-Golwbpp-2A-T2-NosTerm (C6.1) but with the target MUC1-3.5TR-Yfp-cassette excised, in combination with pC2300u-35SPro-PpSP-MUC1-3.5TR-Yfp(H)$_6$-35STerm (C4.6) as evidenced by glycosylation insensitive (mAb 5E10) and glycosylation sensitive (mAb 5E5) MUC1-3.5TR specific Western blot analysis of target MUC1-3.5TR.

FIG. 15. A. Mucin-type O-glysosylation in leaves of *N. benthamiana* obtained from a single polyprotein synthesizing construct pBI121-35Pro-PpSP-MUC1-3.5TR-Yfp(H)$_6$-2A-FGolwbpp-2A-T2-NosTerm (C6.1) consisting of the target protein MUC1-3.5TR-YFP follow by Golgi targeted epimerase FGolWbpP and GalNAc-T2, with the three proteins interspaced by two 2A auto-splicing sequences, as evidenced from glycosylation insensitive (mAb 5E10, upper panel) and glycosylation sensitive (mAb 5E5, lower panel) MUC1-3.5TR specific Western blot analysis of the target MUC1-3.5TR in crude proteinacious leaf extracts. The pBI121-35Pro-PpSP-MUC1-3.5TR-Yfp-2A-Golwbpp-2A-T2-NosTerm (C6.1) derived construct pBI121-35Pro-GolwbppF-2A-T2-NosTerm (C3.5), where the target MUC1-3.5TR-Yfp-cassette has been excised, showed the same functionality when transiently co-expressed with pC2300u-35SPro-PpSP-MUC1-3.5TR-Yfp(H)$_6$-35STerm (C4.6) for expression of MUC1-3.5TR-YFP) in leaves of *N. benthamiana*. B, ESI-MS data demonstrating addition 1- and 2 GalNAc sugars onto the target MUC1-3.5TR-YFP protein, when transiently co-expressed in leaves of *N. benthamiana* with O-glycosylation machinery pBI121-35Pro-GolwbppF-2A-T2-NosTerm (C3.5), encoding Golgi targeted epimerase and GalNAc-T2 transferase. p19, protein extracts from *N. benthamiana* inoculated only with P19 anti-silencing construct, Positive control: Glycosylated MUC1-3.5TR-Yfp transiently expressed in- and purified from *N. benthamiana* plants (Tobacco MUC1-YFP Tn Control). Approximately 30 μg total protein was loaded in each lane.

E4.6.5 Stable *Arabidopsis* Line Expressing a Single Construct Conferring Mucin-Type O-Glycosylation.
pC1302D-35SPro-AaSPMUC1-3.5TR-Yfp(H)$_6$-35STerm; 35SPro-T2-2A-Fwbpp (C6.2)

Mucin-type O-glysosylation was accomplished using one single construct expressing the target MUC1-3.5TR-YFP and the O-glycosylation machinery (Golgi targeted GalNAc-T2 and cytosolic C4-epimerase (FWbpP) interspaced by the 2A auto splicing sequence) from two separate promoters (pC1302D-35SPro-AaSP-MUC1-3.5TR-Yfp(H)$_6$-35STerm; 35SPro-T2-2A-FWbp (C6.2)) as demonstrated by glycosylation insensitive (mAb 5E10) and glycosylation sensitive (mAb 5E5) MUC1-3.5TR specific Western blot and structural (MALDI-TOF MS) analysis of the target MUC1-3.5TR.

FIG. 16. Mucin-type O-glysosylation in stably transformed *Arabidopsis thaliana* line 2A9.3 obtained from transformation of a single construct pC1302D-35SPro-AaSP- MUC1-3.5TR-Yfp(H)₆-35STerm; 35SPro-T2-2A-Fwbpp (C6.2) containing the target protein MUC1-3.5TR-YFP and the O-glycosylation machinery, Golgi targeted GalNAc-T2 followed by the cytosolic epimerase (FWbpP) interspaced by the 2A auto splicing sequence, driven by two separate 35S promotors. O-glycosylation of target MUC1-3.5TR-YFP was accomplished as evidenced by glycosylation insensitive (mAb 5E10) and glycosylation sensitive (mAb 5E5) MUC1-3.5TR specific Western blot and *Vicia villosa* (VVA) lectin blot analysis of the target MUC1-3.5TR in crude proteinacious extracts and MALDI-TOF analysis of purified and Asp-N digested MUC1-3.5TR-YFP (Cf Material and Methods section). MUC1-1TR with 1, -2 and 3-GalNAc sugars were identified, when expressed stably in *A. thaliana*. A) VVA lectin mediated purification (Cf Material and Methods section) of MUC1-3.5TR-Yfp as evidenced by: coomassie stained SDS-PAGE (upper panel) and Western analysis using mAb 5E10 (middle panel) and mAb 5E5 (lower panel). HIC (Hydrophobic Interaction Chromatography, eluate of Phenyl sepharose CL-4B column), FT (Flow through), W1-2 (Wash), E1-4 (Elution from VVA—lectin agarose). 10 µl was loaded in each lane. B. MALDI-TOF of E2. E2 was and subjected to Asp-N digestion, C18 clean up and then finally to MALDI-TOF analysis as described in the Material and Methods section. MUC1-1TR substituted by 1-(2091.1), 2-(2293.88) and 3 GalNAc (2496.76) sugars are indicated with red circles. Approximately 30 µg total protein was loaded in each lane.

E4.7 Mucin-Type O-Glycosylation of Yfp-MUC1-3.5TR Target Peptides
p2300D-UbiPro-chiSP-YfpMUC1-3.5TR-TrT7(H)₆-35STerm (C4.7)

Exchange of the translational order or the carrier (YFP) and target peptide (MUC1-3.5TR), i.e. MUC1-3.5TR-Yfp (e.g. pC23000-35SPro-PpSP-MUC1-3.5TR-Yfp(H)₆-35STerm (C4.6) vs Yfp-MUC1-3.5TR, appeared not to affect the expression level, glycosylation state or stability of the two fusion proteins.

FIG. 17. Western analysis using glycosylation sensitive MUC1-3.5TR specific mAb 5E5 on total proteinacious extracts of wt and BY-2 cells expressing Yfp-MUC1-3.5TR from p2300D-UbiPro-chiSP-YfpMUC1-3.5TR-35STerm (C4.7). Positive control: MUC1-3.5TR-Yfp transiently expressed in- and purified from *N. benthamiana* plants. Approximately 30 µg total protein was loaded in each lane.

E4.8 Mucin-Type O-Glycosylation of Embedded G-MUC1-2TR-fp Target Peptide
pC2300-UbiPro-OsSP-Gf-((H)₈Muc1-2TR-c-myc)fP-35STerm (C4.9)
pC1302D-35SPro-FWbpP-35STerm; 35SPro-T2-35STerm (C3.4)

Mucin target was embedded within a carrier protein (here GFP) while retaining its substrate specificity for the O-glycosylation machinery. Mucin-type O-glycosylation of MUC1-2TR embedded in GFP (G-(H)₈MUC1-1TR-c-myc-FP from pC2300-UbiPro-OsSP-GF-(H)₈MUC1-2TR-c-myc)FP-35STerm (C4.9) expressed in O-glycosylation capacity background (pC1302D-35SPro-FWbpP-35STerm; 35SPro-T2-35STerm (C3.4), in the stable double transgenic tobacco suspension BY-2 cell line 62.70.5 was accomplished as evidenced by glycosylation state independent (mAb 5E10) and dependent (mAb 5E5) MUC1-3.5TR specific Western analysis of crude proteinacious extracts and MALDI-TOF analysis of purified and Asp-N digested G-(H)₈MUC1-1TR-c-myc-FP (Cf Material and Methods section).

FIG. 18. Mucin-type O-glycosylation of GF-(H)₈MUC1-1TR-c-myc-FP from pC2300-UbiPro-OsSP-GF-((H)₈MUC1-2TR-c-myc)FP-35STerm (C4.9) in tobacco suspension BY-2 cell line 62.70.5 designates wt BY-2 transformed firstly with the target pC2300-UbiPro-OsSP-GF-((H)₈MUC1-2TR-c-myc)FP-35STerm (C4.9), secondly with O-glycosylation machinery pC1302D-35SPro-FWbpP-35STerm; 35SPro-T2-35STerm (C3.4). His-tag purification of His-tagged embedded MUC1-2TR in GFP (GF-(H)₈MUC1-2TR-c-myc-FP) is described in the Material and Methods section. TE (Total Extract), FT (Flow through), E1-3 (Elution from Ni-NTA-column). 10 µl was loaded in each lane. A) Comassie stained SDS-PAGE (upper panel) and Western analysis using mAb 5E10 (middle panel) and mAb 5E5 (lower panel). B. MALDI-TOF analysis of E2. E2 was and subjected to Asp-N digestion, C18 clean up and then finally to MALDI-TOF analysis as described in the Material and Methods section. Naked MUC1-1TR is 1886.2. MUC1-1TR substituted by 1-(2090.1) and 2 GalNAc (2293.54) sugars are indicated with red circles.

E4.9 Expression and Mucin-Type O-Glycosylation of MUC16 Target Peptide
pC2300-UbiPro-OsSP-Muc16-1.2TR-T7-(H)₆-35STerm (C4.10)
pC1302-35SPro-HAT2-2A-FWbpP-35STerm (C3.1)

1.2Tandem repeat (1.2TR) of target Mucin 16 was stably expressed in BY-2 suspension cells and transiently in leaves of *N. benthamiana*, where co-expression with the O-glycosylation machinery (pC1302-35SPro-HAT2-2A-FWbpP-35STerm (C3.1)) conferred O-glycosylation as evidenced by O-glycosylation specific Western/blot and lectin blot analysis.

FIG. 19. A. Western blots (mAbs M11 (MUC16 specific) and T7) and VVA lectin blot of transient co-expression of MUC16 1.2TR from pC2300-UbiPro-OsSP-Muc16-1.2TR-T7-(H)₆-35STerm (C4.10)) with O-glycosylation machinery (pC1302-35SPro-HAT2-2A-FWbpP-35STerm (C3.1)) in leaves of *N. benthamiana*. B. Stable tobacco BY-2 cell lines (63.16) expressing MUC16-1.2TR from pC2300-UbiPro-OsSP-Muc16-1.2TR-T7-(H)₆-35STerm (C4.10)

E4.10 Expression and O-Glycosylation of Human Interferon α2B
p2300D-UbiPro-NtSP2-INF-α2B-CGM-35STerm (C4.8)

Mucin-type O-glycosylation of human INF-α2B has been accomplished by expression of target peptide NtSP2INF-α2B-CGM (INF-α2B with an N-terminal fused signal peptide for direction into the secretory pathway and a C-terminal situated glycol module (CGM) for direction of AGP type of plant derived glycosylation to the glycomodule ((SP)₁₀) co-expressed with the construct conferring O-glycosylation capacity (pC1302-35SPro-HAT2-2A-FWbpP-35STerm (C3.1)) transiently in leaves of *N. benthamiana* as evidenced by VVA Lectin blot analysis. An apparent shift in MW from 28 kDa to 30 kDa was observed when expressed in the O-glycosylation capacity background. Also, it should be noted that INF-α2B contain only a single mucin-type O-glycosylation site (Thr, T) in GVGVTETPLM sequence from INF-α2B protein.

FIG. 20. Western analysis using prim T7 mAb on total proteinacious leaf extracts of *N. benthamiana* wt (p19) and wt transiently expressing human interferon INF-α2B-CGM (p2300D-UbiPro-NtSP2INF-α2B-CGM-35STerm (C4.8)) with and without the O-glycosylation machinery (pC1302-35SPro-HAT2-2A-FWbpP-35STerm (C3.1)). Positive control: T7 tagged positive protein (Novagen USA). Approximately 30 μg total protein was loaded in each lane.

E4.11 Expression of Human Podoplanin (hPOD)
p2300D-UbiPro-OsSP-NGM-hPod-35STerm (C4.5)

Human podoplanin (hPOD) was transiently expressed in leaves of *N. benthamiana* with an apparent MW (24.9 kDa) corresponding to the predicted MW of hPOD.

FIG. 21. Western analysis using primary T7 mAb on *N. benthamiana* total proteinacious leaf extracts of wt (p19) and wt transiently expressing human podoplanin NGM-hPod (p2300D-UbiPro-OsSP-NGM-hPod-35STerm (C4.5)) with an N-terminal situated glycol module (NGM) for direction of AGP type of plant derived glycosylation to the glycomodule ($(SP)_{10}$). Positive control: T7 tagged positive protein (Novagen USA). Approximately 30 μg total protein was loaded in each lane.

Example E5

Co-Expression of MUC1-3.5TR & GalNAc-T2

E5.1 Expression of MUC1-3.5TR & GalNAc-T2 and Localization of GalNAc-T2 in Stably Transformed Tobacco BY 2 Cells
pC1302D-35SPro-AaSP-MUC1-3.5TR-35STerm, 35SPro-T2-35STerm (C2.1)

Stably transformed and expressed GalNAc-T2 is targeted to sub-cellular structures compatible to the Golgi apparatus and thus expected to localize correctly in Golgi membranes of Tobacco suspension BY-2 cells.

FIG. 22. A BY-2 cell line 5.8, transformed with a construct expressing MUC1-3.5TR and GalNAc-T2 (MUC1+T2) from two transcripts (pC1302D-35SPro-AaSP-MUC1-3.5TR-35STerm, 35SPro-T2-35STerm (C2.1)) were shown to express GalNAc-T2 in cellular structures compatible to the Golgi apparatus. Immunostaining of GalNAc-T2 (green) using prim mAb 4C4 in protoplasts of the BY-2 line 5.8 and wild type (WT) BY-2 (control). After immunostaining nuclei were visualised using PI stain (orange).

E5.2 Co-Expression of MUC1-3.5TR and GalNAc-T2 in Stably Transformed *Arabidopsis thaliana*
pC1302D-35SPro-AaSP-MUC1-3.5TR-35STerm, 35SPro-T2-35STerm (C2.1)

Stable co-expression with following structural analysis of MUC1-3.5TR (directed to the secretory pathway by means of the N-terminal fused AaSP signal peptide) and Golgi targeted GalNAc-T2, showed that MUC1-3.5TR is expressed without the presence of plant derived PTMs strongly indicating that plant derived MUC1-3.5TR is not modified by e.g. the endogenous plant prolyl-hydroxylation/O-glycosylation machinery in *A. thaliana* (For ESI-MS data see E4.1.3. Expression of MUC1-3.5TR).

FIG. 23. Western analysis using 5E10 mAb on approximately 30 μg total protein extracts of wt and *Arabidopsis* expressing MUC1-3.5 TR together with GalNAc-T2 transferase (MUC1+T2) (pC1302D-35SPro-AaSP-MUC1-3.5TR-35STerm, 35SPro-T2-35STerm (C2.1)). Positive control: MUC1-3.5 TR expressed in- and purified from *E. coli* (EcMUC1).

Example E6

Introduction of UDP-GalNAc-Transporter

E6 Introduction of UDP-GalNAc-Transporter hUGT1
pC2300-UbiPro-hUGT1-c-myc-35STerm (C7)

*Homo sapiens* hUGT1 (P78381-2) is ectopically expressed in O-glycosylation capacity backgrounds (pC1302-35SPro-HAT2-2A-FWbpP-35STerm (C3.1), pBI121-35SPro-wb-ppF-2A-T2-NosTerm (C3.2), pC1302D-35SPro-AaSP-MUC1-3.5TR-Yfp(H)$_6$-35STerm; 35SPro-T2-2A-FWbp (C6.2), pC1302D-35SPro-FWbpP-35STerm; 35SPro-T2-35STerm (C3.4)). The transporter med be expressed transiently along with other components of the glycosylation machinery or it may be stably expressed in the host cell whether this is used for stable or transient production of the target.

Enhanced GalNAc'ylation of the target is demonstrated using MS and MSMS, see materials and methods. Increase of flux through the secretory pathway is demonstrated by semi-quantitative Western blotting and quantization of recovered glycoprotein from the plant or medium in case of in vitro production.

g) TABLES

Cross Referencing Expressed Enzymes and Hosts

TABLE 1

Enzyme X is active in hosts Y

| Enzyme | Host | | | |
|---|---|---|---|---|
| | *N. benthamiana* | BY-2 cells | *A. thaliana* | *L. minor* |
| Epimerase | | | | |
| Cytoplasmic WbpP (SEQ ID NO 1) | E | | E | nd |
| ER WbpP (SEQ ID NO 2) | E | | | nd |
| Golgi WbpP (SEQ ID NO 3) | E | nd | E | nd |
| Cytoplasmic WbpP (SEQ ID NO 8) | A | A | nd | nd |
| Cytoplasmic WbpP (SEQ ID NO 9) | A | A | nd | nd |
| Cytoplasmic WbpP (SEQ ID NO 23) | A | A | A | nd |
| Cytoplasmic WbpP (SEQ ID NO 10) | A | A | nd | nd |
| Golgi WbpP (SEQ ID NO 11) | A | A | nd | nd |
| Golgi WbpP (SEQ ID NO 22) | A | A | nd | nd |
| Polypeptide GalNAc-Transferases | | | | |
| Golgi GalNAc-T2 (SEQ ID NO 4) | E | E | E | E |
| Golgi GalNAc-T2 (SEQ ID NO 7) | A | | | nd |
| Golgi GalNAc-T2 (SEQ ID NO 8) | A | E | | nd |
| Golgi GalNAc-T2 (SEQ ID NO 9) | A | A | nd | nd |
| Golgi GalNAc-T2 (SEQ ID NO 23) | A | A | A | nd |
| Golgi GalNAc-T2 (SEQ ID NO 5) | nd | nd | nd | nd |
| Golgi GalNAc-T2 (SEQ ID NO 10) | A | A | nd | nd |
| Golgi GalNAc-T2 (SEQ ID NO 11) | A | A | nd | nd |
| Golgi GalNAc-T2 (SEQ ID NO 22) | A | A | nd | nd |
| Golgi GalNAc-T4 (SEQ ID NO 6) | A | nd | nd | nd |

E = Expression/Presence of enzyme as demonstrated by Western analysis or immunostaining. A = Activity demonstrated, nd = not determined; 4 × nd = construct made but not tested Expression and activity determinations: *N. benthamiana* was used for transient *Agrobacterium* mediated expression, while the three other species were stably transformed plants or cell lines.

h)

TABLE 2

Expressed and/or demonstrated O-glycosylation of target peptides for secretion

| Target peptides | N. benthamiana | BY-2 cells | A. thaliana | L. minor | P. patens |
|---|---|---|---|---|---|
| MUC1-3.5TR (SEQ ID NO 12) | G | | E | E | |
| MUC1-3.5TR-CGM (SEQ ID NO 13) | G | | | nd | |
| MUC1-3.5TR-NGM (SEQ ID NO 14) | G | | | nd | |
| MUC1-3.5TR (SEQ ID NO 15) | G | | | nd | |
| NGM-hPod (SEQ ID NO 16) | E | E | nd | nd | |
| MUC1-3.5TR-YFP(H)$_6$(SEQ ID NO 17) | G | G | G | nd | E |
| Yfp-MUC1-3.5TR (SEQ ID NO 18) | E | E | nd | nd | |
| INF-α2B-CGM (SEQ ID NO 19) | G | E | E | nd | |
| MUC1-3.5TR (SEQ ID NO 4) | E | | E | E | |
| Embed G-MUC1-FP(SEQ ID NO 20) | G | G | E | nd | |
| MUC16 1.2TR (SEQ ID NO 21) | G | E | E | nd | |

G = O-glycosylation demonstrated

REFERENCES

Amano K, Chiba Y, Kasahara Y, Kato Y, Kaneko M K, Kuno A, Ito H, Kobayashi K, Hirabayashi J, Jigami Y, Narimatsu H (2008) Engineering of mucin-type human glycoproteins in yeast cells. *Proc Natl Acad. Sci. U.S.A.* 105: 3232-3237.

Bennett E P, Hassan H, Clausen H (1996) cDNA Cloning and Expression of a Novel Human UDP-N-acetyl-a-D-galactosamine polypeptide N-acetylgalactosaminyltransferase, GalNAc-T3. *J Biol Chem* 271(29):17006-12.

Bennett E P, Hassan H, Mandel U, Mirgorodskaya E, Roepstorff P, Burchell J, Taylor-Papadimitriou J, Hollingsworth M A, Merkx G, van Kessel A G, Eiberg H, Steffensen R, Clausen H (1998) *J Biol. Chem.* 273, 30472-30481

Belanger M, Burrows L L, Lam J S (1999) Functional analysis of genes responsible for the synthesis of the B-band O antigen of *Pseudomonas aeruginosa* serotype O6 Lipopolysaccharide. *Microbiol.* 145:3505-3521

Creuzenet C, Belanger M, Wakarchuk W W, Lam J S (2000) Expression, Purification, and Biochemical Characterization of WbpP, a New UDP-GlcNAc C4 Epimerase from *Pseudomonas aeruginosa* Serotype O6. *J Biol Chem*, 275: 19060-19067

Chen Y T, Holcomb C, Moore H P (1993) Expression and localization of two low molecular weight GTP-binding proteins, Rab8 and Rab10, by epitope tag. *Proc Nat. Acad Sc. U.S.A.* 90:6508-6512

Demendi M N, Ishiyama J S, Lam A M, Berghuis, Creuzenet C (2005) Towards a better understanding of the substrate specificity of the UDP-N-acetylglucosamine C4 epimerase WbpP. *Biocheml J.* 389:173-180.

Egelund J, Obel N, Ulvskov P, Geshi N, Pauly M, Bacic A, Petersen B L (2007) Molecular characterization of two *Arabidopsis thaliana* glycosyltransferase mutants, rra-1 and -2, which have a reduced content of arabinose in a polymer tightly associated with the cellulose residue. *Plant Mol Biol* 64:439-451

El Amrani A, Barakate A, Askari B M, Li X, Roberts A G, Ryan M D, Halpin C (2004) Coordinate expression and independent subcellular targeting of multiple proteins from a single transgene. *Plant Physiol.* 135:16-24

Gerken T A, Raman J, Fritz T A, Jamison O (2006) Identification of Common and Unique Peptide Substrate Preferences for the UDP-GalNAc: Polypeptide-N-acetylgalactosaminyltransferases T1 and T2 Derived from Oriented Random Peptide Substrates. *J Biol Chem* 281:32403-32416S Genschik P, Marbach J, Uze M, Feuerman M, Plesse, B and Fleck J (1994) Structure and promoter activity of a stress and developmentally regulated polyubiquitin-encoding gene of *Nicotiana tabacum*. *Gene* 148: 195-202

Gomord V, Faye L (2004) Posttranslational modification of therapeutic proteins in plants. *Current Opinion in Plant Biology* 7:171-181

Hattrup C L, Gendler S J (2008) Structure and function of the cell surface (tethered) mucins. *Annual Review of Physiology.* 70:431-457.

Hieta R, Myllyharju J (2002): Cloning and characterization of a low molecular weight prolyl 4-hydroxylase from *Arabidopsis thaliana*. *Journal of Biological Chemistry.* Vol. 277, no. 26, pp. 23965-23971

Hassan H, Bennett E P, Mandel U, Hollingsworth M A, and Clausen H (2000) Control of Mucin-Type O-Glycosylation: O-Glycan Occupancy is Directed by Substrate Specificities of Polypeptide GalNAc-Transferases. Wiley-VCH chapter "Saccharides in Chemistry and Biology—a Comprehension Handbook" (B. Ernst, G. Hart, and P. Sinay, eds.) Wiley-VCH Publishers, Weinheim, N.Y., Cambridge, pp. 273-292

Horsch R B, Fry J E, Hoffmann N L, Eichholtz D, Rogers S G, Fraley R T (1985) A simple and general method for transferring genes into plants. *Science* 227:1229-1231

Jamet E C, Albenne G, Boudart M, Irshad H, Canut, Pont-Lezica R (2008): Recent advances in plant cell wall proteomics. *Proteomics.* 8: 893-908

Karnoup A S, Turkelson V, Anderson W H K (2005): O-linked glycosylation in maize expressed human IgA1. *Glycobiol* 15: 965-981

Kato K, Jeanneau C, Tarp M A, Benet-Pages A, Lorenz-Depiereux B, Bennett E P, Mandel U, Strom T M, Clausen H (2006) Polypeptide GalNAc-transferase T3 and familial tumoral calcinosis. Secretion of fibroblast growth factor 23 requires O-glycosylation. J Biol Chem 281:18370-7

Kauppinen S, Christgau S, Kofod L V, Halkier T, Dorreich K and Dalboge H (1995) Molecular cloning and characterization of a rhamnogalacturonan acetylesterase from *Aspergillus aculeatus*. Synergism between rhamnogalacturonan degrading enzymes. J Biol Chem 270: 27172-27178

Kobayashi T, Morone N, Kashiyama T, Oyamada H, Kurebayashi N, Murayama T. (2008) Engineering a novel multifunctional green fluorescent protein tag for a wide variety of protein research. *Plos ONE* 3(12):e3822.

Lee J H, Kim N S, Kwon T H, Jong Y S, Yang M S (2002) Increased production of human granulocyte macrophage colony stimulating factor (hGM-CSF) by the addition of stabilizing polymer in plant suspension cultures. *J Biotechnol* 96:205-211

Mandel U, Hassan H, Therkildsen M H, Rygaard J, Jakobsen M H, Juhl B R, Dabelsteen E, Clausen H (1999) Expression of polypeptide GalNAc-transferases in stratified epithelia and squamous cell carcinomas: immunohistological evaluation using monoclonal antibodies to three members of the GalNAc-transferase family. *Glycobiol* 9:43-52

Mayo K J, Gonzales B J, Mason H S (2006) Genetic transformation of tobacco NT1 cells with *Agrobacterium tumefaciens*. *Nature Protocols* 1:1105-1111

Nour-Eldin H H, Hansen B G, Norholm M H H, Jensen J K, Halkier B A (2006): Advancing uracil-excision based cloning towards an ideal technique for cloning PCR fragments. *Nucleic Acids Research*. Vol. 34, no. 18

Odell J T, Nagy F, Chua N H (1985) Identification of DNA sequences required for activity of the cauliflower mosaic virus 35S promoter. *Nature* 313:810-812

Qisen Z, Hrmova M, Shirley N J, Lahnstein J, Fincher G B (2006) Gene expression patterns and catalytic properties of UDP-D-glucose 4-epimerases from barley (*Hordeum vulgare* L.). *Biochem J* (2006) 394: 115-124

Petersen B L, Damager I, Faber K, Jensen J K, Egelund J, Yang Z, Bennett, P E, Scheller H V, Ulvskov P (2009) Assay and heterologous expression in *Pichia pastoris* of plant cell wall type-II membrane anchored glycosyltransferases. *Clycocon J* 26: 1235-1246

Rottger S, White J, Wandall H H, Olivo J C, Stark A, Bennett E P, Whitehouse C, Berger E G, Clausen H, Nilsson T (1998) Localization of three human polypeptide GalNAc-transferases in HeLa cells suggests initiation of O-linked glycosylation throughout the Golgi apparatus *J. Cell Sci.* 111 (Pt 1), 45-60

Schaaf A, Tintelnot S, Baur A, Reski R, Gorr G Decker E L (2005) Use of endogenous signal sequences for transient production and efficient secretion by moss (*Physcomitrella patens*) cells. *Bmc Biotechnology*. Vol. 5

Segawa H, Masao K, Nobuhiro I (2002) Human and *Drosophila* UDP-galactose transporters transport UDP-N-acetylgalactosamine in addition to UDP-galactose. *Eur J Biochem/FEBS* 2002; 269:128-38

Shimizu M T, Igasaki M, Yamada K, Yuasa J, Hasegawa T, Kato H, Tsukagoshi K, Nakamura H, Fukuda K. Matsuoka (2005): Experimental determination of proline hydroxylation and hydroxyproline arabinogalactosylation motifs in secretory proteins. *Plant J.* 42:877-889.

Skjøt M, Pauly M, Bush M S, Borkhardt B, McCann M C, Ulvskov P (2002) Direct Interference with Rhamnogalacturonan I Biosynthesis in Golgi Vesicles. *Plant Physiol* 129: 95-102

Sainsbury F, Lomonossoff G P (2008) Extremely High-Level and Rapid Transient Protein Production in Plants without the Use of Viral Replication. *Plant Physiol* 148:1212-1218

Samac D A, Hironaka C M, Yallaly P E, and Shah D M, (1990) Isolation and Characterization of the Genes Encoding Basic and Acidic Chitinase in *Arabidopsis thaliana*. *Plant Physiol*. 93:907-914

Sorensen S O, Pauly M, Bush M, Skjøt M, McCann M C, Borkhardt B, Ulvskov P (2000) Pectin engineering: Modification of potato pectin by in vivo expression of an endo-1,4-b-D-galactanase. *Proc Natl Acad. Sci. U.S.A.* 97(13): 7639-7644

Sorensen A L, Reis C A, Tarp M A, Mandel U, Ramachandran K, Sankaranarayanan V, Schwientek T, Graham R, Taylor-Papadimitriou J, Hollingsworth M A, Burchell J, Clausen H (2006): Chemoenzymatically synthesized multimeric Tn/STn MUC1 glycopeptides elicit cancer-specific anti-MUC1 antibody responses and override tolerance. *Glycobiol* 16(2):96-107.

Szymczak A L, Workman, Creg J, Wang, Yao, Vignali, Kate M, Dilioglou, Smaroula, Vanin, Elio F, Vignali, Dario A, (2004) Correction of multi-gene deficiency in vivo using a single 'self-cleaving' 2A peptide-based retroviral vector. *Nat Biotech* 22:589-594.

Tarp M A, Sorensen A L, Mandel U, Paulsen H, Burchell J, Taylor-Papadimitriou J, Clausen H (2007) Identification of a novel cancer-specific immunodominant glycopeptides epitope in the MUC1 tandem repeat. *Glycobiol* 17(2): 197-209

Tarp M A, Clausen H (2008): Mucin-type O-glycosylation and its potential use in drug and vaccine development. *Biochimica Et Biophysica Acta-General Subjects*. 1780 (3): 546-563.

Ten Hagen K G, Fritz T A, Tabak L A (2003) All in the family: the UDP-GalNAc: polypeptide N-acetylgalactosaminyl-transferases. *Glycobiol*. 13(1):1R-16R. Epub 2002 Nov. 1

Tiainen P, Myllyharju J, Koivunen P (2005) Characterization of a second *Arabidopsis thaliana* prolyl 4-hydroxylase with distinct substrate specificity. *J Biol Chem* 280(2): 1142-1148.

Wandall H H, Hassan H, Mirgorodskaya E, Kristensen A K, Roepstorff P, Bennet E P, Nielsen P A, Hollingsworth M A, Burchell J, Taylor-Papadimitriou J, Clausen H. (1997) Substrate specificities of three members of the human UDP-N-acetyl-alpha-D-galactosamine: Polypeptide N-acetylgalactosaminyltransferase family, GalNAc-T1, -T2, and -T3. *J Biol. Chem.* 272:23503-23514

Wandall H H, Irazoqui F, Tarp M A, Bennett E P, Mandel U, Takeuchi H, Kato K, Irimura T, Suryanarayanan G, Hollingsworth M A, Clausen H. (2007) The lectin domains of polypeptide GalNAc-transferases exhibit carbohydrate-binding specificity for GalNAc: lectin binding to GalNAc-glycopeptide substrates is required for high density GalNAc-O-glycosylation. *Glycobiol*. 2007, 7:374-87

White T, Bennett E P, Takio K, Sorensen T, Bonding N, Clausen H (1995) Purification and cDNA cloning of a human UDP-N-acetyl-alpha-D-galactosamine: polypeptide N-acetylgalactosaminyltransferase. *J Biol Chem*. 270: 24156-65

Xu J, Tan L, Goodrum K J, Kieliszewski M J (2007) High-yields and extended serum half-life of human interferon 2b expressed in tobacco cells as arabinogalactan-protein fusions. *Biotechnology and Bioengineering* 97:997-1008

Yamamoto Y T, Rajbhandari N, Lin X, Bergmann B A, Nishimura Y, Stomp, A-M (2001) Genetic transformation of duckweed *Lemna gibba* and *Lemna minor*. *In vitro Cell Dev. Biol.—Plant* 37: 349-353.

U.S. Pat. No. 6,465,220—Glycosylation using GalNAc-T4 transferase US Patent Issued on Oct. 15, 2002, Estimated Patent Expiration Date: Dec. 21, 2018, Inventors Hassan, Frau Helle, Clausen, Henrik, Bennett, Eric Paul, Eisenkratzer, Detlef, Gatgens, Jochen.

U.S. Pat. No. 5,871,990 UDP-N-acetyl-.alpha.-D-galactosamine: polypeptide Nacetylgalactosaminyltransferase, GalNAc-T3, 16/2, 1999

U.S. Pat. No. 6,582,910—WbpP and method for assay of WbpP, US Patent Issued on Jun. 24, 2003, No. 580929 filed on May 26, 2000. Inventors: Lam, Joseph S. Creuzenet, Carole United States Patent Application, publication no. 2009-0068702—METHOD FOR PRODUCING A MUCIN-TYPE GLYCOPROTEIN Application Filed on Feb. 26, 2007 Application Published on Mar. 12, 2009

The invention claimed is:

1. A method for sustainable initiation of mammalian O-glycosylation in a plant cell, comprising:
   introducing a DNA vector into a plant cell, by transient or stable transformation, said vector comprising glyco-genes encoding
   a single Uridine-di-phospho N-acetylglucosamine (UDP-GlcNAc)/UDP-Glc C4-epimerase, wherein the UDP-GlcNAc/UDP-Glc C4-epimerase is targeted to the cytosol or Golgi apparatus, and
   at least one polypeptide N-acetylgalactosamine (Gal-NAc)-Transferase, wherein the GalNAc-Transferase is targeted to the Golgi apparatus;
   and without introducing into the plant cell a dedicated UDP-GalNAc transporter.

2. The method according to claim 1, wherein the UDP-GlcNAc/UDP-Glc C4-epimerase is targeted to the cystosol of the plant cell.

3. The method according to claim 1, wherein the UDP-GlcNAc/UDP-Glc C4-epimerase is targeted to the Golgi apparatus.

4. The method according to claim 1, wherein the GalNAc-transferase(s) is/are selected from CAZy family GT27.

5. The method according to claim 4, wherein the GalNAc-Transferase(s) is/are selected among the genes of mammals.

6. The method according to claim 4, wherein the GalNAc-Transferase(s) is/are selected from human Uridine-di-phospho N-acetylgalactosaminyl transferase T2 (UDP-GalNAc-T2) or human Uridine-di-phospho N-acetylgalactosaminyl transferase T4 (UDP-GalNAc-T4).

7. The method according to claim 1, wherein the UDP-GlcNAc/UDP-Glc C4-epimerase is selected from either eukaryotic or prokaryotic C4'-epimerases.

8. The method according to claim 1, wherein the plant cell is selected from the genera *Nicotiana, Arabidopsis, Physcomitrella, Lemna, Hordeum, Triticum* or *Brachypodium*.

9. The method according to claim 1, wherein the plant cell is a Chlorophyte or Charophyte alga.

10. The method according to claim 1, wherein the plant cell is further transformed, transiently or stably, with a nucleotide construct encoding a O-glycosylation target mucin-type protein.

11. The method according to claim 1, wherein the plant cell is further transformed, transiently or stably, with a nucleotide construct encoding a non-mucin-type O-glycosylation target therapeutic-protein.

12. The method according to claim 10, wherein the O-glycosylation target protein is secreted from the cell, in planta or in vitro.

13. The method according to claim 5, wherein the mammal is a human.

* * * * *

UNITED STATES PATENT AND TRADEMARK OFFICE
CERTIFICATE OF CORRECTION

PATENT NO.        : 9,024,110 B2              Page 1 of 1
APPLICATION NO.   : 13/070248
DATED             : May 5, 2015
INVENTOR(S)       : Zhang Yang et al.

It is certified that error appears in the above-identified patent and that said Letters Patent is hereby corrected as shown below:

On the Title page, item (76) Inventor: "Brent Larsen Petersen" should read -- Bent Larsen Petersen --.

Signed and Sealed this
Twenty-fifth Day of August, 2015

Michelle K. Lee
*Director of the United States Patent and Trademark Office*